United States Patent [19]

Paulson et al.

[11] Patent Number: 5,753,631
[45] Date of Patent: May 19, 1998

[54] INTERCELLULAR ADHESION MEDIATORS

[75] Inventors: James C. Paulson, Sherman Oaks; Mary S. Perez, Carlsbad; Federico C. A. Gaeta, La Jolla; Robert M. Ratcliffe, Carlsbad, all of Calif.

[73] Assignee: Cytel Corporation, San Diego, Calif.

[21] Appl. No.: 457,886

[22] Filed: May 31, 1995

Related U.S. Application Data

[60] Division of Ser. No. 63,181, May 14, 1993, which is a continuation-in-part of Ser. No. 810,789, Dec. 17, 1991, abandoned, which is a continuation-in-part of Ser. No. 716,735, Jun. 17, 1991, abandoned, which is a continuation-in-part of Ser. No. 632,390, Dec. 21, 1990, abandoned, which is a continuation-in-part of Ser. No. 619,319, Nov. 28, 1990, abandoned, which is a continuation-in-part of Ser. No. 538,853, Jun. 15, 1990, abandoned.

[51] Int. Cl.$^6$ ............................. A61K 31/70; C07H 15/00
[52] U.S. Cl. ..................... 514/25; 514/8; 514/54; 514/61; 514/62; 536/17.2; 536/18.2; 536/18.7; 536/53; 536/54; 536/55; 536/55.1; 536/55.2
[58] Field of Search ..................... 514/8, 25, 54, 514/61, 62; 536/17.2, 18.2, 18.7, 53, 54, 55, 55.1, 55.2

[56] References Cited

U.S. PATENT DOCUMENTS

| | | | |
|---|---|---|---|
| 4,904,596 | 2/1990 | Hakomori | 435/7.23 |
| 5,079,353 | 1/1992 | Ratcliffe et al. | 536/53 |
| 5,296,594 | 3/1994 | Ratcliffe et al. | 536/53 |
| 5,324,663 | 6/1994 | Lowe | 435/320.1 |
| 5,344,870 | 9/1994 | Ratcliffe et al. | 525/54.2 |
| 5,428,025 | 6/1995 | Brandley et al. | 514/55 |

FOREIGN PATENT DOCUMENTS

| | | |
|---|---|---|
| 62-273919 | 11/1987 | European Pat. Off. |
| WO 90/13300 | 11/1990 | WIPO |
| WO 91/06632 | 5/1991 | WIPO |
| WO 91/07993 | 6/1991 | WIPO |
| WO 91/19502 | 12/1991 | WIPO |
| WO 92/07572 | 5/1992 | WIPO |

OTHER PUBLICATIONS

Johnson, Philip H., et al. (1985) "Sialyl compounds as acceptor substrates for the human $\alpha$-3-and $\alpha$-3/4-L-fucosyltransferases", *Biochem. Soc. Trans.*, 13(6):1119–1120.

Ching, C.K., et al. (1990) "Purification and Characterization of a Peanut–Agglutination–Binding Pancreatic–Cancer–Related Serum Mucus Glycoprotein", *Int. J. Cancer,* 45:1022–1027.

Rosen, Steven D., et al. (1986) "Lymphocyte attachment to high endothelial venules during recirculation: A possible role for carbohydrates as recognition determinants", *Molecular and Cellular Biochemistry,* 72:153–164.

Underhill, Charles, et al. (1978) "The Role of Hyaluronic Acid in Intercellular Adhesion of Cultured Mouse Cells", *Experimental Cell Research,* 117:155–164.

Picker, Louis J., et al. (1991) "The Neutrophil Selectin LECAM–1 Present Carbohydrate Ligands to the Vascular Selectins ELAM–1 and GMP–140", *Cell* 66:921–933.

Tyrrell, David, et al. (1991) "Structural requirements for the carbohydrate ligand of E–selectin", *Proc. Natl. Acad. Sci USA,* 88:10372–10376.

Derwent Publications Ltd., London, GB: AN 90–135674 & JP–A–02 83 337 (Nichirei KK) Mar. 23, 1990. Abstract.

Kannagi, Reiji, et al. (1982) "Possible role of ceramide in defining structure and function of membrane glycolipids", *Proc. Natl. Acad. Sci USA,* 79:3470–3474.

Hakomori, Sen–itiroh, et al. (1984) "Novel Fucolipids Accumulating in Human Adenocarcinoma", *The Journal of Biological Chemistry,* 259(7):4672–4680.

Fukushi, Yasuo, et al. (1984) "Novel Fucolipids Accumulating in Human Adenocarcinoma", *The Journal of Biological Chemistry,* 259(16):10511–10517.

Holmes, Eric H., et al. (1985) Enzymatic Basis for the Accumulation of Glycolipids with X and Dimeric X Determinants in Human Lung Cancer Cells (NCI–H69), *The Journal of Biological Chemistry,* 260(12:7619–7627.

Fukuda, Michiko N., et al. (1986) "Structure of a Novel Pialylated Fucosyl Lacto–N–nor–hexaosylceramide Isolated from Chronic Myelogenous Leukemia Cells", *The Journal of Biological Chemistry,* 261(5):2376–2383.

McIntire, Floyd C., et al. (1988) "A polysaccharide fromn *Streptococcus sanguis* 34 that inhibits Coaggregation of *S. sanguis* 34 with *Actinomyces viscous* T14V", *Journal of Bacteriology,* 170(5:2229–2235.

Nilsson, Kurt G.I. (1988) "Enzymatic synthesis of oligosaccharides" *Trends in Biotechnology,* 6:256–264.

Cassels, Frederick J., et al. (1989) "Isolation of a Coaggregation–Inhibiting Cell Wall Polysaccharide from *Streptococcus sanguis* H1", *Journal of Bacteriology,* 171(7):4019–4025.

Finne, Jukka, et al. (1989) "Novel Polyfucosylated N–Linked Glycopeptides with Blood Group A,H,X and Y Determinants from Human Small Intestinal Epithelial Cells", *The Journal of Biological Chemistry,* 264(10):5720–5735.

(List continued on next page.)

*Primary Examiner*—Kathleen K. Fonda
*Attorney, Agent, or Firm*—Townsend and Townsend and Crew LLP

[57] ABSTRACT

The present invention is directed towards compositions and methods for reducing or controlling inflammation and for treating inflammatory disease processes and other pathological conditions mediated by intercellular adhesion. The compositions of the invention include compounds that selectively bind selectin receptors, the selectin binding activity being mediated by a carbohydrate moiety. The selectin-binding moieties of the invention are derivatives of a sialylated, fucosylated N-acetyllactosamine unit of the Lewis X antigen. Compounds containing a selectin-binding moiety in both monovalent and multivalent forms are included in the invention. The compounds of the invention are provided as pharmaceutical compositions which include, for example, liposomes that carry selectin-binding moieties of the invention. The invention further includes immunoglobulins capable of selectively binding an oligosaccharide ligand that is recognized by a selectin receptor.

9 Claims, 24 Drawing Sheets

OTHER PUBLICATIONS

Levery, Steven B., et al. (1988) "H–N.M.R. Analysis of Type–2 Chain Lacto–Gangliosides. Confirmation of Structure of a Novel Cancer–Associated Fucoganglioside", *Carbohydrate Research*, 178:121–144.

Hakamori, et al. (1984) *J. Biol. Chem.*, 259(7):4672–4680.

Sakura (1989) *Chemical Abstracts*, 111:151639b.

Hansson, Gunnar, C., et al. (1983) "Mouse Monoclonal Antibodies against Human Cancer Cell Lines with Specfificities for Blood Group and Related Antigens", *The Journal of Biological Chemistry*, 258(7):4091–4097.

Hakomori, Sen–itiroh (1985) "Aberrant Glycosylation in Cancer Cell Membranes as Focused on Glycolipids: Overview and Perspectives", *Cancer Research* 435:2405–2414.

Yoichi, Sakurai, et al. (1989) "Production and clinical application of monoclonal antibodies NCC–CO–450, –473 reactive with high–molecular–weight glycoprotein circulating in body fluid of gastrointestinal cancer patients", (Abstract), *Immunochemistry*, 111:531.

Hautanen, Aarno, et al. (1989) "Effects of Modifications of the RGD Sequence and Its Context on Recognition by the Fibronectin Receptor", *The Journal of Biological Chemistry*, 264(3):1437–1442.

Eggens, Ivan, et al. (1989) "Specific Interaction Between $Le^x$ and $Le^x$ Determinants", *The Journal of Biological Chemistry*, 264(16):9476–9484.

Shitara, Kenya, et al. (1991) "Application of anti–Sialyl $Le^a$ Monoclonal antibody, KM231, for Immunotherapy of Cancer", *Anticancer Research*, 11:2003–2014.

Zhou, Qun, et al. (1991) "The Selectin GMP–140 Binds to Sialylated, Fucosylated Lactosaminoglycans on Both Myeloid and Nonmyeloid Cells", *The Journal of Cell Biology*, 115(2):557–564.

Polley, Margaret J., et al. (1991) "CD62 and endothelial cell–leukocyte adhesion molecule 1 (ELAM–1) recognize the same carbohydrate ligand, sialyl–Lewis x", *Proc. Natl. Acad. Sci*, 88:6224–6228.

Leeuwenberg, Jet F.M., et al., "IFN–γ Regulates the Expression of the Adhesion Molecule Elam–1 and IL–6 Production by Human Endothelial Cells In Vitro", *Journal of Immunology*, 145:2110–2114 (1990).

Graber, Norma, et al., "T Cells Bind to Cytokine–Activated Endothelial Cells Via a Novel, Inducible Sialoglycoprotein and Endothelial Leukocyte Adhesion Molecule–1", *Journal of Immunology*, 145:819–830 (1990).

Koch, Alisa E., et al., "Immunolocalization of endothelial and Leukocyte Adhesion Molecules in Human Rheumatoid and Osteoarthritic Synovial Tissues", *Laboratory Investigation*, 64 (3) : 313–320 (1991).

Osborn, Laurelee, "Leukocyte Adhesion to Endothelium in Inflammation", *Cell*, 62:3–6 (1990).

Springer, Timothy A., "Adhesion receptors of the immune system", *Nature*, 346:425–434 (1990).

Waltz, Gerd, et al., "Recognition by ELAM–1 of the Sialyl–$Le^x$ Determinant on Myeloid and Tumor Cells", *Science*, 250:1132–1135 (1990).

Zetter, Bruce R., "The Cellular Basis of Site–Specific Tumor Metastasis", *The New England Journal of Medicine*, 322(9):605–612 (1990).

Gamble, Jennifer R., et al., "Prevention of Activated Neutrophil Adhesion to Endothelium by Soluble Adhesion protein GNP140", *Science*, 249:414–417 (1990).

Brandley, Brian K., et al., "Carbohydrate Ligands of the LEC Cell Adhesion Molecules", *Cell*, 63:861–863 (1990).

Parmentier, Sophie, et al., "Inhibition of Platelet Functions by a Monoclonal Antibody (LYP20) Directed Against a Granule Membrane Glycoprotein (GMP–140/PADGEM)", *Blood*, 77(8):1734–1739 (1991).

Skinner, Michael P., et al., "GMP–140 Binding to Neutrophils Is Inhibited by Sulfated Glycans", *Journal of Biological Chemistry*, 266(9):5371–5374 (1991).

Goelz, Susan E., "ELFT: A Gene That Directs the Expression of an ELAM–1 Ligand", *Cell*, 63:1349–1356 (1990).

Berg, Ellen L., et al., "A Carbohydrate Domain Common to Both Sialyl Le(a) and Sialyl (x) is Recognized by the Endothelial Cell Leukocyte Adhesion Molecule ELAM–1", *Journal of Biological Chemistry*, 266(23):14869–14872 (1991).

Lasky, Laurence A., et al., "The Lectin Cell Adhesion Molecules (LEC–CAMs): A New Family of Cell Adhesion Proteins Involved with Inflammation" *Journal Cell Biochemistry*, 45(2):139–146 (1991).

Phillips, M. Laurie, et al., "ELAM–1 Mediates Cell Adhesion by Recognition of a Carbohydrate Ligand, Sialyl–Le(x)", *Science*, 250:1130–1132 (1990).

Picker, Louis J., et al., ELAM–1 is an adhesion molecule for skin–homing T Cells, *Nature*, 349:796–799 (1991).

Tiemeyer, Michael, et al., Carbohydrate ligands for endothelial–leukocyte adhesion molecule III, *Proc. Nat. Acad. Sci.*, 88:1138–1142 (1991).

Shimizu, Yoji, et al., "Activation–independent binding of human memory T cells to adhesion molecule ELAM–1", 349:799–802 (1991).

P.J. Green, et al., (1992) "High Affinity Binding of the Leucocyte Adhesion Molecule L–Selectin to 3'–Sulphated–$Le^a$ and –$Le^x$ Oligosaccharides and the Predominance of Sulphate in this Interaction Demonstrated by Binding Studies with a Series of Lipid–Linked Oligosaccharides," *Biochemical and Biophysical Research Communications*, 188(1):244–251.

G. Hortin, et al., (1981) "Metabolic Labeling of Lutropin with [$^{35}$S] sulfate," *Proc. Natl. Acad. Sci. USA* 78(2):7468–7472.

N. Gesundheit, et al. (1986) "Differential Sulfation and Sialylation of Secreted Mouse Thyrotropin (TSH) Subunits: Regulations by TSH–Releasing Hormone," *Endocrinology* 119(2):455–463.

Y. Kato, et al. (1989) "Characterization of a Thyroid Sulfotransferase Responsible for the 3–0–Sulfation of Terminal B–D–Galactosyl Residues in N–Linked Carbohydrate Units," *The Journal of Biological Chemistry* 264(6):3364–3371.

Koshitomo, JP62273919, Nov. 28, 1987, Chem. Abstr. 109:66886.

Lowe et al. *Cell* Nov. 2, 1990, vol. 63, pp. 475–484.

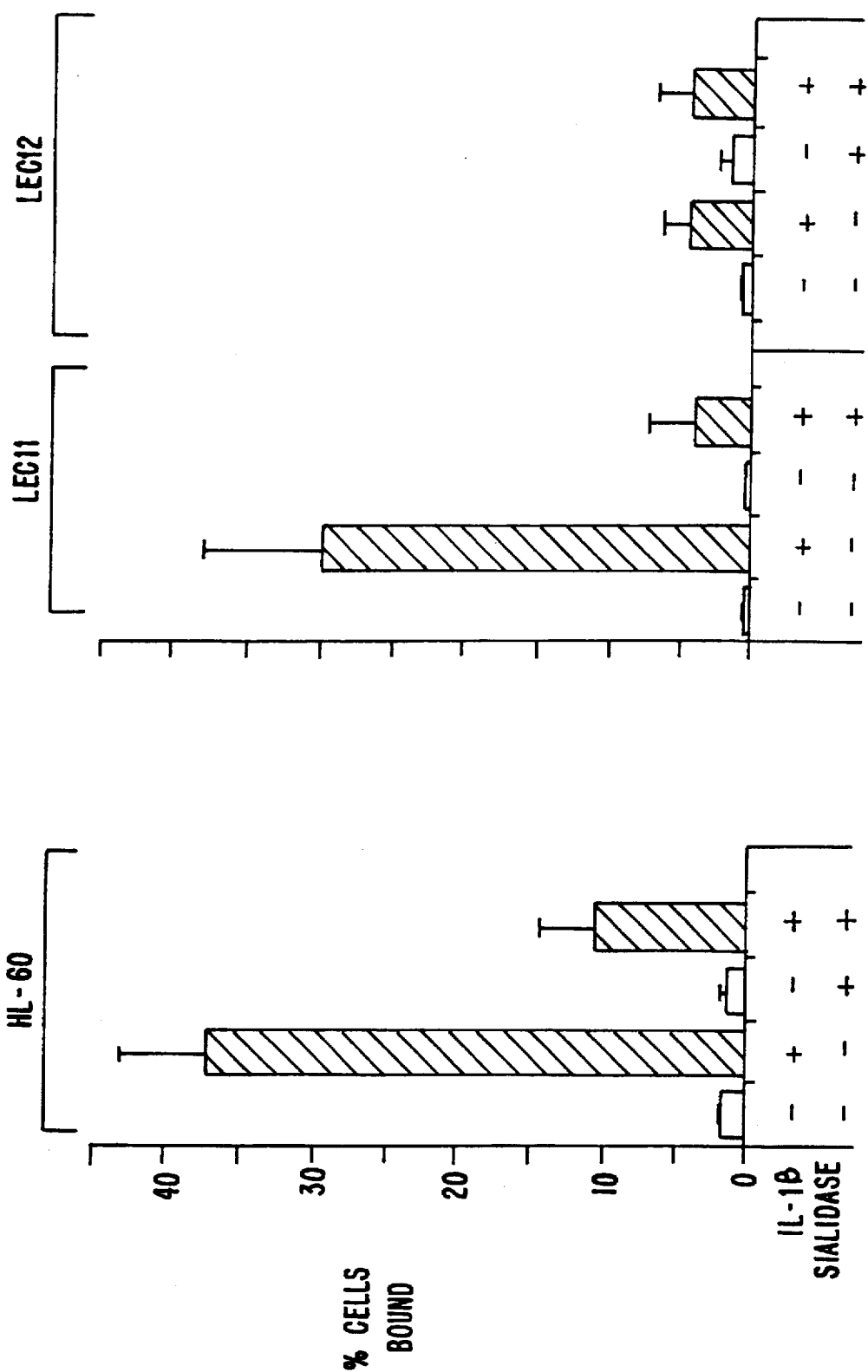

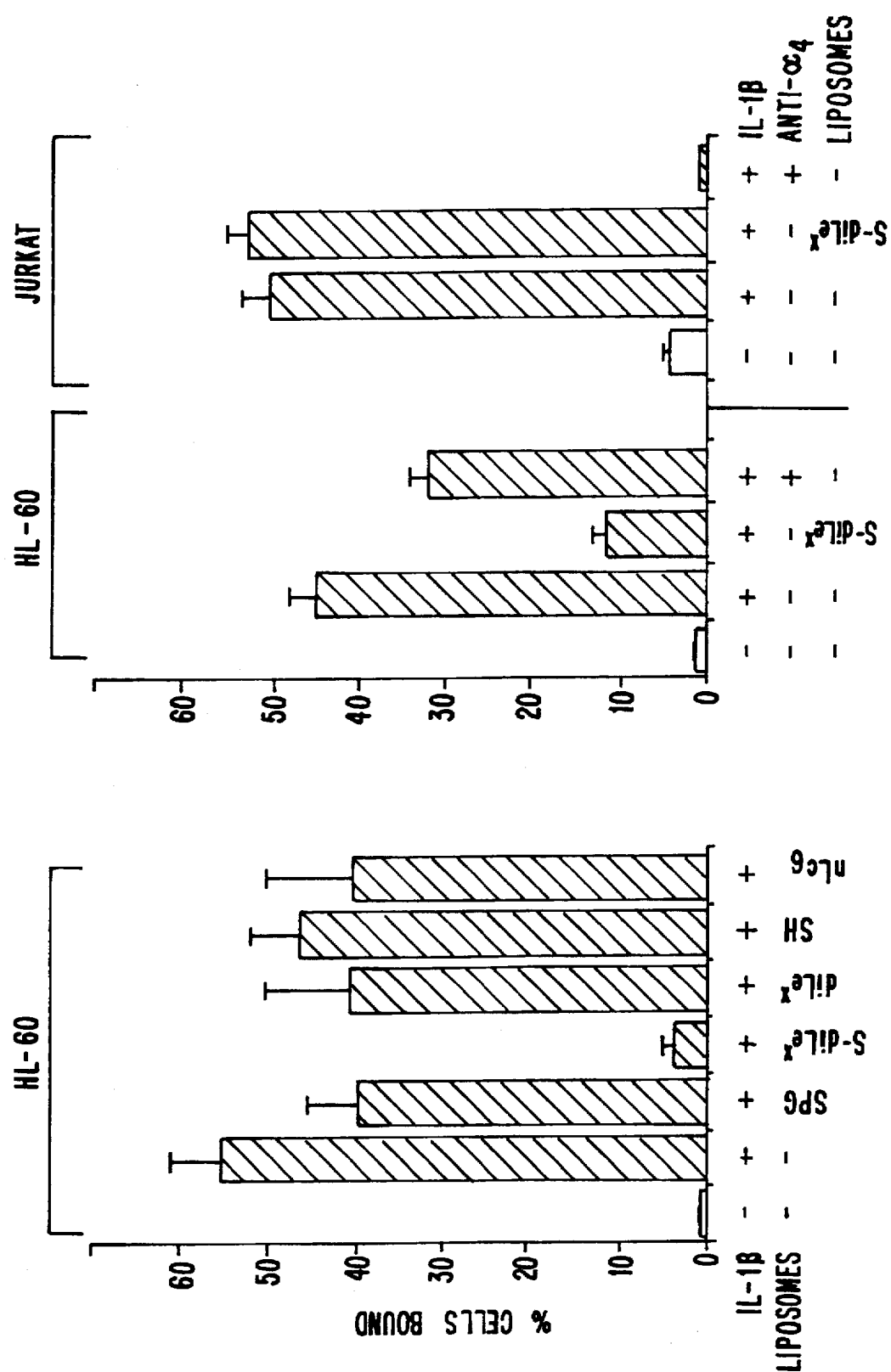

COMPOUND Z
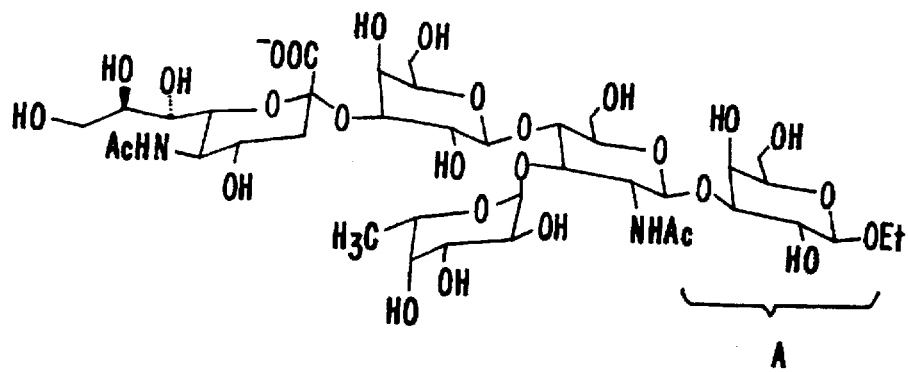
| COMPOUND NUMBER | A | RATIO Z IC$_{50}$ /COMPOUND IC$_{50}$ |
|---|---|---|
| XII | 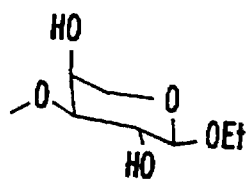 | 0.92 |
| XIII |  | 0.87 |
| XIV | 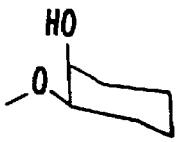 | 1.0 |
| XV |  | 1.0 |
| XVI |  | 1.0 |
FIG. 12B-1.

| | | |
|---|---|---|
| XVII | (structure: methylated sugar with O(CH₂)₃COOMe) | 1.0 |
| XVIII | (structure: methylated sugar with OH) | 1.0 |
| XIX | (structure: methylated sugar) | 1.0 |
| XX | (structure: methylated sugar with O-benzyl) | 1.0 |
| XXIII | (structure: methylated sugar with O(CH₂)₇CH₃) | 2.0 |
| XXIV | (structure: methylated sugar with O(CH₂)₉CH₃) | 2.5 |
| XXV | (structure: methylated sugar with O(CH₂)₁₁CH₃) | 3.7 |
| XXVI | (structure: methylated sugar with O(CH₂)₁₇CH₃) | 3.7 |

FIG. 12B-2.

XXI 5.7

XXII 2.28

INTERCELLULAR ADHESION MEDIATORS

CROSS-REFERENCE TO RELATED APPLICATIONS

This is a Division of application Ser. No. 08/063,181 filed May 14, 1993, which a continuation-in-part of U.S. Ser. No., 07/810,789 (filed Dec. 17, 1991, now abandoned) which is a continuation in part of 07/716,735 (filed Jun. 17, 1991, now abandoned), which is a continuation-in-part of U.S. Ser. No. 07/632,390 (filed Dec. 21, 1990, now abandoned), which is a continuation-in-part of U.S. Ser. No. 07/619,319 (filed Nov. 28, 1990, now abandoned), which is a continuation in-part of Ser. No. 07/538,853 (filed Jun. 15, 1990, now abandoned), all of which disclosures are herein incorporated by reference.

FIELD OF THE INVENTION

The present invention relates to compositions and methods for reducing or controlling inflammation and for treating inflammatory disease processes and other pathological conditions mediated by intercellular adhesion.

BACKGROUND OF THE INVENTION

Vascular endothelial cells and blood platelets play key roles in a number of biological responses by selectively binding certain cells, for instance phagocytic leukocytes, in the blood stream. For example, endothelial cells preferentially bind monocytes and granulocytes prior to their migration through the blood vessel wall and into surrounding tissue in an inflammatory response. Certain inflammation-triggering compounds are known to act directly on the vascular endothelium to promote the adhesion of leukocytes to vessel walls. Cells then move through the walls and into areas of injury or infection. Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes which are thought to be mediated by this process include atherosclerosis, blood clotting and inflammation.

Recent work has revealed that specialized cell surface receptors on endothelial cells and platelets, designated endothelial leukocyte adhesion molecule-1 (ELAM-1, E-Selectin) and granule membrane protein-140 (GMP-140, P-Selectin), respectively, are involved in the recognition of various circulating cells by the endothelium and platelets. These receptors are surface glycoproteins with a lectin-like domain, a region with homology to epidermal growth factor, and a region with homology to complement regulatory proteins (see, Bevilacqua et al., *Science* 243:1160 (1989), which is incorporated herein by reference). For example, E-Selectin has been shown to mediate endothelial leukocyte adhesion, which is the first step in many inflammatory responses. Specifically, E-Selectin binds human neutrophils, monocytes, eosinophils, certain T-lymphocytes (N. Graber et al., *J. Immunol.*, 145:819 (1990)), NK cells, and the promyelocytic cell line HL-60.

The term "selectin" has been suggested for a general class of receptors, which includes E-Selectin and P-Selectin because of their lectin-like domain and the selective nature of their adhesive functions. These cell surface receptors are expressed on a variety of cells. P-Selectin (also known as PADGEM) is present on the surface of platelets and endothelial cells, where it mediates platelet-leukocyte and endothelium-leukocyte interactions. Another member of the selectin class is the MEL-14 antigen, and its human analog LAM-1, which are cell surface receptors of lymphocytes, and act as lymph node homing receptors. The exact nature of the ligand recognized by selectin receptors remains unknown.

Various other methods have been previously developed to block the action of selectins and thus inhibit cellular adhesion. For instance, the use of monoclonal antibodies directed to E-Selectin has been proposed as a method to inhibit endothelial-leukocyte adhesion as a treatment for pathological responses, such as inflammation. Endothelial interleukin-8 has also been shown to be an inhibitor of leukocyte-endothelial interactions.

With the elucidation of the ligand-receptor interaction, it will be possible to develop highly specific, efficient inhibitors of selectin-mediated cellular adhesion which would be useful in therapeutic regimens. The ligand(s) could also be used to target other pharmaceutical compounds, such as anti-inflammatory agents or anti-oxidants, to the sites of injury. To date, insufficient understanding of the interaction of the ligand(s) and receptor molecules on the respective cells has hindered these efforts. The present invention fulfills these and other related needs.

SUMMARY OF THE INVENTION

Novel compositions comprising compounds which selectively bind selectin receptors are provided by the present invention. The compounds of the invention comprise at least one selectin-binding carbohydrate moiety. The selectin-binding moieties are derivatives of a sialylated, fucosylated N-acteyllactosamine unit of the Lewis X antigen. A preferred compound is Z (NeuAc$\alpha$2,3Gal$\beta$1,4(Fuc$\alpha$1,3) GlcNAc$\beta$1,3Gal$\beta$-OCH$_2$CH$_3$). The claimed compositions inhibit intercellular adhesion mediated by the selectin cell surface receptor and thereby are capable, for example, of inhibiting inflammatory and other pathological responses associated with cellular adhesion.

The compounds of the invention may be prepared from a polysaccharide having a repeat unit comprising the unfucosylated SLe$^x$ core structure. Upon fucosylation, a polyvalent SLe$^x$-bearing polysaccharide is obtained. Preferred polysaccharides for this purpose are type Ia, type II, and type III polysaccharides from Group B streptoccus. In related embodiments the compound may be an oligosaccharide or a glycoconjugate, such as a glycoprotein or a glycolipid. Polyvalent selectin-binding compounds may be obtained by linking selectin-binding moieties through various linker moieties.

The present invention specifically provides the above compounds in pharmaceutical compositions. The pharmaceutical compositions can comprise, for example, liposomes which comprise a moiety capable of selectively binding a selectin receptor and a pharmaceutically acceptable carrier. The liposome having the moiety may also serve as a targeting vehicle for a conventional chemotherapeutic agent, which agent is encapsulated within the liposome and delivered to targeted cells which express a selectin receptor. Typically the chemotherapeutic agent is an anti-inflammatory agent or an anti-oxidant. Using the moieties described herein to target chemical agents encapsulated within liposomes is a convenient and effective method for reducing therapeutic levels of a drug and minimizing side effects.

The pharmaceutical compositions of the present invention may also comprise immunoglobulins capable of selectively binding an oligosaccharide ligand recognized by a selectin receptor. Suitable immunoglobulins for this purpose include CSLEX-1, FH6, SNH3, SNH4 and VIM-2.

In other aspects, the invention comprises methods of inhibiting intercellular adhesion in a patient for a disease process, such as inflammation, by administering to the patient a therapeutically effective dose of a compound comprising a moiety capable of binding a selectin receptor. The selectin receptor, such as E-Selectin or P-Selectin, may be expressed on vascular endothelial cells or platelets. The inflammatory process may be, for example, septic shock, wound associated sepsis, rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, nephritis, and acute and chronic inflammation, including atopic dermatitis, psoriasis, and inflammatory bowel disease. Various platelet-mediated pathologies such as atherosclerosis and clotting can also-be treated. In addition, tumor metastasis can be inhibited or prevented by inhibiting the adhesion of circulating cancer cells. Examples include carcinoma of the colon and melanoma.

BRIEF DESCRIPTION OF THE FIGURES

(FIG. 2A) and 4° C. (FIG. 2B) compared to monoclonal antibodies which do not bind SLe$^x$ determinants.

FIGS. 4A and 4B illustrate the results obtained treating HL-60, LEC11 and LEC12 cells with sialidase before binding to activated endothelial cells.

FIGS. 5A and 5B compare the ability of liposomes which contain glycolipids with SLe$^x$, Le$^x$, or similar carbohydrate structures to inhibit the binding of HL-60 cells to activated endothelial cells.

DESCRIPTION OF THE PREFERRED EMBODIMENT

Figure 1:
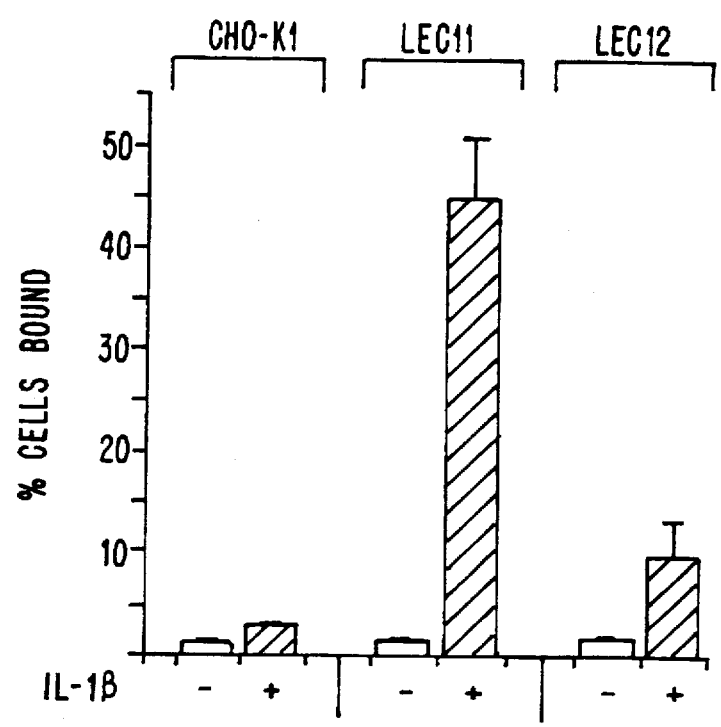
FIG. 1 illustrates the ability of cells which express SLe$^x$ (LEC 11) to bind to IL-1$\beta$ activated endothelial cells compared to those cells which express non-sialylated Le$^x$ (CHO-K1 and LEC 12).

Compositions and methods are provided for inhibiting inflammatory and other disease responses mediated by cellular adhesion. The present invention also provides compounds (e.g., oligosaccharides, glycoconjugates and monoclonal antibodies) which have the ability to block or inhibit the adhesion of the cells mediated by selectin cell surface receptors. Methods for preparing and screening for such compounds are also provided. Diagnostic and therapeutic uses for the compounds are provided.

A basis of the present invention is the discovery of a carbohydrate moiety recognized by selectin cell surface receptors. As discussed above, selecting, also known as the "LEC-CAM" or selectin family of cell adhesion molecules, are unique glycoproteins expressed on the surface of a variety of cells. For instance, E-Selectin is inducibly expressed on vascular endothelial cells (Bevilacqua et al., supra and Hession et al., *Proc. Natl. Acad. Sci.*, 87:1673–1677 (1990), both of which are incorporated herein by reference). This receptor has been demonstrated to be induced by inflammatory cytokines such as interleukin Iβ (IL-Iβ) and tumor necrosis factor α (TNFα), as well as by bacterial endotoxin (lipopolysaccharide) (see, Bevilacqua et al., *Proc. Natl. Acad. Sci.*, 84:9238–9242 (1987) which is incorporated herein by reference). These compounds act directly on endothelial cells in vitro to substantially augment polymorphonuclear leukocyte (neutrophil), and monocyte adhesion (Bevilacqua et al., *Proc. Natl. Acad. Sci.*, supra).

As discussed above, P-Selectin is a membrane glycoprotein of platelet and endothelial secretory granules (Geng et al., *Nature*, 343:757–760 (1990) which is incorporated herein by reference). Activated platelets which express P-Selectin on their surface are known to bind to monocytes and neutrophils (Jungi et al., *Blood* 67:629–636 (1986)), and also to monocyte-like cell lines, e.g., HL60 and U937 (Jungi et al., supra; Silverstein et al., *J. Clin. Invest.* 79:867–874 (1987)), all of which are incorporated herein by reference. P-Selectin is an alpha granule membrane protein of molecular weight 140,000 that is expressed on the surface of activated platelets upon platelet stimulation and granule secretion (Hsu-Lin et al., *J. Biol. Chem.* 259:9121–9126 (1984); Stenberg et al., *J. Cell Biol.* 101:880–886 (1985); Berman et al., *J. Clin. Invest.* 78:130–137 (1986)). It is also found in megakaryocytes (Beckstead et al., *Blood* 67:285–293 (1986)), and in endothelial cells (McEver et al., *Blood* 70:355a (1987)) within the Weibel-Palade bodies (Bonfanti et al., *Blood* 73:1109–1112 (1989)). Furie et al. U.S. Pat. No. 4,783,330, describe monoclonal antibodies reactive with P-Selectin. All of the foregoing references are incorporated herein by reference.

A third selectin receptor is the lymphocyte homing receptor, MEL-14 antigen or LAM-1 (Gallatin et al., *Nature* 304:30–34 (1983); Siegellman et al., *Science*, 243:1165–1172 (1989); Rosen, *Cell Biology*, 1:913–919 (1989); and Lasky et al. *Cell* 56:1045–1055 (1989) all of which are incorporated herein by reference). In addition to lymphocyte homing, MEL-14 antigen/LAM-1 is believed to function early in neutrophil binding to the endothelium.

The structure and function of selectin receptors has been elucidated by cloning and expression of full length cDNA encoding each of the above receptors (see, e.g., Bevilacqua et al., *Science*, supra, (E-Selectin), Geng et al., supra, (GMP 140), and Lasky et al., supra, (MEL-14 antigen)). The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263: 9557–9560 (1988) (which is incorporated herein by reference) that includes low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

Since selectin receptors comprise a lectin-like domain, the specificity of the molecules is likely to be based on protein-carbohydrate interactions. Evidence provided here indicates that a sialylated, fucosylated N-acetyllactosamine unit of the Lewis X antigen, designated here as SLe$^x$, is a moiety recognized by the lectin region of the selectin receptor. In particular, the evidence shows recognition of this moiety by both E-Selectin and P-Selectin. Compounds of the present invention comprise this fucosylated, sialylated N-acetyllactosamine unit in a variety of configurations.

Selective binding as used herein refers to specific recognition by one molecule (typically referred to as a receptor) of another molecule (typically referred to as a ligand) by the spatial or polar organization of a determinant site on the second molecule. Selective binding between the two molecules occurs where affinity is sufficiently strong. Binding affinity is typically represented by the affinity constant (Ka) for equilibrium concentrations of associated and disassociated configurations, i.e., Ka=[R-L]/[R] [L] where [R], [L], and [R-L] are the concentrations at equilibrium of the receptor (R), ligand (L) and receptor-ligand complex (R-L), respectively.

The specific binding interactions of the receptor and ligand molecules typically include reversible noncovalent associations such as electrostatic attraction, Van der Waals forces, and hydrogen bonds. See generally, Stryer, *Biochemistry* (W. H. Freeman and Company, New York 3rd Ed. 1988), which is incorporated herein by reference. Examples of selective binding interactions include antibody-antigen recognition, enzyme-substrate recognition, and the like.

The nomenclature used to describe the oligosaccharide moieties of the present invention follows the conventional nomenclature. Standard abbreviations for individual monosaccharides are used. For instance, 2-N-acetylglucosamine is represented by GlcNAc, fucose is Fuc, galactose is Gal, and glucose is Glc. Two sialic acids which may be present on the oligosaccharides of the present invention are 5-N-acetylneuraminic acid (NeuAc) and 5-N-glycolylneuraminic acid (NeuGc). Unless otherwise indicated, all sugars except fucose (L-isomer) are D-isomers in the cyclic configuration (e.g., pyranose or furanose). The two anomers of the cyclic forms are represented by α and β.

The monosaccharides are generally linked by glycosidic bonds to form oligo- and polysaccharides. The orientation of the bond with respect to the plane of the rings is indicated by α and β. The particular carbon atoms that form the bond between the two monosaccharides are also noted. Thus, a β glycosidic bond between C-1 of galactose and C-4 of glucose is represented by Galβ1,4Glc. For the D-sugars (e.g., D-GlcNAc, D-Gal, and D-NeuAc) the designation α means that, when the sugars are represented by Haworth projection drawings (as described in Stryer, supra.), the hydroxyl attached to C-1 (C-2 in NeuAc) is below the plane of the ring and β is above the ring. In the case of L-fucose, the α designation means the hydroxyl is above the ring and β means it is below, again when the sugar is represented by Haworth projection drawings.

The present invention provides a variety of compounds comprising selectin-binding carbohydrate moieties. The selectin-binding moieties of the invention have the general formula:

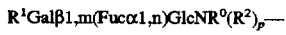

in which $R^0$ is $(C_1-C_8$ alkyl)carbonyl, $(C_1-C_8$ alkoxy) carbonyl, or $(C_2-C_9$ alkenyloxy)carbonyl, $R^1$ is an oligosaccharide or a group having the formula

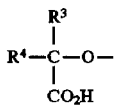

$R^3$ and $R^4$ may be the same or different and may be H, $C_1-C_8$ alkyl, hydroxy-$(C_1-C_8$ alkyl), aryl-$((C_1-C_8$ alkyl), or $(C_1-C_8$ alkoxy)-$(C_1-C_8$ alkyl), substituted or unsubstituted. $R^2$ may be H, $C_1-C_8$ alkyl, hydroxy-$(C_1-C_8$ alkyl), aryl-$(C_1-C_8$ alkyl), $(C_1-C_8$ alkyl)-aryl, alkylthio, α1,2Man, α1,6GalNAc, β1,3Galβ1,4Glc, α1,2Man-$R^8$, α1,6GalNAc-$R^8$, and β1,3Gal-$R^8$. $R^8$ may be H, $C_1-C_8$ alkyl, $C_1-C_8$ alkoxy, hydroxy-$(C_1-C_8$ alkyl), aryl-$(C_1-C_8$ alkyl), $(C_1-C_8$ alkyl)-aryl, or alkylthio. In the formula, m and n are integers and may be either 3 or 4; p may be zero or 1.

The substituted groups mentioned above may be substituted by hydroxy, hydroxy$(C_1-C_4$ alkyl), polyhydroxy $(C_1-C_4$ alkyl), alkanoamido, or hydroxyalknoamido substituents. Preferred substituents include hydroxy, polyhydroxy$(C_3$ alkyl), acetamido and hydroxyacetamido. A substituted radical may have more than one substitution, which may be the same or different.

For embodiments in which $R^1$ is an oligosaccharide, the oligosaccharide is preferably a trisaccharide. Preferred trisaccharides include NeuAcα2,3Galβ1,4GlcNAcβ1,3 or NeuGcα2,3Galβ1,4GlcNAcβ1,3.

For embodiments in which $R^1$ is the group having the formula

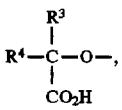

$R^3$ and $R^4$ preferably form a single radical having the formula

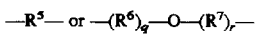

in which $R^5$ is $C_3-C_7$ divalent alkyl, substituted or unsubstituted, $R^6$ and $R^7$ are the same or different and are $C_1-C_6$ divalent alkyl, substituted or unsubstituted. In the formula, q and r are integers which may be the same or different and are either zero or 1. The sum of q and r is always at least 1.

A more preferred structure for a single radical formed by $R^3$ and $R^4$ is one having the formula

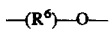

in which $R^6$ is $C_3-C_4$ divalent alkyl, substituted or unsubstituted. For instance, $R^6$ may have the formula —$CH_2$—$CH_2$—$CH_2$—$CH_2$—, preferably substituted. The radical can be substituted with hydroxy, polyhydroxy$(C_3$ alkyl), and substituted or unsubstituted alkanoamido groups, such as acetamido or hydroxyacetamido. The substituted structure will typically form a monosaccharide, preferably a sialic acid such as NeuAc or NeuGc linked α2,3 to the Gal residue.

In the general formula, above, both m and n are integers and can be either 3 or 4. Thus, in one set of structures Gal is linked β1,4 and Fuc is linked α1,3 to GlcNAc. This formula includes the SLe$^x$ tetrasaccharide. SLex has the formula NeuAcα2,3Galβ1,4(Fucα1,3)GlcNAcβ1—. The data presented below demonstrates that this structure is selectively recognized by LECCAM-bearing cells.

A related set of structures included in the general formula are those in which Gal is linked β1,3 and Fuc is linked α1,4. For instance, the tetrasaccharide, NeuAcα2,3Galβ1,3 (Fucα1,4)GlcNAcβ1—, termed here SLe$^a$, is recognized by selectin receptors. See, Berg et al. *J. Biol. Chem.*, 266:14869–14872 (1991). In particular, Berg et al. showed that cells transformed with E-Selectin cDNA selectively bound neoglycoproteins comprising SLe$^a$.

The term "alkyl" as used herein means a branched or unbranched, saturated or unsaturated, monovalent or divalent, hydrocarbon radical having from 1 to 20 carbons, including lower alkyls of 1–8 carbons such as methyl, ethyl, n-propyl, butyl, n-hexyl, and the like, cycloalkyls (3–7 carbons), cycloalkylmethyls (4–8 carbons), and arylalkyls.

The term "aryl" refers to a radical derived from an aromatic hydrocarbon by the removal of one atom, e.g., phenyl from benzene. The aromatic hydrocarbon may have more than one unsaturated carbon ring, e.g., naphthyl.

The term "alkoxy" refers to alkyl radicals attached to the remainder of the molecule by an oxygen, e.g., ethoxy, methoxy, or n-propoxy.

The term "alkylthio" refers to alkyl radicals attached to the remainder of the molecule by a sulfur.

An "alkanoamido" radical has the general formula —NH—CO—$(C_1-C_6$ alkyl) and may or may not be substituted. If substituted, the substituent is typically hydroxyl. The term specifically includes two preferred structures, acetamido, —NH—CO—$CH_3$, and hydroxyacetamido, —NH—CO—$CH_2$—OH.

The term "heterocyclic compounds" refers to ring compounds having three or more atoms in which at least one of the atoms is other than carbon (e.g., N, O, S, Se, P, or As). Examples of such compounds include furans (including the furanose form of pentoses, such as fucose), pyrans (including the pyranose form of hexoses, such as glucose and galactose) pyrimidines, purines, pyrazines and the like.

The term "oligo" refers to a polymeric molecule consisting of 2 to approximately 10 residues, for example, amino acids (oligopeptide), monosaccharides(oligosaccharide), and nucleic acids (oligonucleotide). The term "poly" refers to a polymeric molecule comprising greater than about 10 residues.

The sialic acid residue in the structures described above may be in different forms, so long as selectin binding is not significantly affected. Typically, the sialic acid is 5-N-acetylneuraminic acid, (NeuAc) or 5-N-glcolylneuraminic acid (NeuGc). Other sialic acids may be used in their place, however. For a review of different forms of sialic acid suitable in the present invention see generally, R. Schauer, *Methods in Enzymology*, 50: 64–89 (1987), and Schaur, *Advances in Carbohydrate Chemistry and Biochemistry*, 40: 131–234; both of which are incorporated by reference. As demonstrated in Example IX, below, the affinity for selectin receptors is the same if the oligosaccharide terminates in NeuAc or NeuGc. The term "SLe*" as used herein refers to the minimal tetrasaccharide unit, NeuAcα2,3Galβ1,4 (Fucα1,3)GlcNAcβ1,3—. The skilled artisan, however, will appreciate that the NeuAc may replaced by NeuGc or other equivalent forms of sialic acid. Structures illustrated herein which show the sialic acid residue as NeuAc are understood to include these other forms, in particular NeuGc.

Having identified carbohydrate ligands that mediate leukocyte-endothelial and leukocyte-platelet cell adhesion, compounds comprising SLe* and related structures can be purified or synthesized de novo. As detailed below, the present invention provides a variety of compounds comprising the selectin-binding moieties of the present invention. For instance, biomolecules can be used as the moiety-bearing compound. Biomolecules as defined here include but are not limited to biologically significant molecules such as amino acids (and their mimetics), oligopeptides, proteins (e.g., glycoproteins and protein hormones), fatty acids, lipids (e.g., glycolipids, phospholipids, sphingolipids and gangliosides), steroid hormones, oligosaccharides, polysaccharides, and nucleic acids (e.g., deoxyribonucleic acids and ribonucleic acids). These compounds can be purified and/or synthesized according to standard techniques known to the skilled artisan. In addition, a wide variety of compounds bearing the moiety may be synthesized de novo as described below.

All the compounds mentioned above can be used for a variety of purposes, including, for example, competitive inhibition of the binding of SLe*-bearing cells to cells that express the selectin receptors. By binding of the compounds of the invention to a cell surface selectin, interaction of the selectin with the native SLe* ligand on migrating cells will be prevented, interfering with normal and pathological binding of leukocytes and other cells to the endothelium or platelets. Thus, compounds that contain one or more selectin-binding moieties can serve as effective inhibitors of, for instance, inflammation, atherosclerosis, clotting and other endothelial or platelet-mediated pathologies.

Figure 12A:
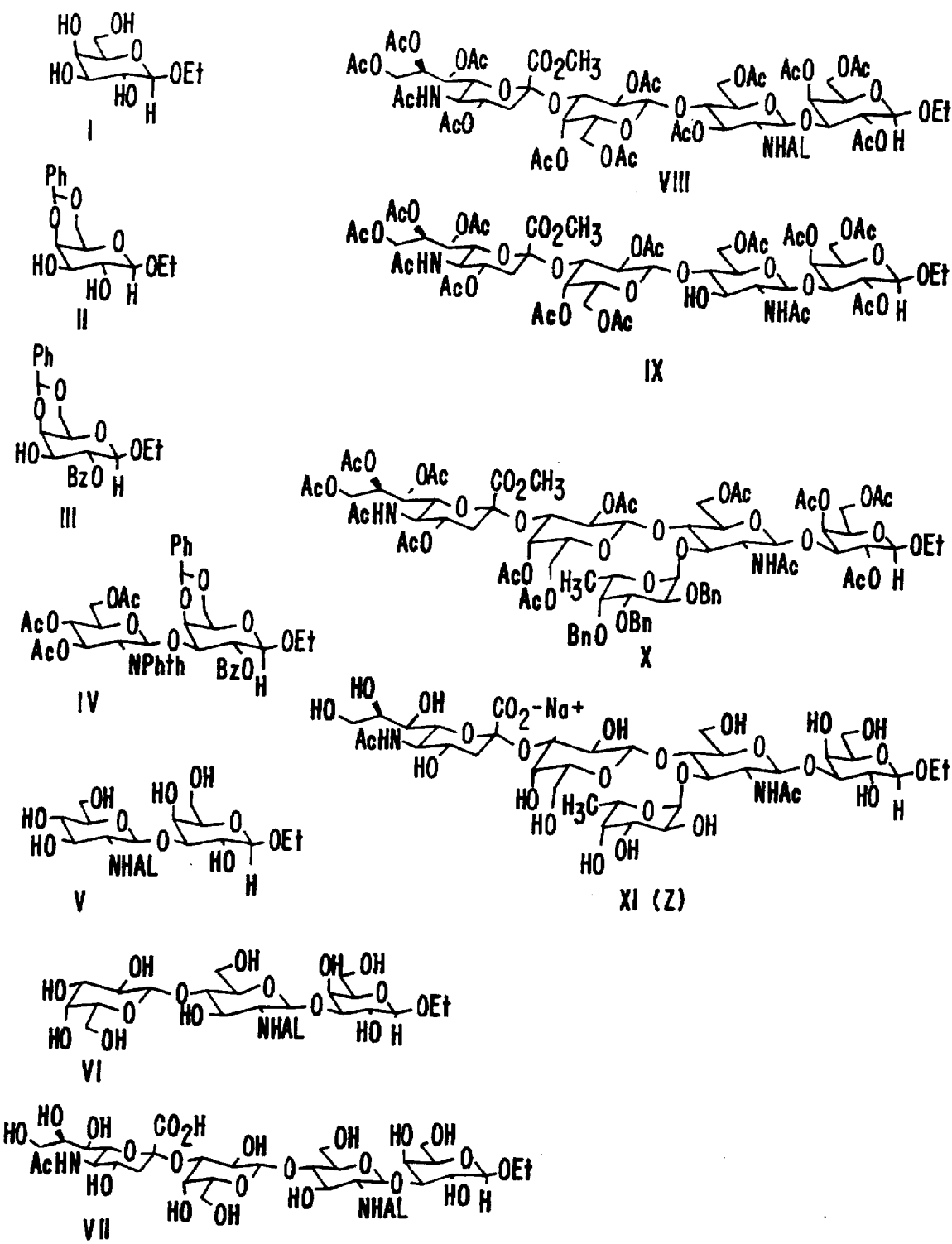
FIGS. 12A and 12B show intermediate compounds in the synthesis of Z (12A) and structure of related analogs (12B).
Figure 12B:
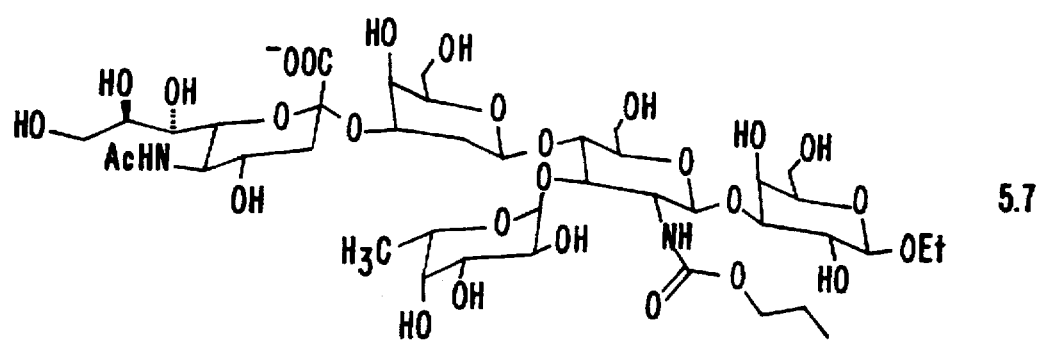
Figure 3:
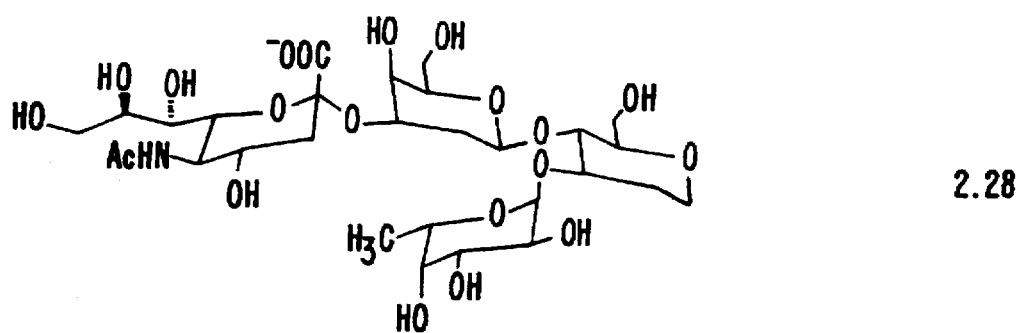

Evidence provided below shows that a pentasaccharide comprising the formula:

NeuAcα2,3Galβ1,4(Fucα1,3)GlcNAcβ1,3Galβ- is a minimal structure having substantially more inhibitory effect than the tetrasaccharide. A preferred pentasaccharide is Z (NeuAcα2,3Galβ1,4(Fucα1,3)GlcNAcβ1,3Galβ-OCH₂CH₃). Other preferred oligosaccharides are shown in FIG. 12B.

Other variations on the basic SLe* unit are also recognized by selectin receptors. For instance, evidence provided in Example VIII, below, shows that an oligosaccharide moiety, termed SY2 (also known as the VIM-2 antigen), having the structure NeuGcα2,3Galβ1,4GlcNAcβ1,3Galβ1,4(Fucα1,3) GlcNAcβ1,3Galβ1,4Glcβ binds selectin receptors equally as well as SLe*. Thus, oligosaccharides recognized by selectin receptors may comprise a number of the sialylated N-acetyllactosamine units, at least one of which is fucosylated (see, Teimeyer et al., *Proc. Natl. Acad. Sci. (USA)* 88:1138–1142 (1991), which is incorporated herein by reference).

The oligosaccharide moiety of the present invention preferably terminates in a sialic acid residue. In certain embodiments the sialic acid residue can be further linked to other saccharide residues, such as a second sialic acid in an α2,8 linkage.

Alternatively, the terminal sialic acid residue may be replaced by a variety of radicals. Thus, certain selectin binding moieties of the present invention have the general formula:

R¹-NeuAcα2,3Galβ1,4GlcNAcβ1-, wherein R¹ is R²R³C(CO₂H)—, wherein R² and R³ are the same or different and are H, lower alkyl (C1–C8), hydroxyl lower alkyl (C1–C8), arylalkyl, alkoxylalkyl. In addition, R² and R³ may be connected to form a 4–8 membered carbocyclic or heterocyclic ring.

Compounds containing SLe* and related structures can be obtained from the cell surface glycoproteins or glycolipids from a number of cells. For instance, the SLe* antigen is present on N-linked carbohydrate groups of the cell surface glycoproteins of LEC11 cells, a glycosylation mutant of chinese hamster ovary (CHO) cells. LEC11 expresses this unique glycopeptide which contains a terminal structure bearing both sialic acid and fucose in the SLe* sequence:

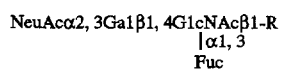

where R is:

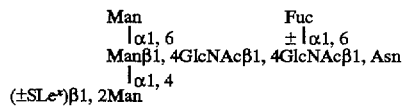

(See, Stanley et al., *J. Biol. Chem.*, 263:11374 (1988), which is incorporated herein by reference.) Using the procedure described below, it was demonstrated that the LEC11 mutant bound to activated human vascular endothelial cells. Neither wild type CHO cells nor other related glycosylation mutant CHO cell lines without the particular glycosylation pattern (SLe*) showed the same level of binding.

Other sources that can be used to obtain the SLe* unit include any cell that naturally expresses the moiety on glycolipid or glycoprotein carbohydrate groups. Thus, polymorphonuclear neutrophils, lymphocytes, tumor cells or HL-60 cells have been used to purify this unit. Other cells that bind to activated vascular endothelium can also be used as a source from which the ligand may be isolated (see, Symington et al., *J. Immunol.* 134:2498–2506 (1985), Mizoguchi et al., *J. Biol. Chem.* 259:11949–11957 (1984), Mizoguchi et al., *J. Biol. Chem.* 259:11943–11948 (1984), Paietta et al., *Cancer Res.* 48:280–287 (1988), all of which are incorporated herein by reference).

Compounds containing SLe* or its mimetics can be prepared from natural sources using methods well known in the art for isolating surface glycoproteins, glycopeptides, oligosaccharides and glycolipids from cells (See, e.g., Gerard, "Purification of glycoproteins" and Thomas et al., "Purification of membrane proteins," both in *Guide to Protein Purification*, Vol. 182, Methods in Enzymology (Deutscher ed., 1990), which is incorporated herein by reference). For example, LEC11 cells can be used to obtain glycoprotein or glycolipid that contains the SLe* unit using, for instance, the method described in Stanley et al., supra. Briefly, LEC11 cells are infected with vesicular stomatitis virus. The structural carbohydrate alterations exhibited by LEC11 are then expressed on the N-linked biantennary carbohydrates of the G glycoprotein of the virus. The virus is purified by equilibrium gradient centrifugation, and glycopeptides are purified using proteinase digestion as described by Stanley et al.

Several approaches are used to isolate a selectin-binding moiety from HL-60, HT-29, colo 205, neutrophils, and other cell lines which contain a ligand recognized by selecting. Since the ligand is generally expressed on the cell surface of these cell types, one approach consists of isolating a plasma membrane fraction enriched in the ligand. Once plasma membranes have been isolated, the ligands may be isolated and subsequently identified using monoclonal antibodies, particularly those which are reactive with the SLe$^x$ oligosaccharide and related structures, such as monoclonal antibodies FH6, SNH3 and CSLEX-1.

To characterize a selectin ligand on a glycoprotein, release of the oligosaccharide is generally the first step in the structural analysis of the oligosaccharide chain. This is accomplished by chemical cleavage of the protein-carbohydrate linkage, or by specifically releasing the oligosaccharide with endoglycosidases. In most cases, different procedures may be used to establish the correct conditions for an individual glycoprotein. Asparagine-linked oligosaccharides are released by hydrazinolysis, endoglycosidases, vigorous alkaline hydrolysis, and trifluoroacetolysis. O-linked carbohydrate units are typically released by alkaline β-elimination. The oligosaccharides are separated from the glycopeptides by gel filtration. The resulting oligosaccharides are then separated from each other using a combination of gel filtration, HPLC, thin layer chromatography, and ion exchange chromatography. The isolated oligosaccharides are then fully analyzed. Complete structural analysis of the purified oligosaccharide units requires the determination of the monosaccharide units, their ring form, configuration (D or L), anomeric linkage (α or β), the positions of the linkages between the sugars, and their sequence. In addition, the position of any substituent groups are established. Methylation analysis is used to determine the positions of the glycosidic linkages between the monosaccharides. The anomeric configuration of the sugar residues can be addressed using 500-MHz 1H NMR spectroscopy. The conditions and methods used to perform a complete structural carbohydrate analysis are described generally in Beeley, *Laboratory Techniques in Biochemistry and Molecular Biology*, eds. Burdon and Knippenberg, Elsevier, Amsterdam (1985), incorporated herein by reference.

The state of the art techniques to fully characterize the sugars of an oligosaccharide include the use of several analytical techniques such as FAB-MS (fast atom bombardment-mass spectrometry), HPAE (high pH anion exchange chromatography) and $^1$H-NMR. These techniques are complementary. Recent examples of how these techniques are used to fully characterize the structure of an oligosaccharide can be found in the analysis by Spellman et al., *J. Biol. Chem.* 264:14100 (1989), and Stanley et al., supra. Other methods include positive ion fast atom bombardment mass spectroscopy (FAB-MS) and methylation analysis by gas chromatography—electron impact mass spectroscopy (GC/EI-MS) (see, EPO Application No. 89305153.2, which is incorporated herein by reference).

One approach to characterizing the selectin ligand on glycolipids consists of disrupting the cells using organic solvents, isolating the glycolipids, and identifying those glycolipids reactive with monoclonal antibodies to SLe$^x$, such as FH6, SNH3, SNH4, CSLEX-1, or VIM-2, for example, and then determining the structure of the oligosaccharide chains. To obtain glycolipids, including gangliosides which contain SLe$^x$, standard methods for glycolipid preparation can be used (see, e.g., Ledeen et al., *J. Neurochem.* 21:829 (1973), which is incorporated herein by reference). For example, glycolipids are extracted from HL-60, HT-29, PMNs, human leukocytes, and other cell lines expressing the selectin ligand by methods generally known to those skilled in the arts (see, e.g., Symington et al., *J. Immunol.* 134:2498 (1985) and Macher and Beckstead, *Leukemia Res.* 14:119–130 (1990), which are incorporated herein by reference). Cells are grown in suspension and are harvested by centrifugation. Glycolipids are extracted from the cell pellet with chloroform/methanol (2:1) and isopropyl alcohol/hexane/water (55:25:20) as described by Kannagi et al., *J. Biol. Chem.* 257:14865 (1982), which is incorporated herein by reference. The resulting extracts are partitioned by a chloroform/methanol/water (3:2:1) Folch partition. The resulting upper phase of the extraction contains gangliosides (glycosphingolipids that contain at least one sialic acid moiety) and the lower phase contains other glycolipids.

The gangliosides contained in the upper phase are isolated and further purified into neutral and acidic fractions using DEAE-Sephadex chromatography as described in detail by Ledeen and Yu, *Methods Enzymol.* 83:139 (1982), which is incorporated herein by reference. The purified gangliosides are pooled, lyophilized, and dissolved in chloroform/methanol (2:1).

The lower phase of the Folch partition contains other glycolipids. These are isolated and separated on preparative thin-layer chromatography using chloroform/methanol/water (60:35:8) as the solvent system, as described by Symington.

To identify those gangliosides and other glycolipids that contain a selectin ligand, immunochemical glycolipid analysis is performed according to the procedure of Magnani et al., *Anal. Biochem.* 109:399 (1980), which is incorporated herein by reference. Briefly, the ganglioside pool described above is chromatographed by thin layer chromatography. The thin layer plate is then incubated with $^{125}$I labeled CSLEX-1, or other monoclonal antibody that binds specifically to SLe$^x$ or related structures. Following incubation with the labeled antibody, the plate is exposed to radiographic detection film and developed. Black spots on the X-ray film correspond to gangliosides that bind to the monoclonal antibody, and those gangliosides are recovered by scraping the corresponding areas of the silica plate and eluting the gangliosides with chloroform/methanol/water. Glycolipids are also dried and resuspended in chloroform and developed in a similar thin layer system and probed with the radiolabeled antibody. Structural analysis of oligosaccharides derived from glycolipids is performed essentially as described for glycoproteins.

Oligosaccharides comprising the SLe$^x$ unit can be prepared from glycoproteins by methods well known in the art (see, e.g., Gerard, supra, at pp. 537–539). Typically, N-glycosidase F (N-glycanase) is used to cleave N-linked oligosaccharides while O-linked groups are cleaved with endo-N-acetylgalactosaminidase.

Synthetic compounds containing SLe$^x$ or its mimetics can, depending on the particular use desired, be prepared attached to a variety of moieties. For example, SLe$^x$ can be converted to a ganglioside by linking a ceramide moiety to the C-1 of the reducing terminal GlcNAc unit. SLe$^x$ structures and related structures can also be linked to a wide variety of other moieties such as variously substituted amino groups, heterocyclic compounds, ether linkages with branched or unbranched carbon chains, and ether linkages with aryl or alkylaryl moieties. The selectin-binding moiety may also be bound to various polysaccharides, amino acids, amino acid mimetics, oligopeptides or proteins using methods well known in the art.

For the synthesis of polyvalent forms of selectin-binding moieties, monomeric units containing SLe$^x$ or other structures can be joined to form molecules having one to about four or more selectin-binding moieties. An example of such a polyvalent form is one in which the units are linked by the following linking moieties:

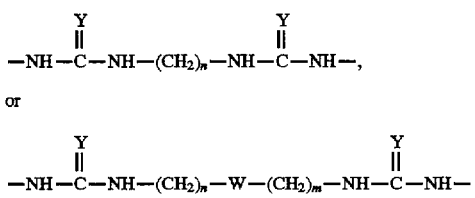

or

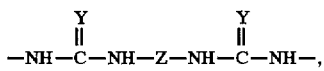

wherein, n and m are the same or different and are integers from 2 to 12; Y is O or S; and W is O, S, or NH.

Alternatively, the linking moeity has the formula:

$$-NH-\overset{Y}{\overset{\|}{C}}-NH-Z-NH-\overset{Y}{\overset{\|}{C}}-NH-,$$

wherein, Z is a 5- to 14-membered ring and the substituents on the ring are in a cis- or trans-relationship. Y may be O or S.

SLe$^x$ and related structures may also be attached to various heterocyclic compounds (e.g., one containing one or more nitrogen atoms). In this case, the SLe$^x$ moieties are preferably linked to the nitrogen atoms on the ring, each nitrogen being linked to one SLe$^x$ moiety. Examples of heterocyclic compounds that are suitable for this purpose include piperazine and homopiperazine.

Alternatively, polyvalent forms of SLe$^x$ or its mimetics can be created by attaching the desired moiety to preformed carrier moieties that have multiple sites of attachment. Examples include attachment of SLe$^x$ to the amino groups of lysine and lysine-containing peptides, proteins, glycoproteins or to the asparagine side-chain of such compounds.

Another method of preparing polyvalent selectin-binding binding compounds is by addition of desired monosaccharide residues to polysaccharides. For instance, a polysaccharide that contains a repeat unit having the linear core structure of SLe$^x$ (i.e., without the fucose residue) may be converted into a polyvalent SLe$^x$ containing polysaccharide by enzymatic fucosylation. Native polysaccharide types Ia, II, or III obtained from Group B Streptococcus are preferably used for this purpose. These polysaccharides can be isolated according to standard procedures from cell lines deposited with the American Type Culture Collection (Type Ia from ATCC Nos. 12400 and 31574; Type II from ATCC Nos. 12973 and 31576; and Type III from ATCC No. 31577). See e.g., Jennings et al., Biochem. 22 1258–1263 (1983) and PCT Application, Publication No. 8706267, both of which are incorporated herein by reference.

These polysaccharides comprises repeat units having the formulas:

Type Ia

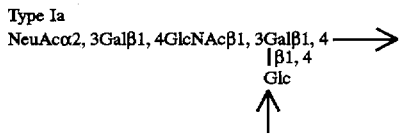

Type II

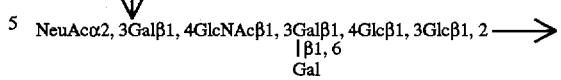

Type III

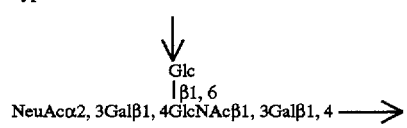

The arrows in the above structures identify the backbone in each polysaccharide molecule. As can be seen, type Ia polysaccharides contain a repeat unit having side chain which corresponds to the SLe$^x$ linear core structure. The other two polysaccharides, the backbone includes part of the SLe$^x$ core structure. Enzymatic Fucosylation of these polysaccharides using an α1,3 fucosyltransferase according to standard techniques described below yields a polyvalent SLe$^x$ compound. After fucosylation, the repeat units have the following formulas:

Type Ia

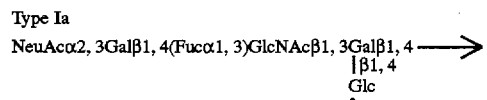

Type II

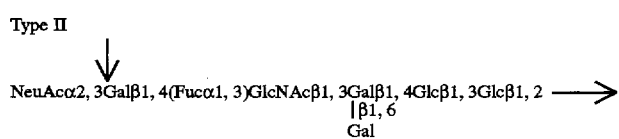

Type III

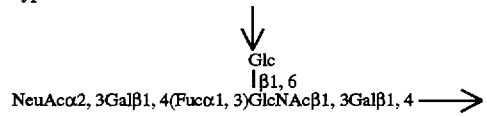

The entire polysaccharide can be used for this purpose, as can fragments thereof. Thus, polysaccharides having a molecular weight between about 5,000 and about 300,000 can be used. A molecular weight between about 25,000 and about 100,000 is preferred. Any number of side chains on the polysaccharide type Ia may be fucosylated for the polysaccharide to have activity. Typically, between about 5 and about 200 side chains are fucosylated, preferably between about 50 and about 150 are fucosylated.

The synthesis of the selectin-binding moiety can be accomplished using chemical, enzymatic, or combined chemical and enzymatic strategies. (see, e.g., EPO Publication No. 319,253, which is incorporated herein by reference.) In a preferred method (Scheme I below), a compound containing one or more N-acetylglucosamine units (GlcNAc-R) can be reacted sequentially with a galactosyltransferase (N-acetylglucosamine β1,4 galactosyltransferase (E.C. 2.4.1.90)), a sialyltransferase (Galβ1,4GlcNAc α2,3 sialyltransferase (E.C. 2.4.99.6) or Galβ1,3GalNAc α2,3 sialytransferase (E.C. 2.4.99.4)) and a fucosyltransferase (N-acetylglucosaminide α1,3 fucosyltransferase (E.C. 2.4.1.152)) to yield the final SLe$^x$-containing structures. In this case, R may be a carrier moiety or an activatable intermediate that will allow attachment to a suitable carrier moiety. Each enzymatic reaction uses the appropriate nucleotide sugar as a donor substrate to generate the following intermediates in the synthesis of SLe$^x$. The glycosyl transfer reactions may optimally be carried out with added alkaline phosphatase (e.g., from calf intestine, CIAP) to consume the nucleoside phosphate byproduct which may inhibit the reaction.

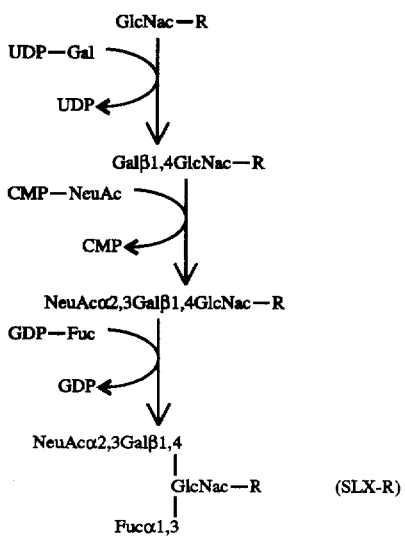

Scheme I

The general conditions for preparative enzymatic synthesis of carbohydrate groups analogous to SLe$^x$ are known (see, e., Toone et al., *Tetrahedron* 45:5365–5422 (1989); Wong et al., *J. Am. Chem. Soc.* 104: 3542–3544 (1982); Unverzagt et al., *J. Am. Chem. Soc.* 112:9308–9309 (1990); Prieels et al., *J. Biol. Chem.* 256:10456–10463 (1981), all of which are incorporated herein by reference). Each of the key enzymatic reactions has been demonstrated (Beyer et al., *Adv. Enzymol.* 52:23–176 (1981); Toone et al., supra; and Howard et al., *J. Biol. Chem.* 262:16830–16837 (1981); all of which are incorporated herein by reference). For preparative reactions, the galactosyltransferase and the sialyltransferase(s) are purified from natural sources (Beyer et al., supra, and Weinstein et al., *J. Biol. Chem.* 257:13835–13844 (1982), which are incorporated herein by reference). Fucosyltransferases may also be purified from natural sources, as generally described in Crawley and Hindsgaul, *Carbohyd. Res.* 193:249–256 (1989), incorporated by reference herein. The cDNAs of the galactosyltransferase and a sialyltransferase have been cloned (Paulson and Colley, *J. Biol. Chem.* 264:17615–17618 (1989), which is incorporated herein by reference), allowing the production of soluble recombinant enzymes for large-scale preparative synthesis (Colley et al., *J. Biol. Chem.* 264:17619–17622 (1989)).

To obtain sufficient amounts of fucosyltransferase for large-scale reaction, the gene or cDNA that codes for the enzyme can be cloned and expressed as a recombinant soluble enzyme by someone with ordinary skill in the art. As a preferred method RNA can be extracted from the wild type CHO cells and LEC11 cells as described by Chirgwin et al., *Biochemistry* 18:5214–5299 (1979), and the poly A+ RNA isolated by chromatography on oligo(dT)-cellulose. Next, cDNA from the LEC-11 cells can be prepared as described by Sambrook et al., *Molecular Cloning: A Laboratory Manual*, 2nd Ed. (1989), Cold Spring Harbor Press, New York, which is incorporated herein by reference. The cDNAs that are common to both LEC11 and CHO cells can be subtracted using the method of Davis (*Handbook of Experimental Immunology*, Vol. 2, pp. 1–13 (1986)) using excess poly A+ RNA from wild type CHO cells, which do not express the desired fucosyltransferase, but otherwise have most of the MRNA species of LEC11 cells. A cDNA library can then be constructed in the CDM8 expression vector using the cDNA that was not subtracted (Seed, *Nature* 329:840–842 (1987)). Clones expressing the fucosyltransferase can be isolated using the expression cloning method described by Larsen et al., *Proc. Natl. Acad. Sci.* 86:8227–8231 (1989), employing transfection of COS-1 cells and screening for cells expressing the SLe$^x$ antigen with the CSLEX antibody or other antibody that is specific for the SLe$^x$ antigen. The full-length clone of the fucosyltransferase can then be used to produce a soluble recombinant enzyme as taught by Colley et al., supra.

Another source of SLe$^x$ is the plasma protein α$_1$-acid glycoprotein, the carbohydrate moieties of which can be fucosylated to produce SLe$^x$ (see, *Alpha$_1$-Acid glycoprotein: Genetics, Biochemistry, Physiological Functions, and Pharmacolory*, Bauman et al. ed. (Wiley 1989), and Walz, et al. *Science* 250:1132–1135 (1990), both of which are incorporated herein by reference).

Although enzymatic or combined chemical and enzymatic synthesis of SLe$^x$ compounds are preferred, chemical synthesis is also possible, as shown in Schemes II and IIa below.

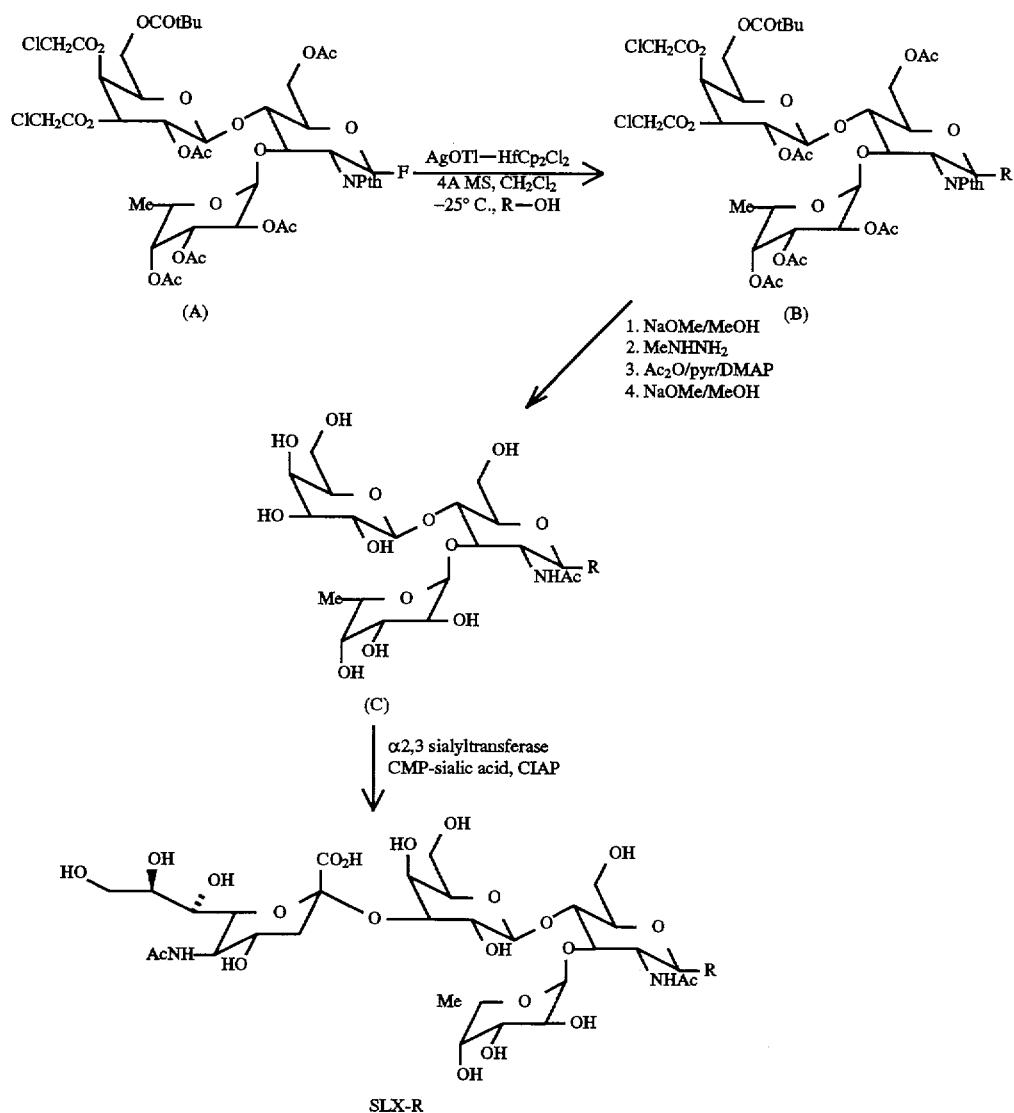
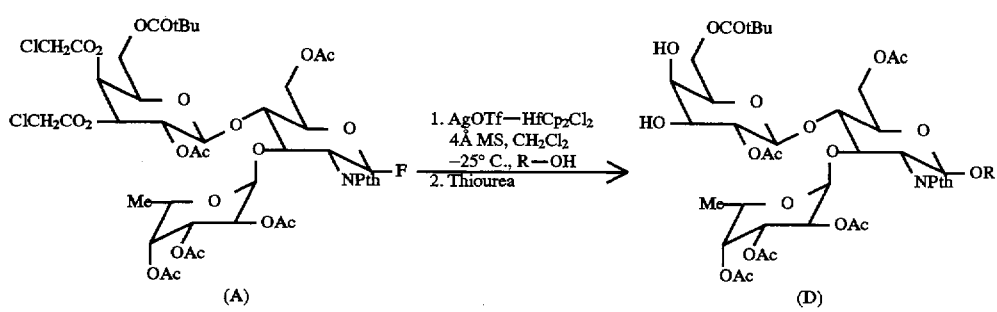

-continued
Scheme IIa

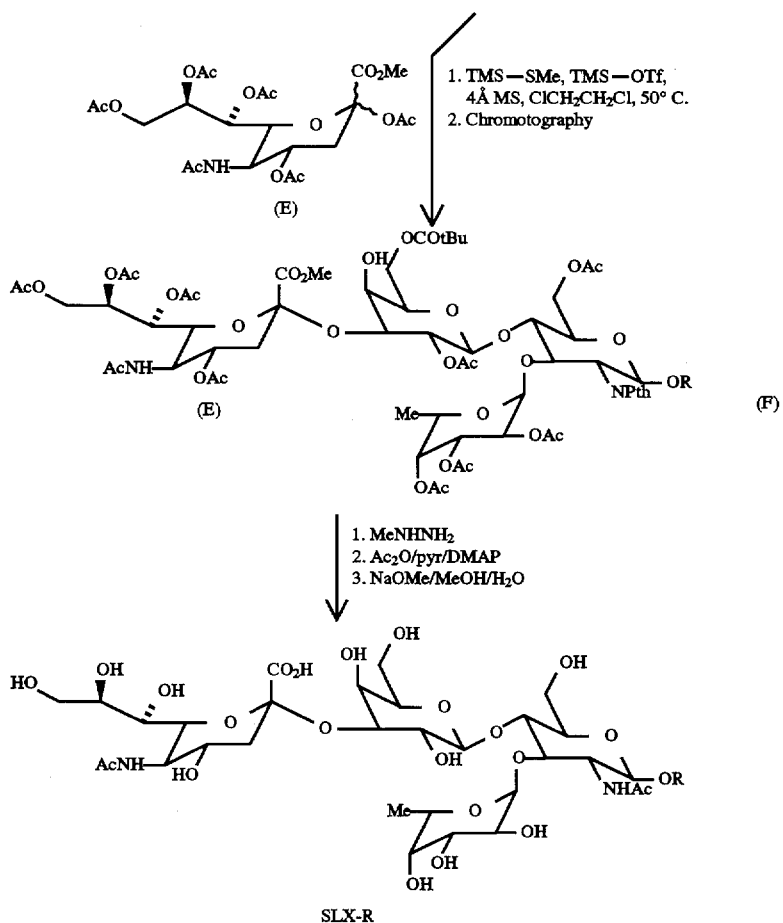

Component pieces of the SLe$^x$ structure have been synthesized. For instance, the preparation of sialic acid-containing glycosides, including SLe$^x$, is disclosed in European Patent Application No. 88311312.8, which is incorporated herein by reference. Nicolaou, et al., (J. Amer. Chem. Soc. 112:3693 (1990)) have published the total synthesis of the tumor-associated Lex family of glycosphingolipids. Therein is described the synthesis of the protected trisaccharide Galβ1,4(Fucα1,3)GlcNAc (A) as illustrated in Scheme II. Reaction of this intermediate with an appropriate glycosyl acceptor (e.g., an alcohol moiety) results in compound (B). Selective deprotection and acetylation of the glucosamine moiety are carried out essentially as described in Nicolaou, et al. to afford compound (C). Reaction of (C) with a sialyltransferase as described above furnishes the desired product SLe$^x$-R, although this may be produced in relatively low yield using Scheme II.

Modified fucosides may be included in the synthetic schemes to provide for SLe$^x$ analogues which vary in this moiety. For example, α-D-arabinosyl glycosides may be synthesized following known procedures, Nicolaou et al., J. Amer. Chem. Soc. 112:3693–3695 (1990) through the use of tri-O-benzyl arabinosyl halides. Other C-5 aryl or alkyl substituted arabinosyl moieties may be synthesized (Danishefsky et al., J. Amer. Chem. Soc. 107:1274 (1985), Danishefsky, Aldrichimica Acta. 19:59–68 (1986) and references therein), and introduced into the disaccharide in the same manner. All of these references are incorporated herein by reference.

According to alternative Scheme IIa, the trisaccharide (A) is partially deprotected to furnish (D), which is subsequently reacted with the peracetylated sialic acid methyl ester (E) following a procedure described by Kameyama et al., XV Intl. Carbohyd. Symp., Abst. No. A096, (1990), and Carbohydrate Res., 209:c1–c4 (1991) (which are incorporated herein by reference), yielding (F) after chromatographic purification. Treatment of (F) with with methylhydrazine, followed by N-acetylation, O-deacetylation and ester hydrolysis, furnishes SLe$^x$-R.

Preferred examples of R for scheme II and IIa include alkyl (straight chain, branched, saturated, mono- and poly-unsaturated); serine (D or L); serine containing peptides; di- and tri-alkanolamines (e.g. [HO(CH$_2$)$_n$]$_2$NH, [HO(CH$_2$)$_n$]$_3$N; wherein n=2 to 20, and the carbon chain is a straight chain, or is branched, unsaturated, or mono- or poly-unsaturated). R can also be aryl, substituted aryl (e.g., Me, OH, I; alone or in combination including $^{125}$I), alkylaryl, arylalkyl or other moiety, as the skilled artisan would include for the desired use. The introduction of iodine into phenolic compounds such as tyrosine is known in the art. Radical groups containing phenols are useful for the introduction of $^{125}$I radioisotope, yielding compounds that are useful in diagnosis.

Compounds comprising SLe$^x$ and related structures may also be used to assay for the presence of other compounds that are capable of inhibiting intercellular adhesion mediated by selectins. A number of methods can be used to assay the biological activity of test compounds for the ability to inhibit the selectin-mediated response. Ideally, the assays of the present invention allow large scale in vitro or in vivo screening of a variety of compounds.

The agent or test compound to be screened will typically be a synthetic or naturally-produced biomolecule, such as a peptide, polypeptide, protein (e.g., monoclonal antibody), carbohydrate (e.g., oligosaccharide), glycoconjugate, nucleic acid, and the like. The compounds are synthetically produced using, for instance, the methods for synthesizing oligosaccharides described above (see, also, Khadem, *Carbohydrate Chemistry* (Academic Press, San Diego, Calif., 1988), which is incorporated herein by reference). Methods for synthesizing polypeptides of defined composition are well known in the art (see, Atherton et al. *Solid Phase Peptide Synthesis* (IRL Press, Oxford, 1989) which is incorporated herein by reference). If the synthetic test compounds are polymeric (e.g., polypeptides or polysaccharides) they are preferably altered in a systematic way to identify the sequence of monomers which have the desired effect (see, e.g., U.S. Pat. No. 4,833,092, which is incorporated herein by reference). Test compounds may also be isolated from any natural source, such as animal, plant, fungal, or bacterial cells in accordance with standard procedures as described above. Potentially useful monoclonal antibodies can be prepared according to standard methods described in more detail, below.

The assays of the present invention are particularly useful in identifying compounds that act as antagonists or agonists of a ligand molecule. Antagonists are compounds which reverse the physiological effect of a ligand or exclude binding of the ligand to the receptor. An antagonist usually competes directly or indirectly with the ligand for the receptor binding site and, thus, reduces the proportion of ligand molecules bound to the receptor. Typically, an antagonist will be the topographical equivalent of the natural ligand and will compete directly with the ligand for the binding site on the selectin. Such a compound is referred to here as a "mimetic." An $SLe^x$ mimetic is a molecule that conformationally and functionally serves as substitute for an $SLe^x$ moiety in that it is recognized by a selectin receptor. Alternatively, if the ligand and the test compound can bind the receptor simultaneously, the compound may act non-competitively. A non-competitive inhibitor acts by decreasing or inhibiting the subsequent physiological effects of receptor-ligand interactions rather than by diminishing the proportion of ligand molecules bound to the receptor. Finally, the assays of the present invention can be used to identify synthetic or naturally occurring agonists, that is, compounds which bind the receptor and initiate a physiological response similar to that of the natural ligand.

Numerous direct and indirect methods for in vitro screening of inhibitors of ligand-receptor interactions are available and known to those skilled in the art. For instance, the ability to inhibit adhesion of $SLe^x$-bearing cells to cells displaying a particular selectin can be determined. As discussed above, selectin receptor genes have been cloned, thus the genes can be inserted and expressed in a wide variety of cells, such as COS cells, CHO cells and the like. In addition, cells that do not normally express $SLe^x$ are capable of being transformed with one or more glycosyltransferase genes which confer on the transformed cells the ability to synthesize the ligand. (see, e.g., Lowe et al., *Cell* 63:475–484 (1990), which is incorporated herein by reference.) Typically, the test compound or agent is incubated with labelled $SLe^x$-bearing cells and activated endothelial cells immobilized on a solid surface. Inhibition of cellular adhesion is then determined by detecting label bound to the surface after appropriate washes. In an exemplified assay described below, promyelocytic HL-60 cells and activated human endothelial cells or activated platelets are used.

Since a ligand specific for selectin receptors has now been identified, isolated ligand molecules can also be used in the assays. The terms "isolated selectin-binding agent" or "isolated $SLe^x$ moiety" as used herein refer to a selectin binding compound that is in other than its native state, e.g., is not associated with the cell membrane of a cell that normally expresses the ligand. Thus, an isolated $SLe^x$ moiety may be a component of an isolated molecule, such as an oligosaccharide or a glycoconjugate. The isolated molecule may be synthesized or prepared from the membranes of $SLe^x$-bearing cells. Alternatively, the isolated selectin-binding agent or $SLe^x$ moiety may be associated with a liposome or attached to a solid surface before use in the assay. Methods for preparing selectin-binding liposomes and for immobilizing various biomolecules are extensively discussed below.

Typically, the in vitro assays of the present invention are competition assays which detect the ability of a test compound to competitively inhibit binding of a compound known to bind either the receptor or the ligand. Inhibition of binding between $SLe^x$ and a selectin receptor is usually tested. Inhibition of other binding interactions are also suitable, for instance, inhibition of the binding between a monoclonal antibody (e.g., CSLEX-1) and $SLe^x$ or between an $SLe^x$ mimetic and a selectin receptor can be used. Numerous types of competitive assays are known (see, e.g., U.S. Pat. Nos. 3,376,110, 4,016,043, and Harlow and Lane, *Antibodies: A Laboratory Manual*, Cold Spring Harbor Publications, New York (1988), which are incorporated herein by reference).

The assays of the present invention are also suitable for measuring binding of a test compound to one component alone, rather than using a competition assay. For instance, immunoglobulins can be used to identify compounds that contain the $SLe^x$ moiety. Standard procedures for monoclonal antibody assays, such as ELISA, may be used (see, Harlow and Lane, supra). When assaying for glycolipids comprising the $SLe^x$ antigen, the reactivity of the monoclonal antibody with the antigen can be assayed by TLC immunostaining using the method originally described in Magnani et al., *Anal. Biochem.* 109:399–402 (1980) or by solid-phase radioimmunoassay as described by Kanagi et al., *Cancer Res.* 43:4997–5005 (1983); which are incorporated herein by reference. Glycoproteins can be assayed by standard immunoblotting procedures as described in Harlow and Lane, supra. Sandwich assay formats are also suitable (see, e.g., U.S. Pat. Nos. 4,642,285; 4,299,916; and 4,391,904; and Harlow and Lane, supra all of which are incorporated herein by reference). Typically, compounds that have been identified in a binding assay will be further tested to determine their ability to inhibit receptor-ligand interactions.

Other assay formats involve the detection of the presence or absence of various physiological changes in either ligand-bearing or selectin-bearing cells that result from the interaction. Examples of suitable assays include the measurement of changes in transcription activity induced by binding (see, e.g., EPO Publication No. 3712820), the detection of various cell mediated extra-cellular effects (see, e.g., PCT Publication No. 90/00503), and the detection of changes in the membrane potential of individual cells (see, e.g., U.S. Pat. No. 4,343,782), all of which are incorporated herein by reference. Alternatively, conformational changes in isolated receptors or ligands can be detected; see, e.g., U.S. Pat. No. 4,859,609, which is incorporated herein by reference.

Any component of the assay, including the ligand, the receptor, or the test compound, may be bound to a solid surface. Many methods for immobilizing biomolecules on solid surfaces are known in the art. For instance, the solid surface may be a membrane (e.g., nitrocellulose), a microtiter dish (e.g., PVC or polystyrene) or a bead. The desired component may be covalently bound or noncovalently attached through unspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials which may be employed, include paper, glasses, ceramics, metals, metalloids, semiconductive materials, cermets or the like. In addition are included substances that form gels, such as proteins, e.g., gelatins, lipopolysaccharides, silicates, agarose and polyacrylamides or polymers which form several aqueous phases, such as dextrans, polyalkylene glycols (alkylene of 2 to 3 carbon atoms) or surfactants e.g. amphiphilic compounds, such as phospholipids, long chain (12–24 carbon atoms) alkyl ammonium salts and the like. Where the solid surface is porous, various pore sizes may be employed depending upon the nature of the system.

In preparing the surface, a plurality of different materials may be employed, particularly as laminates, to obtain various properties. For example, protein coatings, such as gelatin can be employed to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, J. Biol. Chem. 245 3059 (1970) which is incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labelled assay components. Alternatively, the surface is designed such that it nonspecifically binds one component but does not significantly bind another. For example, a surface bearing a lectin such as concanavalin A will bind a carbohydrate-containing compound but not a labelled protein that lacks glycosylation. Various solid surfaces for use in noncovalent attachment of assay components are reviewed in U.S. Pat. Nos. 4,447,576 and 4,254,082, which are incorporated herein by reference.

Many assay formats employ labelled assay components such as $SLe^x$ ligands, $SLe^x$ mimetics, immunoglobulins, receptors, or test compounds. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}P$ labelled compounds or the like. The choice of radioactive isotope depends on research preferences due to ease of synthesis, varying stability, strength of emission, and half lives of the selected isotopes. Other non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phoaphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various signal producing systems which may be used, see, U.S. Pat. No. 4,391,904, which is incorporated herein by reference.

As discussed above, in addition to various inhibitor compounds which comprise an accessible $SLe^x$ unit or $SLe^x$ mimetic, the present invention also provides monoclonal antibodies capable of inhibiting intercellular adhesion mediated by selectins as well as methods for identifying such antibodies. The monoclonal antibodies bind a selectin ligand or receptor and block cellular adhesion. Thus, the multitude of techniques available to those skilled in the art for production and manipulation of various immunoglobulin molecules can be applied to inhibit intercellular adhesion.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies, including for example, Fv, Fab, and F(ab)2, as well as in single chains (ecT., Huston et al., *Proc. Nat. Acad. Sci. U.S.A.* 85:5879–5883 (1988) and Bird et al., *Science* 242:423–426 (1988), which are incorporated herein by reference). (see, generally, Hood et al., *Immunology*, 2nd ed., Benjamin, N.Y. (1984), and Hunkapiller and Hood, *Nature* 323:15–16 (1986), which are incorporated herein by reference.)

Antibodies that bind the $SLe^x$ antigen may be produced by a variety of means. The production of non-human monoclonal antibodies, e.g., murine, lagomorpha, equine, etc., is well known and may be accomplished by, for example, immunizing the animal with the $SLe^x$ antigen or a preparation containing a glycoprotein or glycolipid linked to the $SLe^x$ antigen. Antibody-producing cells obtained from the immunized animals are immortalized and screened, or screened first for the production of antibody that inhibits the interaction of the viral surface protein with the receptor molecule and then immortalized. For a discussion of general procedures of monoclonal antibody production see Harlow and Lane, *Antibodies. A Laboratory Manual* (1988), supra.

The generation of human monoclonal antibodies to a human antigen (in the case of an $SLe^x$ unit isolated from human tissue) may be difficult with conventional techniques. Thus, it may be desirable to transfer the antigen binding regions of the non-human antibodies, e., the F(ab')2 or hypervariable regions, to human constant regions (Fc) or framework regions by recombinant DNA techniques to produce substantially human molecules. Such methods are generally known in the art and are described in, for example, U.S. Pat. Nos. 4,816,397, EP publications 173,494 and 239,400, which are incorporated herein by reference. Alternatively, one may isolate DNA sequences which encode a human monoclonal antibody or portions thereof that specifically bind to the human $SLe^x$ by screening a DNA library from human B cells according to the general protocol outlined by Huse et al., *Science* 246:1275–1281 (1989), incorporated herein by reference, and then cloning and amplifying the sequences that encode the antibody (or binding fragment) of the desired specificity.

A number of currently available monoclonal antibodies can be used according to the present invention to inhibit intercellular adhesion mediated by selecting. For instance, CSLEX-1 (see, Campbell et al., *J. Biol. Chem.* 259:11208–11214 (1984)), VIM-2, which recognizes a sequence slightly different from $SLe^x$ (see, Macher et al., supra), FH6 (described in U.S. Pat. No. 4,904,596) (all references are incorporated herein by reference) or SH3 and SH4 generated by Dr. S. Hakomori of the Biomembrane Institute in Seattle, Washington.

The compounds of the present invention, including immunoglobulins, can be used in preparing pharmaceutical formulations as discussed below. If the compound is an oligosaccharide or glycoconjugate, the $SLe^x$ or $SLe^x$-mimetic moiety can be presented in a variety of forms, but should be able to effectively bind to a selectin receptor, such as E-Selectin, P-Selectin, or MEL-14 antigen and thereby inhibit intercellular adhesion.

The pharmaceutical compositions of the present invention can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Example of specific defense system reactions include antibody response to antigens such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of PMN leukocytes at sites of bacterial infection (e.g., pulmonary infiltrates in bacterial pneumonias and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, nephritis, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

By way of example, reperfusion injury is particularly amenable to treatment by compositions of the present invention. Compositions that inhibit a P-Selectin selectin-ligand interaction may be particularly useful for treating or preventing reperfusion injury. The present invention may be used prophylactically prior to heart surgery to enhance post-surgical recovery.

Because P-Selectin is stored in Weibel-Palade bodies of platelets and endothelial cells and is released upon activation by thrombin to mediate adhesion of neutrophils and monocytes, inhibitors of the P-Selectin -ligand interaction may be especially useful in minimizing tissue damage that often accompanies thrombotic disorders. For instance, such inhibitors may be of therapeutic value in patients who have recently experienced stroke, myocardial infarctions, deep vein thrombosis, pulmonary embolism, etc. The compounds are especially useful in pre-thrombolytic therapy.

Compositions of the invention find particular use in treating the secondary effects of septic shock or disseminated intravascular coagulation (DIC). Leukocyte emigration into tissues during septic shock or DIC often results in pathological tissue destruction. Furthermore, these patients may have widespread microcirculatory thrombi and diffuse inflammation. The therapeutic compositions provided herein inhibit leukocyte emigration at these sites and mitigate tissue damage.

The inhibitors of selectin-ligand interaction also are useful in treating traumatic shock and acute tissue injury associated therewith. Because the selectins play a role in recruitment of leukocytes to the sites of injury, particularly E-Selectin in cases of acute injury and inflammation, inhibitors thereof may be administered locally or systemically to control tissue damage associated with such injuries. Moreover, because such inhibitors are specific for sites of inflammation, e.g., sites where E-Selectin receptors are expressed, these compositions will be more effective and less likely to cause complications when compared to traditional anti-inflammatory agents.

Thus, the present invention also provides pharmaceutical compositions that can be used in treating the aforementioned conditions. The pharmaceutical compositions are comprised of biomolecules or other compounds which comprise an $SLe^x$ unit, antibodies which bind to $SLe^x$, or other compounds which inhibit the interaction between the $SLe^x$ ligand and selectin receptors, together with pharmaceutically effective carriers. A biomolecule of the present invention may be a peptide, polypeptide, protein (e.g., an immunoglobulin), carbohydrate (e.g., oligosaccharide or polysaccharide), glycoconjugate (e.g., glycolipid or glycoprotein), nucleic acid, and the like. The pharmaceutical compositions are suitable for use in a variety of drug delivery systems. For a brief review of present methods for drug delivery, see, Langer, *Science* 249:1527–1533 (1990), which is incorporated herein by reference.

In light of the complexity of the inflammatory response in mammals, one of skill will readily recognize that the pharmaceutical compositions of the present invention may comprise $SLe^x$ bearing compounds in admixture with other compounds known to interfere with the function of cellular adhesion molecules. For instance, members of the integrin family of adhesion molecules are thought to play a role in the extravasation of leukocytes at points of infection. For a review of intercellular adhesion receptors, including selectin receptors, and their role immune function, see Springer, *Nature* 346:425–434 (1990), which is incorporated herein by reference. In addition, successful treatment using the pharmaceutical compositions of the present invention may also be determined by the state of development of the condition to be treated. Since different adhesion molecules may be up or down regulated in response to a variety of factors during the course of the disease or condition, one of skill will recognize that different pharmaceutical compositions may be required for treatment of different inflammatory states.

In one embodiment, the $SLe^x$ ligand of the pharmaceutical composition can be used to target conventional anti-inflammatory drugs or other agents to specific sites of tissue injury. By using a selectin-binding moiety such as an $SLe^x$ ligand or $SLe^x$ mimetic to target a drug to a selectin receptor on, e.g., a vascular endothelial cell, such drugs can achieve higher concentrations at sites of injury. Side effects from the conventional anti-inflammatory chemotherapeutic agents can be substantially alleviated by the lower dosages, the localization of the agent at the injury sites and/or the encapsulation of the agent prior to delivery.

The targeting component, i.e., the $SLe^x$ ligand or an $SLe^x$ mimetic which binds to a desired selectin, can be directly or indirectly coupled to the chemotherapeutic agent. The coupling, which may be performed by means generally known in the art, should not substantially inhibit the ability of the ligand to bind the receptor nor should it substantially reduce the activity of the chemotherapeutic agent. A variety of chemotherapeutics can be coupled for targeting. For example, anti-inflammatory agents which may be coupled include $SLe^x$-bearing compounds of the present invention, immunomodulators, platelet activating factor (PAF) antagonists, cyclooxygenase inhibitors, lipoxygenase inhibitors, and leukotriene antagonists. Some preferred moieties include cyclosporin A, indomethacin, naproxen, FK-506, mycophenolic acid, etc. Similarly, anti-oxidants, e.g., superoxide dismutase, are useful in treating reperfusion injury when targeted by a $SLe^x$ ligand or mimetic. Likewise, anticancer agents can be targeted by coupling the $SLe^x$ ligand or mimetic to the chemotherapeutic agent. Examples of agents which may be coupled include daunomycin, doxorubicin, vinblastine, bleomycin, etc.

The selectin receptor targeting may also be accomplished via amphipaths, or dual character molecules (polar:nonpolar) which exist as aggregates in aqueous solution. Amphipaths include nonpolar lipids, polar lipids, mono- and diglycerides, sulfatides, lysolecithin, phospholipids, saponin, bile acids and salts. These molecules can exist as emulsions and foams, micelles, insoluble monolayers, liquid crystals, phospholipid dispersions and lamellar layers. These are generically referred to herein as liposomes. In these preparations the drug to be delivered is incorporated as part of a liposome in conjunction with a $SLe^x$ ligand or mimetic which binds to the selectin receptor. Thus, liposomes filled with a desired chemotherapeutic agent can-be directed to a site of tissue injury by the selectin-$SLe^x$ ligand interaction. When the liposomes are brought into proximity of the affected cells, they deliver the selected therapeutic compositions.

The liposomes of the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Methods used in sizing and filter-sterilizing liposomes are discussed below. The acyl chain composition of phospholipid may also affect the stability of liposomes in the blood. One preferred phosphatidylcholine is partially hydrogenated egg phosphatidylcholine.

Targeting of liposomes using a variety of targeting agents (e.g., ligands, receptors and monoclonal antibodies) is well known in the art. (see, e.g., U.S. Pat. Nos. 4,957,773 and 4,603,044, both of which are incorporated herein by reference). Glycoproteins and glycolipids of a variety of molecular weights can be used as targeting agents. Typically, glycoproteins having a molecular weight less than about 300,000 daltons, preferably between about 40,000 and about 250,000 are used, more preferably between about 75,000 and about 150,000. Glycolipids of molecular weight of less than about 10,000 daltons, preferably between about 600 and about 4,000, are used. Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see, Renneisen, et al., *J. Biol. Chem.*, 265:16337–16342 (1990) and Leonetti et al., *Proc. Natl. Acad. Sci. (USA)* 87:2448–2451 (1990), both of which are incorporated herein by reference).

Targeting mechanisms generally require that the targeting agents be positioned on the surface of the liposome in such a manner that the target agents are available for interaction with the selectin receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation half-lives are typically desirable for therapeutic and diagnostic uses. Liposomes which can be maintained from 8, 12, or up to 24 hours in the bloodstream provide sustained release of the selectin-ligand inhibitors of the invention, or may facilitate targeting of the inhibitors (which may be labelled to provide for in vivo diagnostic imaging) to a desired site before being removed by the reticuloendothelial system.

Typically, the liposomes are prepared with about 5-15 mole percent negatively charged phospholipids, such as phosphatidylglycerol, phosphatidylserine or phosphatidylinositol. Added negatively charged phospholipids, such as phosphatidylglycerol, also serves to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5-15 mole percent of monosialylganglioside, may provide increased circulation of the liposome preparation in the bloodstream, as generally described in U.S. Pat. No. 4, 837,028, incorporated herein by reference.

Additionally, the liposome suspension may include lipid-protective agents which protect lipids and drug components against free-radical and lipid-peroxidative damages on storage. Lipophilic free-radical quenchers, such as alphatocopherol and water-soluble iron-specific chelators, such as ferrioxianine, are preferred.

A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, incorporated herein by reference. One method produces multilamellar vesicles of heterogeneous sizes. In this method, the vesicle forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration which is desired in the interior volume of the liposomes in the final liposome suspension. Typically the drug solution contains between 10-100 mg/ml in a buffered saline. The concentration of the targeting SLe$^x$ molecule or mimetic which binds a selectin is generally between about 0.1-20 mg/ml.

Following liposome preparation, the liposomes may be sized to achieve a desired size range and a relatively narrow distribution of liposome sizes. One preferred size range is about 0.2-0.4 microns, which allows the liposome suspension to be sterilized by filtration through a conventional filter, typically a 0.22 micron filter. The filter sterilization method can be carried out on a high through-put basis if the liposomes have been sized down to about 0.2-0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain up to 50% or more drug and targeting agent in free (non-encapsulated) form. Therefore, to maximize the advantages of liposomal targeted drug, it is important to remove free drug and targeting agent from the final injectable suspension.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a drug-free replacement medium. Alternatively, gel filtration can be used to separate large liposome particles from solute molecules.

Following treatment to remove free drug and/or targeting agent, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where-the drug removal step has increased total suspension volume. The suspension is then sterilized by filtration as described above. The liposome-ligand preparation may be administered parenterally or locally in a dose which varies according to, e.g., the manner of administration, the drug being delivered, the particular disease being treated, etc.

For pharmaceutical compositions which comprise the SLe$^x$ ligand, and/or SLe$^x$ mimetics which bind to selectin receptors, the dose of the compound will vary according to, e.g., the particular compound, the manner of administration, the particular disease being treated and its severity, the overall health and condition of the patient, and the judgment of the prescribing physician. For example, for the treatment of reperfusion injury, the dose is in the range of about 50 μg to 2,000 mg/day for a 70 kg patient. Ideally, therapeutic administration should begin as soon as possible after the myocardial infarction or other injury. The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and dragees.

Preferably, the pharmaceutical compositions are administered intravenously. Thus, this invention provides compositions for intravenous administration which comprise a solution of the compound dissolved or suspended in a pharmaceutically acceptable carrier, preferably an aqueous carrier. A variety of aqueous carriers may be used, e.g., water, buffered water, 0.4% saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of SLe$^x$ ligand or mimetic, which may be combined with other SLe$^x$ ligands or mimetics to form a "cocktail" for increased efficacy in the pharmaceutical formulation, can vary widely, i.e., from less than about 0.05%, usually at or at least about 1% to as much as 10 to 30% by weight and will be selected primarily by fluid volumes, viscosities, etc., in accordance with the particular mode of administration selected. The cocktail may also comprise a monoclonal antibody which binds to selectin receptor, e.g., a monoclonal antibody to E-Selectin or P-Selectin, combined with the SLe$^x$ ligand, a ligand mimetic or a monoclonal antibody to the ligand, so as to effectively inhibit the ligand-receptor interaction. As described above, the cocktail components may be delivered via liposome preparations.

Thus, a typical pharmaceutical composition for intravenous infusion could be made up to contain 250 ml of sterile Ringer's solution, and 25 mg of the compound. Actual methods for preparing parenterally administrable compounds will be known or apparent to those skilled in the art and are described in more detail in for example, *Remington's Pharmaceutical Sciences*, 17th ed., Mack Publishing Company, Easton, Pa. (1985), which is incorporated herein by reference.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more SLe$^x$ ligands or mimetics of the invention, preferably about 20% (see, *Remington's*, supra).

For aerosol administration, the compounds are preferably supplied in finely divided form along with a surfactant and propellant. Typical percentages of SLe$^x$ oligosaccharide ligands or mimetics are 0.05%-30% by weight, preferably 1%-10%. The surfactant must, of course, be nontoxic, and preferably be soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%-20% by weight of the composition, preferably 0.25-5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient, but generally range from about 0.5 mg to about 2,000 mg of SLe$^x$ oligosaccharide or SLe$^x$ mimetic per day for a 70 kg patient, with dosages of from about 5 mg to about 200 mg of the compounds per day being more commonly used.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of SLe$^x$ oligosaccharide or SLe$^x$ mimetic of this invention sufficient to effectively treat the patient.

The compounds may also find use as diagnostic reagents. For example, labeled compounds can be used to locate areas of inflammation or tumor metastasis in a patient suspected of having an inflammation. For this use, the compounds can be labeled with, for example, $^{125}$I, $^{14}$C, or tritium.

The following examples are offered by way of illustration, not by way of limitation.

EXAMPLE 1

Isolation of α1,3-fucosyltransferase I from Golgi Apparatus

LEC11, HL-60, HT-29, certain adenocarcinomas (colo 205 cells in particular), and polymorphonuclear leukocytes (PMN, neutrophils) contain a very specific α1,3-fucosyltransferase I, which is able to transfer fucose from GDP-fucose to the sialylated substrates NeuAcα2,3Galβ1, 4GlcNAc or NeuGcα2,3Galβ1,4GlcNAc.

It is well known in the art that fucose is transferred to oligosaccharide chains in the lumen of the Golgi apparatus via specific fucosyltransferases, reviewed in Schacter and Roseman, in "The Biochemistry of Glycoproteins and Proteoglycans", W. Lennarz, ed., Plenum Press, New York, pp. 85-160 (1980), which is incorporated herein by reference. Since the subcellular localization of the fucosyltransferases is in the Golgi apparatus, the first step in the isolation of these enzymes is to isolate a Golgi apparatus fraction from a cell line which expresses this novel and specific α1,3-fucosyltransferase.

Golgi apparatus-derived vesicle fractions are prepared by a modification of the procedure described by Balch et al., *Cell*, 39:405 (1984) which is incorporated herein by reference. The LEC11, HL-60, HT-29, PMN, colo 205 or other cell lines containing the α1,3-fucosyltransferase I are grown in suspension to a density of approximately $5 \times 10^5$ cells/ml. Cells are harvested from the suspension culture by centrifugation at 2,000×g. The resulting cell pellet from a 12 liter suspension ($6 \times 10^9$ cells) is resuspended in 3 volumes is (packed cell volume) of ice-cold 0.25M sucrose (w/v) solution containing Tris-Cl (10 mM), pH 7.0, heat inactivated fetal calf serum (7%), and APROTININ™ (100 µg/ml, Sigma Chemical, Co. St. Louis, Mo.).

The cells are disrupted (approximately 60 strokes) with a tight fitting Wheaton glass dounce homogenizer using the A pestle. The homogenate is centrifuged for 5 min. at 500×g in a table-top clinical centrifuge. Lipid and insoluble material remaining at the top of the solution in the centrifuge tube is discarded. The cloudy supernatant is transferred to a clean tube, and the sucrose concentration of the supernatant fraction is then adjusted to 40% (w/v) sucrose in Tris-Cl (20 mM), pH 7.0, with the aid of a refractometer. Five milliliters of this suspension is transferred to an ultracentrifuge tube and is layered sequentially with 2.5 ml of 35% (w/v) sucrose in Tris-Cl (10 mM, pH 7.0) and 2.0 ml of 29% (W/v) sucrose in 10 mM Tris-Cl buffer. The gradient is centrifuged for 1 hr. at 110,000×g in a SW-41 rotor (Beckman) at 5° C. Golgi apparatus enriched vesicles are collected from the 29% to 35% sucrose interphase. Other subcellular fractions are found at other interphases in the gradient; e.g., vesicles derived from the rough and smooth endoplasmic reticulum band below the Golgi derived vesicles, etc. The band removed from the 29% to 35% interphase is analyzed for the presence and amount of sialyltransferase activity.

The enzyme sialytransferase is only known to be found within Golgi apparatus-derived vesicles and is used by those trained in the art as a marker to assess the authenticity of the band collected from the 29–35% interphase. Sialyltransferase assays are performed using asialofetuin as the acceptor as described by Briles et al., *J. Biol. Chem.*, 252:1107 (1977). A good Golgi apparatus derived vesicle preparation from LEC cells typically has a sialyltransferase-specific activity of 3.0 nmole/mg protein/hr.

The resulting Golgi apparatus preparation is then used as a source of the α1,3-fucosyltransferase I used in the enzymatic synthesis described above.

EXAMPLE 2

Demonstration of Intercellular Adhesion by Cells Expressing SLe$^x$

The ability of LEC11 cells (which express SLe$^x$) to bind to activated endothelial cells displaying E-Selectin was compared to that of CHO cells and another glycosylation mutant, LEC12, which expresses the structure Le$^x$, a non-sialylated form of SLe$^x$.

MATERIALS

Passage 5 human umbilical vein endothelial cells (HUVEC) (Clonetics) which had been grown on a gelatin coated 48 well assay plate were used as the source of endothelial cells. Cells were stimulated with IL-1β (Genzyme) at 30 µg/ml. Cells were stimulated for exactly 4 hrs. HL-60 cells provided by American Type Culture Collection (ATCC No. CCL 240) were used as the control SLe$^x$ ligand-bearing cells. These were harvested from bulk culture in RPMI 1640 (Gibco) containing Penicillin (100 units/ml)/ Streptomycin (100 Mcg/ml)(Irvine Scientific), L-Glutamine (2 mM) (Irvine Scientific) and 10% Fetal Bovine Serum (Hazleton) (hereafter referred to as CRPMI). LEC11, LEC12 and CHO-K1 were provided by Dr. P. Stanley. They were grown in suspension culture in complete alpha MEM containing ribonucleotides and deoxyribonucleotides (Gibco), Penicillin (100 units/ml)/ Streptomycin (100 µg/ml) (Irvine Scientific), L-Glutamine (2 mM) (Irvine Scientific) and 10% Fetal Bovine Serum (Hazelton).

PROCEDURE

1. HL-60, LEC11, LEC12 and CHO-K1 cells were harvested and washed in CRPMI. A viable cell count was made using trypan blue. $3 \times 10^6$ cells of each type were pelleted in a 10 ml test tube and 300 µl of $^{51}$Cr (450 µCi) (New England Nuclear) was added to each pellet. The tubes were allowed to incubate 1 hour at 37° C. with gentle agitation.

2. Labeled cells were washed 3× in medium and resuspended to $2 \times 10^5$/ 400 µl (6 ml). The tubes were then placed in a 4° C. ice bath.

3. After 4 hours incubation with IL-1β the assay plate containing activated HUVEC was removed from the incubator and chilled for 15 minutes by placing the plate in a 4° C. ice bath.

4. When the temperature in both samples had equilibrated, the medium was removed from the assay wells with a pasteur pipette a few wells at a time.

5. Labeled cells were added to the wells in 400 µl volumes equal to $2 \times 10^5$ cells/well. Three 400 µl aliquots of each cell suspension were placed in glass tubes for determination of input CPMs.

6. The plate was incubated in the ice water bath for 30 minutes.

7. Unbound cells were removed from the wells of the assay plate by systematic resuspension using a pasteur pipette followed by addition and removal of 0.7 ml of medium.

8. All of the medium was removed from the wells and a solution of 0.125M Tris, 2% SDS and 10% glycerin was added (0.3 ml) to release the radioactive label. The plate was allowed to stand for 30 minutes and then 0.5 ml of dH$_2$O was added to each well.

9. The fluid in each well was mixed with a P1000 pipette and transferred to a glass test tube. The P1000 tip was ejected into the tube.

10. The tubes, including those containing the input CPM samples were counted in a gamma counter.

11. CPMs bound in each well were divided by the input CPMs for each sample to determine the % bound. The mean and standard deviation of triplicate assay points were plotted.

The results obtained in this experiment, shown in FIG. 1, indicate that cells expressing SLe$^x$ have the ability to bind effectively to activated vascular endothelial cells expressing E-Selectin. These data show that LEC11 cells which express high levels of the unique carbohydrate SLe$^x$ bind exceptionally well to IL-1β activated HUVEC, while LEC12 and CHO-K1, which lack significant quantities of this carbohydrate, are poor binders of the activated HUVEC. This conclusion is further supported by the observation that this binding occurs at 40° C., a characteristic of E-Selectin mediated binding.

EXAMPLE 3

Inhibition of Intercellular Adhesion by Monoclonal Antibodies Specific for SLe$^x$ Two sets of experiments are described which confirm that the ligand on neutrophils for E-Selectin contains an oligosaccharide on which the terminal sugars are NeuAcα2, 3Galβ1,4(Fuc α1,3)GlcNac (SLe$^x$).

These experiments are performed by assaying the ability of monoclonal antibodies specific for sialylated Le$^x$ and for the unsialylated form, Le$^x$, to block the E-Selectin mediated adhesion of HL-60 cells to IL-1β stimulated HUVEC.

A. Monoclonal Antibody Panel 1

Materials: Passage 3 HUVEC from cultures initiated for the present experiments were used as described above. Two sets of triplicate wells were left unstimulated as controls. Four sets of triplicates were stimulated with IL-1β (Genzyme) at 10 µg/ml and 4 sets at 20 µg/ml. Cells were stimulated for exactly 4 hours. HL-60 cells obtained from the American Type Culture Collection were used as the SLe$^x$ ligand-bearing cells. These were harvested from bulk culture in RPMI-1640 (Gibco) containing penicillin (100 units/ml), streptomycin (100 µg/ml) (Irvine Scientific), L-Glutamine (2 mM) (Irvine Scientific) and 10% Fetal Bovine Serum (Hazleton) (hereafter referred to as CRPMI).

Monoclonal antibody preparations included SNH3 (IgM) at about 20 µg/ml and SHI (IgG3) at about 10 µg/ml. The specificity of SNH3 is for SLe$^x$, while SH1 recognizes the unsialylated structure. Procedure:

1. HL-60 cells were harvested and washed in CRPMI. A viable cell count was made using trypan blue. 3×10$^6$ cells were placed in each of two 10 ml test tubes and 300 µl of $^{51}$Cr (450 µCi) (New England Nuclear) was added to each tube. The tubes were allowed to incubate 1 hour at 37° C. with gentle agitation.
2. The antibodies were supplied as hybridoma culture supernatants and contained 0.01% NaN3 and 0.05% thimerosal. To remove these preservatives, 5 ml of each antibody was dialysed against 3 changes (500 ml each) of outdated tissue culture medium over 72 hours.
3. Antibodies were collected from dialysis and 3.5 ml of each was placed in 10 ml tubes. The remainder was retained for use in an ELISA assay for HL-60 binding. 7 ml of RPMI 1640 5% FCS was placed in a fourth tube for use as a control.
4. Labeled HL-60 cells were washed 3× in CRPMI and pooled into one tube. They were then centrifuged and resuspended to 1 ml in medium.
5. 200 µl of labelled HL-60 cell suspension was added to each of the antibody containing tubes and 400 µl to the control tube. Tubes were incubated 20 min. at 37° C. with gentle agitation.
6. The stimulated HUVEC assay plate was removed from the incubator and the medium was removed from the wells with a pasteur pipette, a few wells at a time.
7. 0.5 ml of cell suspension was added to each of triplicate wells. Control cells (no antibody) were plated on unstimulated and stimulated HUVEC at both IL-1β concentrations. Test cells (with antibody) were added to stimulated wells only.
8. 0.5 ml aliquots of each cell suspension were added to glass tubes to be used to determine the input CPMs.
9. The assay plate was returned to the incubator (5% CO$_2$, 37° C.) for 30 min.
10. An aliquot of each cell suspension was mixed with an equal volume of trypan blue and the cells were examined microscopically for viability. The results were: Control=98% viable, SH1=92%, and SNH3=99%.
11. Unbound cells were removed from the wells of the assay plate by systematic resuspension using a pasteur pipette followed by addition and removal of 0.7 ml of medium.
12. All of the medium was removed from the wells and a solution of 0.125M Tris, 2% SDS (Bio-Rad) and 10% glycerin (Fisher) was added (0.3 ml). The plates were allowed to stand for 30 min. and then 0.6 ml of dH$_2$O was added to each well.
13. The fluid in each well was resuspended with a P1000 pipette and transferred to a glass test tube. The P1000 tip was ejected into the tube.
14. The tubes, including those containing the input counts per minute (CPM) samples were counted in a gamma counter.
15. CPMs bound in each well were divided by the input CPMs for each sample to determine the % bound. The mean and standard deviation of triplicate assay points were plotted.

Replicates were judged to be best in the experiment in which high IL-1β was used to induce the endothelial cells.

The results demonstrated that the monoclonal antibody SNH3 blocked the binding of HL-60 cells to IL-1β stimulated HUVEC via the E-Selectin receptor. The control antibody SH1, which does not bind the SLe$^x$ determinant, did not block binding of HL-60 cells to ELAM-1. This suggests that the terminal sialic acid in the ligand is necessary for binding to E-Selectin.

B. Monoclonal Antibody Panel 2

Materials: Passage 3 HUVEC which had been grown on gelatin coated 48 well assay plates (Costar) were used as the source of endothelial cells. The plates were prepared as previously described above. Two sets of triplicate wells were left unstimulated as controls. Seven sets of triplicates on each plate were stimulated with IL-1β at 30 µg/ml in 0.5 ml of EGM-UV. Cells were stimulated for exactly 4 hrs. HL-60 cells (ATCC) were used as the source of SLe$^x$ ligand-bearing cells. These were harvested from bulk culture in CRPMI. Fresh hybridoma supernatants containing monoclonal antibodies included: FH6 (IgM) a SLe$^x$-reactive mAb with lower affinity than SNH-4; SNH-3 (IgM) (20 µg/ml); SH-1 (IgG3) (10 µg/ml); FH-2 (IgM) a Le$^x$-reactive mAb; SNH-4 (IgG3) a high affinity SLe$^x$-reactive antibody; and CSLEX-1 (IgM) (provided by Dr. P. Terasaki, UCLA as purified immunoglobulin at 2.8 mg/ml, diluted to 9 µg/ml in Dulbecco's Modified Eagles Medium (DMEM) containing 5% FCS for use in this assay). The specificities of the antibodies were as follows: FH6, SNH-4, SNH3 and CSLEX-1 were specific for SLe$^x$; FH2 and SH1 were specific for the unsialylated Le$^x$.

Procedure

1. HL-60 cells were harvested and washed in CRPMI. A viable cell count was made using trypan blue. 3×10$^6$ cells were placed in each of two 10 ml test tubes and 300 µl of $^{51}$Cr (450 µCi) (New England Nuclear) was added to each tube. The tubes were allowed to incubate 1 hour at 37° C. with gentle agitation.
2. Labeled HL-60 cells were washed 3× in DMEM containing 5% FCS (hereafter referred to as cDMEM) and pooled into one tube. They were then centrifuged and resuspended to 4×10$^6$ cells per ml in the same medium.
3. 3.2 ml of each monoclonal antibody culture supernatant, and 3.2 ml purified CSLEX-1 (29 µg), were added to separate test tubes; a control tube received 6.4 ml of medium.
4. 200 µl of cell suspension (equal to about 8×10$^5$ cells) was added to tubes containing the monoclonal antibodies and 400 µl to the control tube. Tubes were then incubated 20 min. at 37° C. with gentle agitation.
5. The stimulated HUVEC assay plate was removed from the incubator and the wells were washed one time with cDMEM and the medium was removed from the wells with a pasteur pipette, a few wells at a time.

6. 0.4 ml of cell suspension was added to each well of one of the two plates. Control cells were plated on unstimulated and stimulated HUVEC. Antibody treated cells were added to stimulated wells only.

7. 0.4 ml aliquots of each cell suspension were added to glass tubes to be used to determine the input CPMS.

8. The assay plate was incubated at 37° C. for 30 min.

9. The remainder of each cell suspension and the assay plate were placed in an ice bath to chill for 20 min.

10. The cell suspensions were plated on the chilled plate as for the 370° C. plate above. This plate was incubated for 30 min. at 4° C.

The remaining steps of the assay were performed as described in steps 11–15 of Section A above, except that in step 12 the plates were allowed to stand for 15 min. rather than 30 min.

Figure 2A:
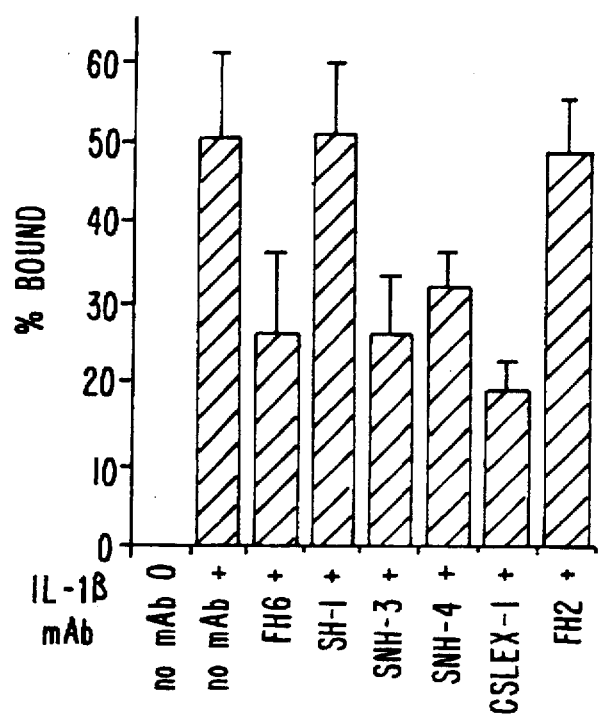
FIGS. 2A and 2B illustrate the ability of monoclonal antibodies specific for SLe$^x$ to block selectin-mediated binding of HL-60 cells at 37° C.

The results, shown in FIG. 2A, indicate that the monoclonal antibodies SNH-3, FH6, SNH-4 and CSLEX-1, all specific for SLe$^x$, significantly blocked the binding of HL-60 cells to IL-1β stimulated HUVEC via the E-Selectin receptor when incubated at 37° C. The monoclonal antibodies specific for Le$^x$ (FH2 and SH1) were not effective inhibitors. Thus, the ligand for E-Selectin contains the sialylated Le$^x$ antigen or a similar structure found in cell surface glycoproteins or glycolipids.

Figure 2B:
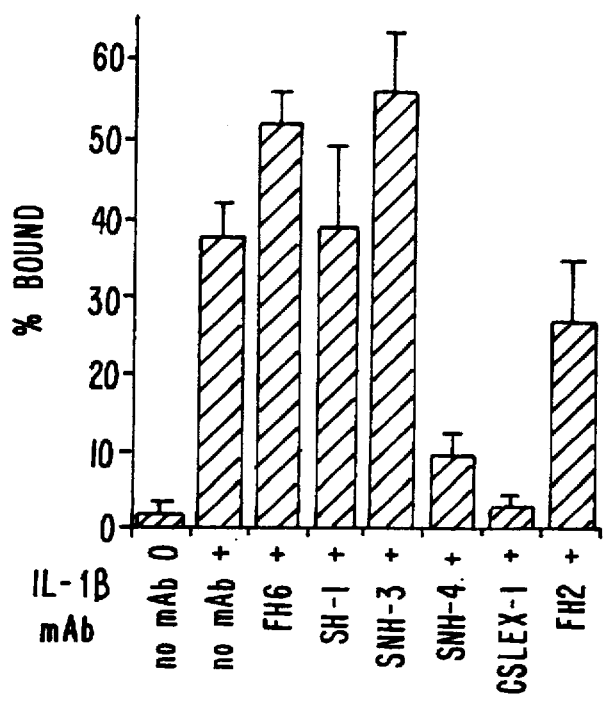

When incubated at 4° C. (FIG. 2B), antibodies FH6 and SNH-3 (both IgM's) enhanced binding. In these tests there appeared to be significant agglutination of the HL-60 cells in the wells, which may account for this observation.

C. Monoclonal Antibodies Block Adhesion of LEC11 Cells to Cells which Express E-Selectin In this set of experiments the ability of monoclonal antibodies specific for SLe$^x$ and for the unsialylated form, Le$^x$, to block the E-Selectin mediated adhesion of LEC11 cells (which express SLe$^x$) and LEC12 cells (which express Le$^x$) to IL-1 stimulated HUVEC.

Materials: Passage 4 HUVEC served as the source of endothelial cells. The plates were prepared as previously described. Two sets of triplicate wells were left unstimulated as controls. Seven sets of triplicates on each plate were stimulated with IL-1β at 30 µg/ml in a 0.5 ml volume of EGM-UV. Cells were stimulated for exactly 4 hrs. LEC11 and LEC12 cells, described generally in Stanley et al., *J. Biol. Chem.*, 263:11374 (1988), supra, were provided by Dr. P. Stanley. They were grown in suspension culture in complete alpha MEM containing ribonucleotides and deoxyribonucleotides (Gibco), penicillin (100 units 1ml)/streptomycin (100 µg/ml) (Irvine Scientific), L-Glutamine (2 mM) (Irvine Scientific) and 10% FBS (Hazelton). The monoclonal antibodies used in these experiments are described in Section B, above. They included: FH6, SNH-3, SH-1, FH-2, SNH-4 and CSLEX-1.

Procedure

1. LEC11 and LEC12 cells were harvested and washed in CRPMI. A viable cell count was made using trypan blue. 3×10$^6$ cells of each cell line were placed in each of two 10 ml test tubes and 300 µl of $^{51}$Cr (450 µCi) (New England Nuclear) was added to each tube. The tubes were allowed to incubate 1 hr. at 37° C. with gentle agitation.

2. The radiolabeled cells were washed 3 in cDMEM and pooled into one tube. They were then centrifuged and resuspended to 4×10$^6$ cells per ml in the same medium.

3. 1.6 ml of each monoclonal antibody supernatant, and 1.6 ml purified CSLEX-1 (15 µg), were added to separate test tubes; control tubes received 3.2 ml medium.

4. 200 µl of cell suspension equal to 4×10$^5$ LEC11 or LEC12 cells were added to tubes containing the monoclonal antibodies and 400 µl to the control tube. Tubes were incubated 20 min. at 37° C. with gentle agitation.

5. The stimulated HUVEC assay plate was removed from the incubator and the wells were washed one time with cDMEM and the medium was removed from the wells with a pasteur pipette, a few wells at a time.

6. The cell suspensions and the assay plate were placed in an ice bath to chill for 20 min.

7. 0.4 ml of cell suspension was added to each well of the previously described assay plate. Control cells (no antibody) were plated on unstimulated and stimulated HUVEC. Antibody treated cells were added to stimulated wells only. Each assay was done in triplicate.

8. 0.4 ml aliquots of each cell suspension were added to glass tubes to be used to determine the input CPMs.

9. The assay plate was incubated for 30 min. at 4° C.

The remaining steps of the assay were performed as described in steps 11–15 of Section A, above, except that in step 12 the plates were allowed to stand for 15 min.

Figure 3A:
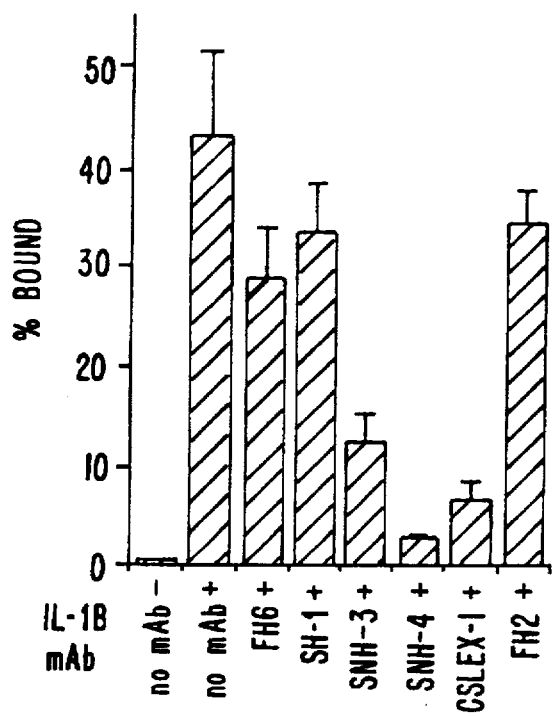
FIGS. 3A and 3B illustrate the effects of incubating LEC 11 (FIG. 3A) and LEC 12 (FIG. 3B) cells with SLe$^x$ and non-SLe$^x$ specific monoclonal antibodies on binding to activated endothelial cells.
Figure 3B:
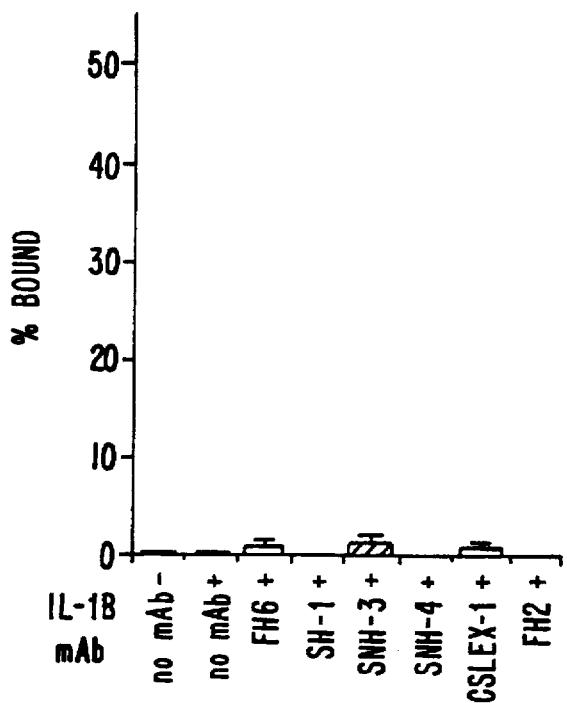

The results shown, in FIGS. 3A and 3B, indicate that the monoclonal antibodies SNH-3, FH6, SNH-4 and CSLEX-1 (all specific for SLe$^x$) significantly blocked the binding of LEC11 cells to IL-1β stimulated HUVEC via the E-Selectin receptor. LEC12 cells, which do not express the SLe$^x$ epitope, did not bind the activated endothelium. The monoclonal antibodies specific for Le$^x$ (FH2 and SH1) caused minor inhibition of LEC11 binding.

Further confirmation that SLe$^x$ is a primary ligand for E-Selectin receptor was provided by removing sialic acid from LEC 11 and HL-60 cells. In these experiments, prior to the adhesion assays, the LEC 11 and HL-60 cells were treated with *Clostridium serfringens* neuraminidase (sialidase), 1.6 U/ml (Type X, Sigma Chem. Co.) for 90 min. at 37° C. during the $^{51}$Cr-labelling. The results, shown in FIG. 4, confirm that sialidase substantially reduced the adhesion of LEC 11 and HL-60 cells to activated endothelial cells (by 70–85%).

EXAMPLE 4

Liposomes of Glycosphingolivids Block Binding of SLe$^x$ Cells to Activated Endothelial Cells This Example describes the preparation of liposomes which contain various biosynthetically produced glycosphingolipids on which the terminal carbohydrate units are either SLe$^x$, Le$^x$, or similar but not identical compounds. The ability of the liposomes which contain SLe$^x$ or SLe$^x$ mimetics to block the binding of SLe$^x$-expressing HL-60 cells and LEC11 cells to endothelial cells that have been stimulated to express E-Selectin by treatment with IL-1β is shown.

Materials: The glycosphingolipids used in this experiment are shown in Table I; they were obtained from the Biomembrane Institute, Seattle, Wash., and were either purified or biosynthetically produced and characterized by NMR and mass spectrometry, as generally described in Hakomori, S. I., et al., *J. Biol. Chem.*, 259:4672 (1984), and Fukushi Y., et al., *J. Biol. Chem.* 259:10511 (1984), incorporated by reference herein. S-diLex (SLe$^x$) was synthesized enzymatically by adding fucosyl residues using a colo 205 cell line as enzyme source and SH as substrate. Nonsialylated diLex was similarly synthesized using nLc6 as substrate and the cell line NCI H-69. See Holmes et al., *J. Biol. Chem.* 260:7619 (1985), incorporated by reference herein. SPG and SH were purified from bovine red blood cells, and nLc6 was produced by chemical removal of the terminal sialosyl residue from SH.

Liposomes containing the glycosphingolipids were formed as follows: 100 µg of glycolipid was added to 300 µg phosphatidylcholine (Sigma, egg yolk) and 500 µg cholesterol (Sigma) in chloroform-methanol (2:1) and the whole solution evaporated to dryness by $N_2$ in 15 ml screwcap tubes.

Passage 3 HUVEC, which had been grown to confluence on a gelatin coated 48 well assay plate (Costar) were used as the source of endothelial cells. The plates were prepared as previously described. Two sets of triplicate wells were left unstimulated as controls. Fourteen sets of triplicates were stimulated with IL-1β at 30 µg/ml in a 0.5 ml volume of EGM-UV. Cells were stimulated for exactly 4 hrs. HL-60 cells and LEC11 cells were cultured as described above.

Procedure

1. One 48 well Costar cluster dish containing HUVEC grown to confluence on gelatin was removed from the incubator and the medium in each well was removed with a pasteur pipette and replaced either with 0.5 ml fresh EGM-UV medium or with the same medium containing 30 µg/ml IL-1β,and the plate then returned to the incubator for 4 hrs.
2. HL-60 cells and LEC11 cells were harvested and washed in CRPMI. A viable cell count was made using trypan blue. 6×10$^6$ cells of each cell type were radiolabeled as follows: 3×10$^6$ cells of each type were placed in each of two 10 ml test tubes and 300 µl of $^{51}$Cr (450 µCi) (New England Nuclear) was added to each tube. The tubes were allowed to incubate 1 hr. at 37° C. with gentle agitation.
3. Radiolabeled HL-60 and LEC11 cells were washed 3× in CRPMI and pooled into one tube. They were then centrifuged and resuspended to 2×10$^6$ cells per ml in the same medium.
4. The stimulated HUVEC assay plate was removed from the incubator and the wells were washed two times with RPMI 1640 containing 5 mg/ml bovine serum albumin (BSA).
5. Liposomes were prepared as follows: The evaporated pellets were dissolved in 100 µl of absolute ethanol and sonicated for 2 min. Two ml of PBS was added slowly to the tubes over two minutes while continuing to sonicate. This stock was diluted 1:10 in RPMI 1640 medium just prior to use and 50 µl of a stock solution of BSA at 100 mg/ml was added to each 1 ml of diluted liposomes to make a final concentration of 5 mg/ml BSA.
6. The medium was removed from the wells of the assay plate with a pasteur pipette, a few wells at a time, and 0.3 ml of liposome suspension was added to each of six IL-1β stimulated assay wells. Control wells received the liposome buffer, which contained ethanol, RPMI 1640 and BSA at the same concentrations as in the liposome containing wells. Control buffer was plated on unstimulated and stimulated HUVEC. Liposome containing samples were added to stimulated wells only.
7. The plates were incubated for 40 min. at 370° C. and then 50 µl of $^{51}$Cr labeled HL-60 or LEC11 cells were added to the assay wells. Each cell line was assayed in triplicate on each liposome preparation. The final concentration of cells was 10$^5$ cells in 350 µl per well. Three aliquots of 50 µl of each cell suspension were added to glass tubes to be used to determine the input CPMS, and the assay plate was incubated at 37° C. for 30 min.
8. Unbound cells were removed from the wells of the assay plates by systematic resuspension using a pasteur pipette followed by addition and removal of 0.7 ml of medium. All of the medium was removed from the wells and a solution of 0.125M Tris, 2% SDS and 10% glycerin was added (0.3 ml). The plates were allowed to stand for 15 min. and then 0.5 ml of $dH_2O$ was added to each well.
9. The fluid in each well was resuspended and transferred to a glass test tube. The pipette tip was ejected into the tube. The tubes, including those containing the input CPM samples, were counted in a gamma counter. CPMs bound in each well were divided by the input CPMs for each sample to determine the e bound. The means and standard error of triplicate assay points were plotted.

As shown in FIG. 5, liposomes containing selected glycolipids having terminal sequences which contained SLe$^x$ (S-diLe$^x$, Table 1) dramatically inhibited adhesion of HL-60 cells to activated endothelial cells at 4° C. Liposomes containing glycolipids with Le$^x$ (di-Le$^x$) or other related carbohydrate structures (Table 1) exhibited minimal inhibition that was not dependent on the structure of the carbohydrate group. Similar results were obtained with LEC 11 cell adhesion. When the experiments were performed at 37° C., HL-60 cell adhesion was reduced by liposomes containing glycolipids with the SLe$^x$ structure (S-diLe$^x$, 70%), and also to a lesser extent by liposomes containing Lex (di-Le$^x$, 40%) suggesting that Le$^x$ may also interact with E-Selectin, but with a lower affinity. These experiments show that biosynthetically produced SLe$^x$ or similar SLe$^x$ mimetic compounds, when formulated into liposome compositions, can serve as therapeutic compounds for, e.g., the reduction of leukocyte infiltration into inflammatory sites.

Jurkat cells bind to IL-1 activated endothelial cells predominantly through the V-CAM (endothelial cell)—VLA-4 (Jurkat cell) adhesion pair (Wayner et al., *J. Cell Biol.* 109:1321), in contrast to the adhesion of HL-60 and LEC 11 cells to activated endothelial cells which occurs through the E-Selectin receptor. Jurkat cell adhesion was not inhibited by liposomes which contained SLe$^x$, but was completely inhibited by monoclonal antibody to the a subunit of the integrin molecule VLA-4. This result demonstrates that SLe$^x$ liposome inhibition of HL-60 and LEC 11 cells is not a steric effect attributable to binding of liposomes to endothelial cells, but supports the conclusion that SLe$^x$ liposomes inhibit the adhesion through a direct competition with the ligand binding site of E-Selectin.

TABLE 1

Glycolipids tested for liposome inhibition of E-Selectin mediated cell adhesion.

| Generic | IUPAC | Structure |
|---------|-------|-----------|
| nLc6 | nLc6 | Galβ1→4GlcNAcβ1→3Galβ1→4GlcNAcβ1→3Galβ1→4Glcβ1→1Cer |
| diLe1 | III$^3$V$^3$Fuc$_2$nLc$_6$ | Galβ1→4GlcNAcβ1→3Galβ1→4GlcNAcβ1→3Galβ1→4Glcβ1→1Cer<br>　　　　　　3　　　　　　　　　　　　3<br>　　　　　　↑　　　　　　　　　　　　↑<br>　　　　　Fucα1　　　　　　　　　　Fucα1 |
| SPG | IV$^3$NeuAcnLc$_4$ | NeuAcα2→3Galβ1→4GlcNAcβ1→3Galβ1→4Glcβ1→1Cer |
| SH | VI$^3$NeuAcnLc$_6$ | NeuAcα2→3Galβ1→4GlcNacβ1→3Galβ1→4GlcNAcβ1→3Galβ1→4Glcβ1→1Cer |
| S-diLe$^x$ | III$^3$V$^3$Fuc$_2$VI$^3$NeuAcnLc$_6$ | NeuAcα2→3Galβ1→4GlcNAcβ1→3Galβ1→4GlcNAcβ1→3Galβ1→4Glcβ1→1Cer<br>　　　　　　　3　　　　　　　　　　　　　　　　3<br>　　　　　　　↑　　　　　　　　　　　　　　　　↑<br>　　　　　　Fucα1　　　　　　　　　　　　　Fucα1 |

EXAMPLE 5

Antibodies to SLe$^x$ Inhibit P-Selectin Mediated Binding of Activated Human Platelets In this Example, the ability of monoclonal antibodies specific for SLe$^x$ and for the unsialylated Le$^x$ to block the P-Selectin mediated adhesion of HL-60 cells to activated human platelets was determined.

Materials: HL-60 cells are described above and were used as the source of ligand bearing cells. Jurkat cells were used as the non-ligand bearing control. Monoclonal antibodies SH-1, FH-2, SNH-4, and CSLEX-1 are also described above.

Procedure

1. Blood was drawn from a normal human donor into a syringe containing ACD anticoagulant (dextrose, 2.0 g; sodium citrate 2.49 g; and citric acid 1.25 g; to 100 ml with dH$_2$O) at a ratio of 6 parts blood to 1 part anticoagulant.

Platelets were isolated by differential centrifugation as follows: Blood was centrifuged at 800 rpm (approx. 90×g) for 15 min. at room temp. The supernatant was collected and centrifuged at 1200 rpm (approximately 400×g) for 6 min. The supernatant was removed and centrifuged at 2000 rpm (1200×g) for 10 min to pellet the platelets. The platelet button was washed 2 times with Tyrode-HEPES buffer, pH 6.5 (NaCl 8.0 g; KCl 0.2 g; NaH$_2$PO$_4$.H$_2$O 0.057 g; MgCl$_2$.6H$_2$O 0.184 g; NaHCO$_3$0.1 g; Dextrose, 1.0 g; and HEPES, 2.383 g; bring to 1 L with deionized water, adjust to pH 6.5 with 1N NaOH) followed by one wash in PBS. Platelets were suspended to a concentration of 10$^8$/ml in PBS.

2. Approximately 20 min. before the platelets were finally resuspended, 48 well plates were coated with 0.1% gelatin and incubated to 15 min. at 37° C. Excess gelatin was removed by pipette immediately before the addition of the platelet suspension. Platelets were activated by the addition of 0.25 units of thrombin/ml (Sigma T-6759) of platelet suspension. Platelets were allowed to stand at room temperature for 20 min.

3. To prepare bound, activated platelets, 300 µl of the platelet suspension was added to each well of the gel coated plate. The plate was incubated at 37° C. to 15 min., then spun at 800 rpm (90×g) for 2 min. The unbound platelets were removed by washing the plate 3 times with PBS.

4. Since platelets possess highly reactive Fc receptors, to prevent uptake of any aggregated IgG from the antibody preparation, the platelet Fc receptors were blocked as follows: Purified mouse IgG W6/32 (IgG$_{2a}$) at 27 mg/ml was aggregated by heating at 63° C. for 5 min. 300 µl of the heated preparation at 20 µg/ml in PBS was added to each well of the platelet-coated plate. The plate was incubated at 37° C. for 15 min. then washed with PBS.

5. HL-60 and Jurkat cells were harvested and washed in CRPMI. A viable cell count was made using trypan blue, 3×10$^6$ cells of each type were placed in each of two 10 ml test tubes and 300 µl of $^{51}$Cr (450 µCi) (New England Nuclear) was added to each tube. The tubes were incubated for 1 hr. at 37° C. with gentle agitation.

6. Radiolabeled cells were washed 3× in CRPMI and pooled into one tube. They were then centrifuged and resuspended to 4×10$^6$ cells per ml in the same medium.

7. 1.6 ml of each monoclonal antibody culture supernatant, and 1.6 ml of purified CSLEX-1 (15 µg) were added to separate test tubes; control tubes received 1.6 ml of medium.

8. 100 µl of the labeled HL-60 or Jurkat cell suspension (containing 4 × 105 cells) was added to each of the tubes which contained monoclonal antibody. They were incubated for 20 min. at 37° C. with gentle agitation. Following this incubation period, 0.3 ml of each cell suspension (containing 7.5×10$^4$ cells) was added to each well of the previously described assay plate containing bound activated platelets. Each assay was done in triplicate.

9. The assay plate was centrifuged at 90×g for 2 min. and then incubated for 5 min. at room temp. Unbound cells were removed from the wells of the assay plate by inverting the plate into a radioactive waste receptacle and blotting the plate on towels. The wells were washed three times by carefully adding 300 µl PBS to each well and inverting and blotting the plate. All of the medium was removed from the wells and 0.3 ml of a solution of 0.125M Tris, 2% SDS and 10% glycerin was added. The plates were allowed to stand for 15 min. and then 0.6 ml of dH$_2$O was added to each well.

10. The fluid in each well was resuspended with a pipette and transferred to a glass test tube. The tip was ejected into the tube. The tubes, including those containing the input samples, were counted in a gamma counter.

CPMs bound in each well were divided by the input CPMs for each sample to determine the e bound. Input CPMs were determined by counting a 0.3 ml aliquot of each cell suspension described in step 8.

Figure 6:
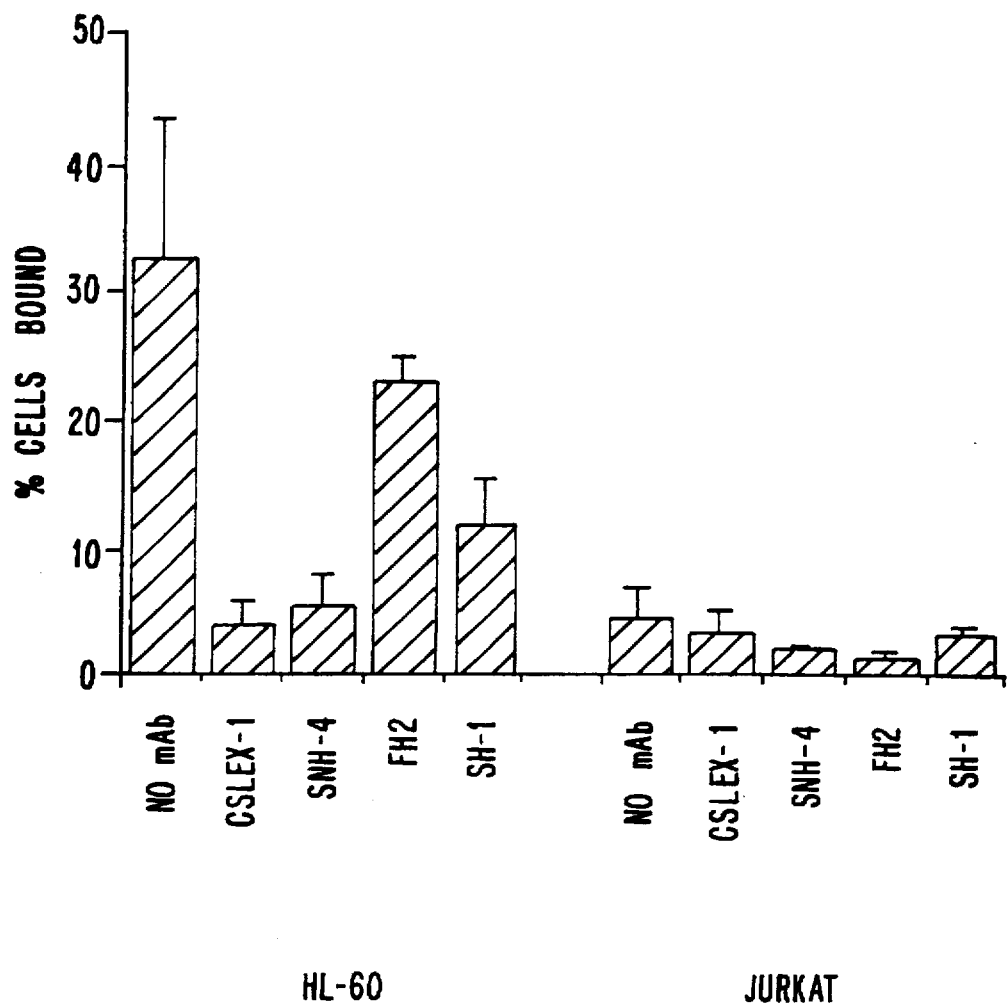
FIG. 6 compares the inhibition of P-Selectin mediated platelet adhesion by monoclonal antibodies specific for SLe$^x$ and Le$^x$ determinants.

The results, shown in FIG. 6, indicate that the monoclonal antibodies SNH-4 and CSLEX-1 (specific for SLe$^x$) blocked the binding of HL-60 cells to P-Selectin on activated platelets. The monoclonal antibodies specific for Le$^x$ (FH2 and SH-1) also blocked this binding but to a lesser extent. This Example suggests that both SLe$^x$ and Le$^x$ may be ligands for P-Selectin, but that the SLe$^x$ structure may be of a higher affinity for P-Selectin than the Le$^x$ structure.

EXAMPLE 6

Liposomes of Glycosphingolivids Block Binding of SLe$^x$ Cells to Activated Platelets This Example demonstrates the ability of the liposomes which contain SLe$^x$ or SLe$^x$ mimetics to block the binding of SLe$^x$-expressing HL-60 cells and PMNs to platelets which have been stimulated to express P-Selectin by treatment with thrombin. The assays generally followed the protocol described in Larsen et al., Cell 63: 467–474 (1990), which is incorporated herein by reference.

Materials

Glycosphingolipids and liposomes were prepared as described in Example IV. The platelets were prepared as described in Example V, except that blocking of Fc receptors was not performed. HL60 cells were prepared as described above.

PMNs were prepared from 50 ml of whole blood drawn from volunteer donors into heparinized vacutainer tubes, which were inverted to mix the blood. All steps were performed at 22–24 degrees C. Each 25 ml of blood was layered over 15 ml of Mono-Poly Resolving Medium (Flow Labs). The tubes were centrifuged at 800×g for 25 min followed by 1300×g for a further 25 min. The PMN layer was removed and placed in a clean 50 cc centrifuge tube. Thirty ml of Hanks Balanced Salt Solution (Gibco) containing 20 mM HEPES (Gibco) and 0.2% glucose (Fisher) was added to each tube, which were then centrifuged at 1900×g for 3 min. The PMNs were washed 3× in the same buffer by centrifugation at 1900×g for 3 min. PMNs were counted using a hemacytometer and resuspended to $2 \times 10^6$/ml and held at room temperature until use.

Procedure 1. 20 µl of activated platelet preparation was placed in each of 28 1.5 ml microfuge tubes (14 duplicate samples).

2. 20 µl of the diluted liposomes at 10 Mg, 5 µg or 2 µg, or 20 µl of the control buffers, were added to the appropriate tube of each duplicate.

3. The platelets were incubated with the liposome preparations for 20 min. at room temp.

4. Neutrophils or HL-60 cells at $2 \times 10^6$ cells/ml were each added to one set of liposome-treated platelets. 20 µl of cell suspension were added to each tube.

5. The tubes were mixed and allowed to stand at room temperature for 20 min. Then they were applied to a hemacytometer and the cells were scored as positive (2 or more platelets attached/cell) or negative (less than 2 platelets attached/cell).

Figure 7:
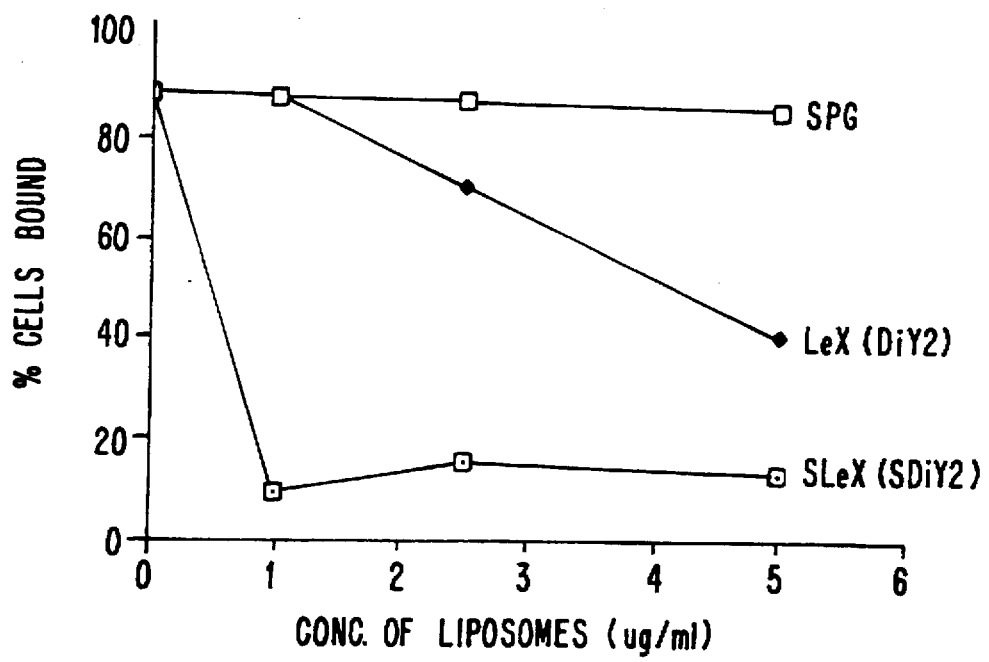
FIG. 7 compares the ability of liposomes which contain glycolipids having SLe$^x$, Le$^x$, or similar carbohydrate structures to inhibit the binding of HL-60 cells to activated platelets.
Figure 8:
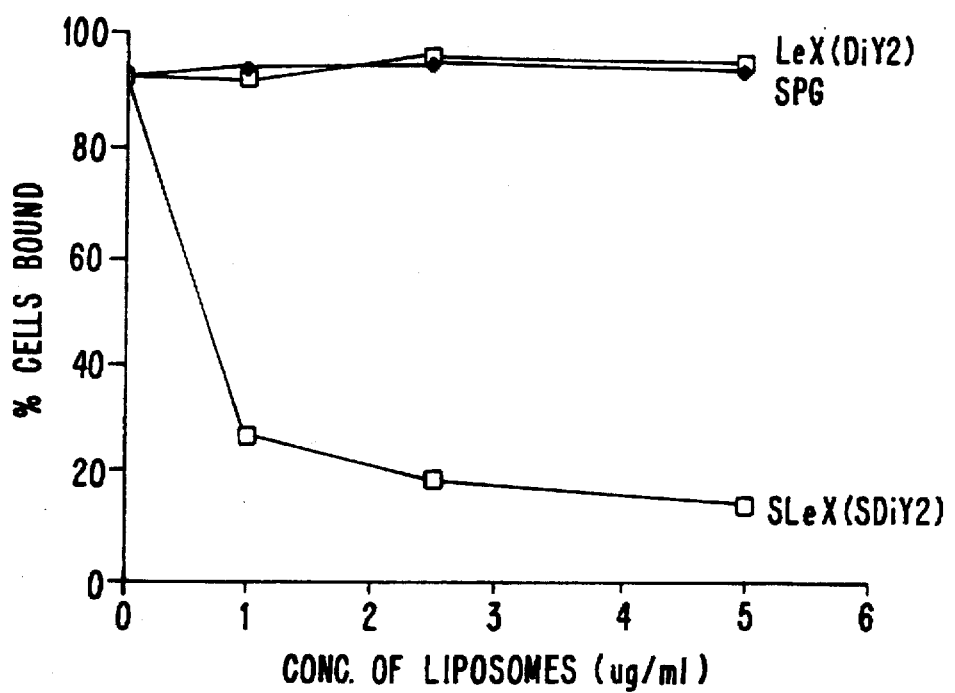
FIG. 8 compares the ability of liposomes which contain glycolipids having SLe$^x$, Le$^x$, or similar carbohydrate structures to inhibit the binding of PMNs to activated platelets.

As shown in FIG. 7, liposomes containing selected glycolipids having terminal sequences which contained SLe$^x$ (S-diLEX, Table 1) dramatically inhibited adhesion of HL-60 cells to activated platelets. Liposomes containing glycolipids with Le$^x$ (di-Le$^x$) or other related carbohydrate structures (Table 1) exhibited minimal inhibition that was not dependent on the structure of the carbohydrate group. Similar results were obtained with PMN cell adhesion (FIG. 8). These experiments show that biosynthetically produced SLe$^x$ or similar SLe$^x$ mimetic compounds, when formulated into liposomes compositions, can serve as therapeutic compounds for, e.g., the reduction of leukocyte binding to platelets in inflammatory sites.

EXAMPLE 7

Oligosaccharide containing SLe$^x$ blocks binding of Neutrophils to Platelets In this example the ability of a minimal tetrasaccharide SLe$^x$ to inhibit P-Selectin adhesion was compared to that of penta- and hexasaccharides containing SLe$^x$. Briefly, platelets and neutrophils were isolated by the methods described above. Platelets were activated with thrombin and then incubated with dilutions of various oligosaccharides. Neutrophils were added, and the effect of the saccharides on the adhesion of neutrophils to activated platelets was determined. The oligosaccharides used were as follows: SLe$^x$ (hexa), NeuAcα2,3Galβ1,4 (Fucα1,3)GlcNacβ1,3 Galβ1, 4Glc-O—CH2CH2SiMe3 (the generous gift of Professor Hasegawa, Gifu University, Japan); SLe$^x$(penta) NeuAcα2, 3Galβ1,4-(Fucα1,3)GlcNacβ1,3Galβ; and SLe$^x$(tetra), NeuAcα2,3Galβ1,4 (Fucα1,3)GlcNAc.

Procedure

1. Platelets were isolated as described above and were activated ($2 \times 10^8$/ml) by incubation for 20 min at room temperature with thrombin at a final concentration of 0.25 U/ml.

2. Neutrophils were isolated by layering heparinized blood over Mono-Poly Resolving Medium (Ficoll-Hypaque-Flow Laboratories), followed by centrifugation for 25 min at 2000 rpm and then, a further 25 min at 2500 rpm as described above.

3. For the assay, 20 µl of the platelet suspension ($2 \times 10^8$/ml) was placed in a microcentrifuge tube. An equal volume of the oligosaccharide preparations at concentrations from 200 µg/ml to 0.3 µg/ml, or of glycolipid-liposome preparations (prepared as described above), at concentrations from 2 µg/ml to 0.25 µg/ml, was added and the tubes were allowed to stand at room temperature for 20 min. Twenty µl of the neutrophil preparation ($2 \times 10^6$/ml) was then added and the tubes were allowed to stand for a further 20 min at room temperature.

4. Adhesion of activated platelets to the neutrophils was assessed microscopically. One hundred neutrophils were evaluated. They were scored as positive if 2 or more platelets were attached and negative if less than 2 platelets were bound. The percent of cells with 2 or more bound platelets was calculated.

The mean of the results of three identical experiments are shown in Table 2.

TABLE 2

| OLIGOSACCHARIDE | AMOUNT REQUIRED FOR 50% INHIBITION (µM) |
|---|---|
| SLe$^x$ (hexa) | 1.8 |
| SLe$^x$ (penta) | 2.2 |
| SLe$^x$ (tetra) | 54.0 |
| Le$^x$ | 43.0 |

As indicated in Table 2 above, approximately 20 times more of the SLe$^x$-tetrasaccharide is required for 50% inhibition of P-Selectin mediated binding of neutrophils to thrombin activated platelets than of the SLe$^x$-hexasaccharide. The amount of the tetrasaccharide required is approximately that needed for a similar degree of inhibition when the non-sialylated Lex was used. The pentasaccharide gives 50% inhibition at concentrations similar to those required for 50% inhibition by the hexasaccharide which indicates that the minimal structure for maximum inhibition is closer to a pentasaccharide.

EXAMPLE 8

Blocking adhesion using variant SLe$^x$ structures

This example describes experiments testing various glycolipid structures on liposomes. In particular, SY2, a sialylated polysaccharide in which the fucose, instead of being attached to the ultimate GlcNAc as in SLe$^x$, is attached to the penultimate GlcNAc, was tested. Platelets and neutrophils were isolated by the methods described above. Platelets were activated with thrombin and then incubated with dilutions of various glycolipids embedded in liposomes prepared as described above. Neutrophils were added and the effect of the glycolipids on the adhesion of neutrophils to activated platelets was determined.

Structures of the various glycolipids examined are as follows: SDiY2, NeuGcα2,3Galβ1,4(Fucα1,3)GlcNacβ1,3Galβ1,4 (Fucα1,3)GlcNAcβ1,3Galβ1,4Glcβ1,1Cer; SLe$^x$, NeuGcα2,3Galβ1,4 (Fucα1,3)GlcNAcβ1,3Galβ1,4Glcβ1, 1Cer; SY2, NeuGcα2,3Galβ1,4 GlcNAcβ1,3Galβ1,4 (Fucα1,3)GlcNAcβ1,3Galβ1,4Glcβ1,1Cer; SH, NeuGcα2, 3Galβ1,4GlcNAcβ1,3Galβ1,4GlcNAcβ1,3Galβ1,4Glcβ1, 1Cer; SPG, NeuGcα2,3Galβ1,4GlcNAcβ1,3Galβ1,4Glcβ1, 1Cer.

The results of two identical experiments are shown in Table 3.

TABLE 3

| GLYCOLIPID | AMOUNT REQUIRED FOR 50% INHIBITION (µM) |
|---|---|
| SY2 (Exp 1) | 0.325 |
| SY2 (Exp 2) | 0.345 |
| SLe$^x$ (hexa) | 0.30 |
| SdiY2 | 0.36 |
| SPG | No Inh. |
| SH | No Inh. |

These results show that SY2 inhibited P-Selectin mediated adhesion of neutrophils to thrombin activated platelets equally as well as did SLe$^x$ and SDiY2.

EXAMPLE 9

Blocking adhesion using further variants of SLe$^x$

The example demonstrates that the affinity of sialylated Le$^x$ (SLe$^x$) for P-Selectin is the same whether the terminal sialic acid is in the form N-Acetyl neuraminate (NeuAc) or N-Glycol neuraminate (NeuGc). All materials were prepared as described above. Platelets and neutrophils were isolated by the methods described. Platelets were activated with thrombin and then incubated with dilutions of various glycolipids contained in liposomes. Neutrophils were added and the effect of the glycolipids on the adhesion of neutrophils to activated platelets was determined.

The results of an experiment in which synthetic SLe$^x$ (NeuAc) and a preparation of SLe$^x$ prepared by enzymatic fucosylation of sialylparagloboside purified from bovine erythrocytes, SLe$^x$(NeuGc), were directly compared are shown in Table 4.

TABLE 4

| GLYCOLIPID SOURCE | | AMOUNT REQUIRED FOR 50% INHIBITION (µM) |
|---|---|---|
| SLe$^x$ (NeuGc) | (Bovine Erythrocytes) | 0.74 |
| SLe$^x$ (NeUAc) | (Synthetic) | 0.67 |

These results show that SLe$^x$-hexasaccharide inhibited P-Selectin mediated adhesion of neutrophils to thrombin activated platelets equally well whether the sialic acid was NeuAc or NeuGc. This result indicates that either the N-acetyl or N-glycollyl derivative of sialic acid are recognized by P-Selectin. Similar results have been obtained with ELAM-1.

Various glycolipids were also tested in the same assay. Structures of the glycolipids tested are as follows: SLe$^x$ (hexa), NeuGcα2,3Galβ1,4(Fucα1,3)GlcNacβ1,3Galβ1,4 4Glcβ1,1Ceramide; α2,3 SLe$^x$ cer, NeuAcα2,3Galβ1,4 (Fucα1,3) GlcNAcβ1,3Galβ1,4Glcβ1,1Ceramide; α2,6 SLe$^x$ cer, NeuAcα2,6Galβ1,4(fucα1,3)GlcNacβ1,3Galβ1, 4Glcβ1,1Ceramide; SH, NeuGcα2,3Galβ1,4 GlcNAcβ1, 3Galβ1,4GlcNAcβ1,3Galβ1,4Glcβ1,1Ceramide.

EXAMPLE 10

Blocking adhesion using synthetic SLe$^x$

This example demonstrates that synthetic SLe$^x$ binds ELAM-1 and inhibits neutrophil adhesion to activated endothelium. This example also shows that the linkage of the sialic acid affects binding to ELAM-1.

Two synthetic compounds were prepared. One comprised sialic acid in an α2,3 linkage, as in naturally occurring SLe$^x$. The second comprised sialic acid in an α2,6 linkage, to examine the importance of the nature of the linkage to receptor binding.

Liposomes were prepared by adding 12 µl of absolute ethanol (ETOH) to each tube, warming briefly in a 50° C. water bath and sonicating for 2 min. 238 µl of warm phosphate buffered saline (PBS) was added slowly to each tube while sonicating and sonication was continued for a further 10 min. The final concentration of stock liposomes was 400 µg glycolipids/ml in 5% ETOH/PBS.

Procedure

1. HUVECs, PMNs, and liposomes were prepared as described above.
2. The stimulated HUVEC assay plate was removed from the incubator and the wells were washed two times with RPMI 1640 containing 5 mg/ml bovine serum albumin (BSA).
3. Liposomes stocks were diluted in the HBSS/BSA buffer to make solutions equal to: 40 µg/ml, 30 µg/ml, 15 µg/ml, 7.5 µg/ml, 3.75 µg/ml and 1.87 µg/ml. Similar dilutions were prepared from a control stock consisting of PBS-5% ETOH.
4. The medium was removed from the wells of the assay plate with a pasteur pipette, a few wells at a time.
5. 0.05 ml of each liposome suspension was added to duplicate wells on the stimulated assay plate. Control wells received the liposome buffer containing ethanol HBSS and BSA at the same concentrations as in the liposome containing wells. Control buffer was plated on unstimulated and stimulated HUVEC. Liposome containing samples were added to stimulated wells only.

6. The plates were incubated for 40 min at 37° C. and then 50 μl of PMNs were added to the assay wells. The final concentration of cells was 5×10$^5$ well in 100 μl.
7. The assay plate was returned to the incubator (5% $CO_2$, 37° C.) for 8 min.
8. Unbound cells were removed from the wells of the assay plates by systematic resuspension using a P200 multichannel pipette followed by addition and removal of 0.2 ml of medium.
9. All of the medium was removed from the wells and 50 μl of solubilization buffer was added. This consisted of citrate buffer (24.3 ml of 0.1M Citric acid, 10.5 g/500 ml+25.7 ml of 0.2M dibasic sodium phosphate, 14.2 g/500 ml and SQ $H_2O$ to 100 ml) containing 0.1% NP-40 detergent.
10. The plate was incubated on a rotary shaker for 10 min and then 0.05 ml of OPDA solution [8 mg o-phenylene-diamine, Sigma cat# P-1526, 8 μl of 30% $H_2O_2$ and 10 ml of citrate buffer (as above)] was added to each well. The reaction was allowed to develop for 15 min and then 25 μl of 4N $H_2SO_4$ was added to each well to stop the reaction.
11. A reagent bulk was prepared by mixing 100 μl volumes of the solubilization buffer and the OPDA solution with 50 μl of 4N $H_2SO_4$.
12. 100 μl of supernatant was removed from each of 2 wells and transferred to a flexible ELISA assay plate (Falcon). The plate was scanned spectrophotometrically at 492 nm within 30 min.

The results of the two experiments are presented in Table 5, below.

TABLE 5

| | Concentration | (2,6) SLe$^x$ Mean | (2,3) SLe$^x$ Mean |
|---|---|---|---|
| 1 | 20 μg/ml | 0.663 | 0.156 |
| 2 | 15 μg/ml | 0.636 | 0.270 |
| 3 | 7.5 μg/ml | 0.602 | 0.359 |
| 4 | 3.75 μg/ml | 0.655 | 0.483 |
| 5 | 1.87 μg/ml | 0.690 | 0.580 |
| 6 | 0.47 μg/ml | 0.695 | 0.642 |
| 7 | 0 μg/ml | 0.710 | 0.716 |

| | Concentration | Control +IL-1B Mean | Control −IL-1B Mean |
|---|---|---|---|
| 1 | 20 μg/ml | 0.657 | 0.010 |
| 2 | 15 μg/ml | 0.740 | 0.010 |
| 3 | 7.5 μg/ml | 0.658 | 0.013 |
| 4 | 3.75 μg/ml | 0.698 | 0.009 |
| 5 | 1.87 μg/ml | 0.725 | 0.014 |
| 6 | 0.47 μg/ml | 0.782 | 0.018 |
| 7 | 0 μg/ml | 0.708 | 0.016 |

Figure 9:
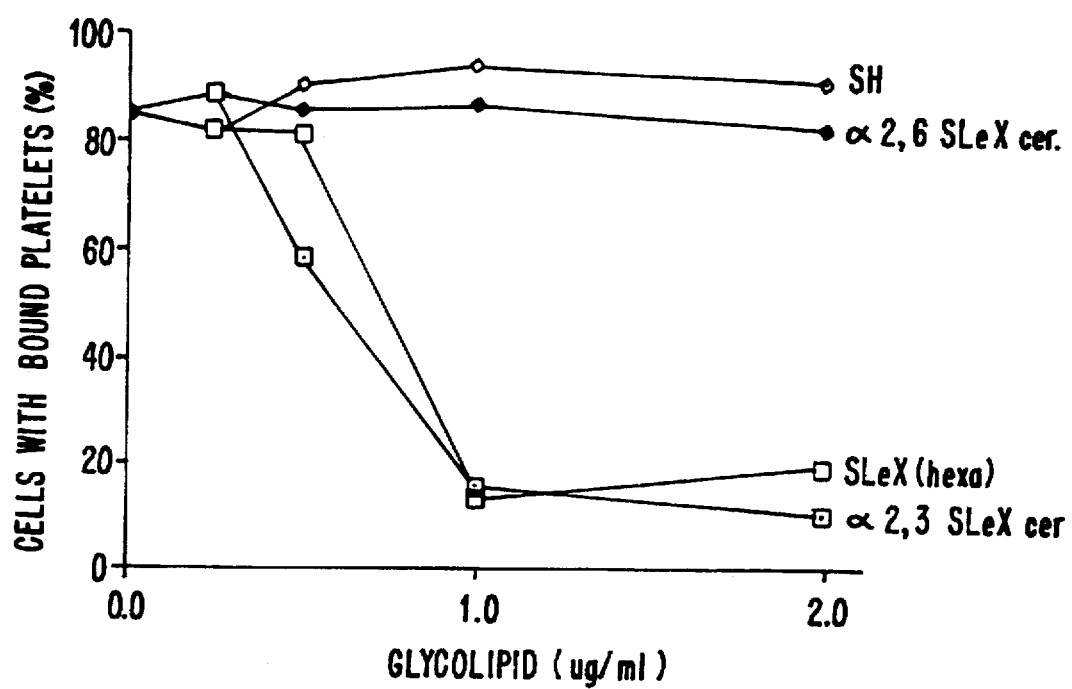
FIG. 9 shows inhibition of P-Selectin mediated adhesion by glycolipids that have either NeuAc or NeuGc as the terminal sialic acid.

These results show that liposomes containing synthetic α(2,3)SialylLe$^x$ but not α(2,6)SialylLe$^x$ inhibit neutrophil adhesion to activated endothelium in an E-Selectin dependent binding assay. Thus, the α2,3 linkage of the sialic acid appears to be necessary for recognition by ELAM-1. In addition, the results show that a synthetically produced oligosaccharide, α(2,3)SialylLe$^x$, binds to ELAM-1 and blocks binding of neutrophils to activated endothelium. Similar results were found with P-Selectin and are presented in FIG. 9. The SLe$^x$ compound, or derivatives of this compound, therefore constitute potential anti-inflammatory drug candidates.

EXAMPLE 11

Treatment of HL60 Cells with Endo-β-Galactosidase

This example describes experiments to determine whether the internal β-galactose-backbone sugar linkage of sialylated Le$^x$ of HL60 cells was susceptible to cleavage by endo-β-Galactosidase, an enzyme known to cleave an internal β-galactose linkage in polylactosaminyl structures, but not β-gal when GlcNAc is attached to mannose (core-type structures).

Procedure

Platelets were isolated and activated with thrombin by the methods described above. Il-1β activated HUVEC were prepared as described above. Cultured HL60 cells were treated with endo-β-galactosidase as described below and the effect of enzyme treatment on the P-Selectin mediated adhesion of HL60 cells to activated platelets was determined.

Enzyme treatment of the HL60 cells was carried out as follows: 12.4×10$^6$ cells were washed twice with Hanks Balanced Salt Solution containing 20 mM HEPES and 0.2% glucose, followed by a single wash step in normal saline. The endo-β-galactosidase (0.1 Unit, ICN Chemicals, Inc., Irvine, Calif.) was dissolved in 200 μl normal saline and 200 μl sodium acetate buffer, pH 6.01. 200 μl (containing 0.05 U of enzyme) was added to 3×10$^6$ HL60 cells, and 200 μl of the acetate buffer was added to a similar number of cells to be used as the buffer control. Both tubes were incubated at 37° C. for 60 min. with gentle shaking. The tubes were then cooled in ice and the cells were washed three times in HBSS containing HEPES and glucose and were then counted and suspended to 2×10$^6$/ml.

For the P-Selectin assay, 20 μl of Tyrode-HEPES buffer, pH 7.2 was placed in a microcentrifuge tube. The same volume of activated platelets (2×10$^8$/ml) and HL60 cells (2×10$^6$/ml) was added and, after mixing, the tubes were allowed to stand at room temperature for 20 min. Adhesion of platelets to the HL60 cells was assessed microscopically as described earlier for adhesion of activated platelets to neutrophils.

For the E-Selectin assay, enzyme treatment of the HL-60 cells was performed as described above, except that the cells were simultaneously labeled with $^{51}$CR as previously described. E-Selectin mediated adhesion was arrested by incubating 2×10 treated or untreated cells with IL-1 activated HUVEC for 30 minutes at 4° C. and then washing the plate with a pasteur pipette.

The results of these experiments indicated that treatment of HL60 cells with endo-β-Galactosidase inhibited their ability to bind to (1) thrombin activated platelets by 87.5% and (2) IL-1β activated HUVEC at 40° C. by 70%. Thus, the minimal SLe$^x$-containing tetrasaccharide ligand for P-Selectin is probably attached to a lactose or polylactosaminyl structure rather than a mannose.

EXAMPLE 12

Fucosylated Polysaccharide blocks binding of Neutrophils to Platelets

In this example the ability of a fucosylated polysaccharide to inhibit P-Selectin mediated adhesion was compared to that of the non-fucosylated polysaccharide, a hexasaccharide SLe$^x$ and Le$^x$. Briefly, platelets and neutrophils were isolated by the methods described above. Platelets were activated with thrombin and then incubated with dilutions of various oligosaccharides. Neutrophils were added and the effect of the saccharides on the adhesion of neutrophils to activated platelets was determined. The oligosaccharides used were as follows: Native polysaccharide and its fucosylated derivative (the preparation of both is described, below); SLe$^x$ hexasaccharide, LNF III (Le$^x$) and LNF I.

The conversion of a polysaccharide which contains the linear core structure of SLe$^x$ into a polyvalent SLe$^x$ containing polysaccharide was achieved by enzymatic fucosylation. The native polysaccharide type Ia was obtained from Group B Streptococcus as described by Jennings et al., Biochem. 22 1258-1263 (1983) which is incorporated herein by reference. The appropriate bacterial strains are deposited with the American Type Culture Collection and have Deposit Nos. 12400, 31574, 12401, and 31575.

To prepare the fucosylated polysaccharide, the native type Ia polysaccharide (1 mg) was dissolved in a mixture of 6 μl of 1M manganese chloride, 90 μl of water containing 0.9 μmoles of guanosine 5'-diphosphate-β-L-fucose with a radiolabelled tracer (specific activity 1.82×10$^6$ cpm/μmole), and 137 μl of water. To this was added 100 μl of a solution of 1,3/1,4 fucosyl transferase isolated from human milk as previously described by Prieels et al., J. Biol. Chem. 256 10456-10463 (1981), which is incorporated herein by reference.

The reaction mixture was concentrated against a membrane (100K cut off) several times with water and the retentate lyophylized to give a powder. This solid was dissolved in water and passed through a weak cation exchange column to remove any remaining protein. The radioactive fractions containing the fucolsylated polysaccharide were collected and lyophilized. Approximately fifty of the available side chains were fucosylated as measured by the incorporation of the radiolabel.

Procedure

Platelets were isolated as described above and were activated (2×10$^8$/ml) by incubation for 20 min at room temperature with thrombin at a final concentration of 0.25 U/ml.

Neutrophils were isolated by layering heparinized blood over Mono-Poly Resolving Medium (Ficoll-Hypaque, Flow Laboratories), followed by centrifugation for 25 min at 20 rpm and then, a further 25 min at 2500 rpm as described above.

For the assay, 20 μl of the platelet suspension (2×10$^8$/ml) was placed in an Eppendorf centrifuge tube. An equal volume of the oligosaccharide preparations at concentrations from 500 μg/ml to 2.0 μg/ml was added and the tubes were allowed to stand at room temperature for 20 min. Twenty μl of the neutrophil preparation (2×10$^6$/ml) was then added and the tubes were allowed to stand for a further 20 min at room temperature.

Adhesion of activated platelets to the neutrophils was assessed microscopically. One hundred neutrophils were evaluated. They were scored as positive if 2 or more platelets were attached and negative if less than 2 platelets were bound. The percent of cells with 2 or more bound platelets was calculated.

As shown in Table 6, the fucosylated polysaccharide very efficiently inhibited P-Selectin mediated binding of neutrophils to thrombin activated platelets-50% inhibition was achieved with less than 1 μg/ml. This compared to 2 μg/ml which was required of the native polysaccharide and 8 μg/ml of the SLe$^x$ hexasaccharide for a similar degree of inhibition.

TABLE 6

| OLIGOSACCHARIDE | AMOUNT REQUIRED FOR 50% INHIBITION (μM) |
|---|---|
| Native Polysaccharide | 15 |
| Fucosylated Polysaccharide | 0.7 |
| SLe$^x$ Hexasaccharide | 8 |
| LNF III (Le$^x$) | 35 |
| LNF I | No Inhibition |

EXAMPLE 13

Protection of Rats from Endotoxic Shock (Lethality) by Monoclonal Antibody to E-Selectin This example demonstrates the efficacy of mAb P6E2 (a murine IgG3k, functional anti-human E-Selectin mAb, described in copending application U.S. Ser. No. 07/645,878, which is incorporated herein by reference) in an animal model of lipopolysaccharide-induced death. A rat system was chosen because P6E2 has been shown to cross-react with the rat equivalent to E-Selectin.

Materials and Methods

LPS from E. coli 0111:B4 (Sigma) was prepared fresh from a single lot one day prior to use by dissolving in sterile, pyrogen-free saline at a concentration of 5 mg/ml. The solution was sonicated on ice for 30 seconds using a Tekmark Sonic disrupter. Just prior to use, the material was sonicated a second time for 30 seconds.

Female Lewis rats' weighing 200 g (±10 g) were purchased from Charles River Breeding Labs and held for at least 7 days after receipt (for adaptation). Groups (10 animals) were used, unless otherwise noted. All reagents were injected parenterally via tail vein. As negative controls, animals received either sterile, LPS-free saline, or a murine IgG3k myeloma protein (J606, low pyrogen—<2 ng/mg protein).

Results

The P6E2 dose/schedule protocols were empirically derived from the pharmacokinetic data we obtained with P6E2 prophylactically administered to rats. A "minimal" LD$_{100}$ dose was empirically determined to be 7.5 mg/kg for these rats.

In one experiment, rats were treated with 10 mg/kg of P6E2 one hour before the LPS challenge. A boost was administered 3 hours after the challenge. 4/10 treated animals survived the LPS challenge. In contrast, all 10 (saline-injected) controls died. At the twenty-four hour observation period, the survivors showed few of the clinical signs characteristic of LPS-treated animals.

Figure 10:
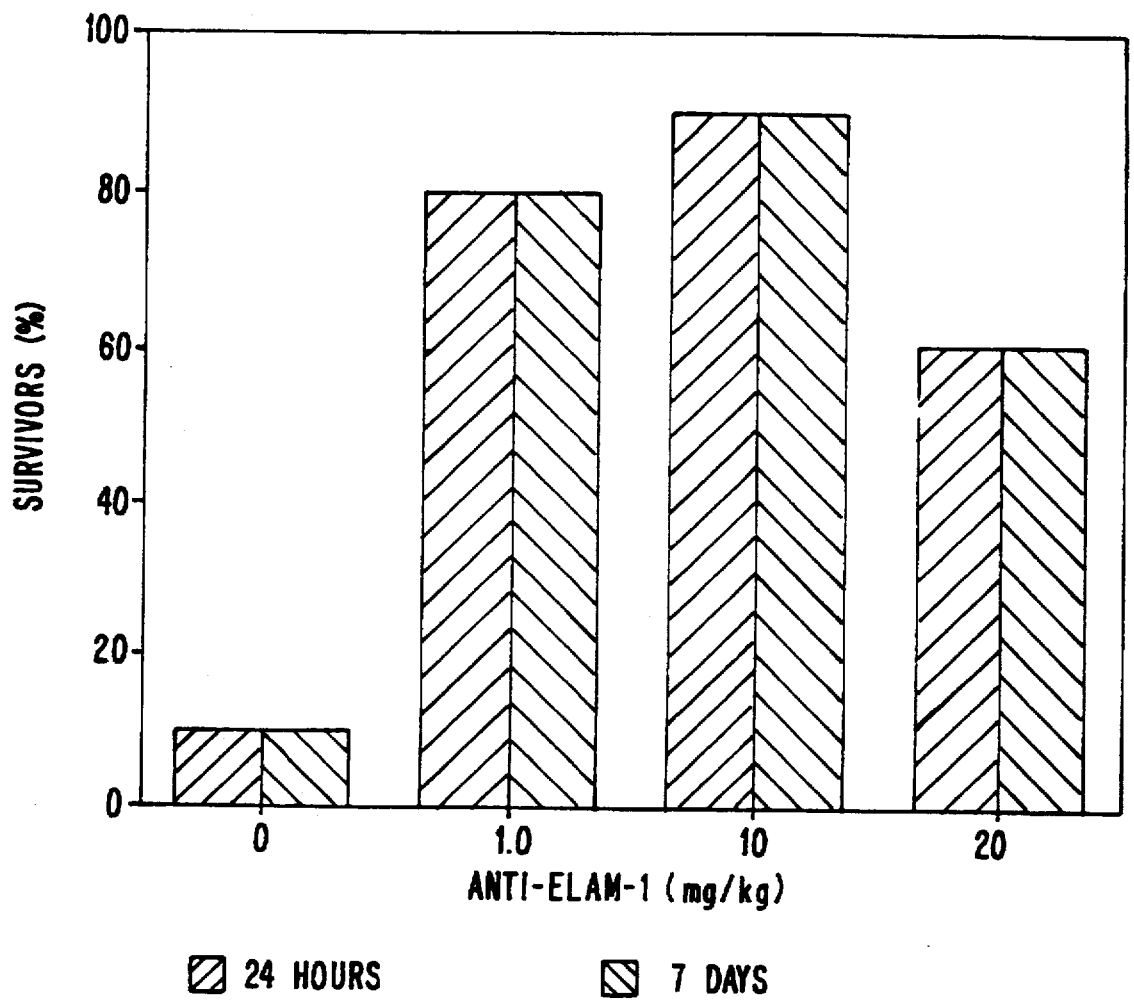
FIG. 10 shows prophylactically administered monoclonal antibodies against E-Selectin prevent lipopolysaccharide induced death in rats.

Doses of P6E2 which were (1) 2-fold higher and (2) an order of magnitude lower than the 10 mg/kg dose used in the first experiment were also tried. The results show that P6E2 had a significant effect: 80% of the animals survived at the 10 mg/kg dose (FIG. 10). Note that one animal survived in the saline control group—suggesting that this group of animals was not "hit" as hard.

Another study was performed to demonstrate the therapeutic value of P6E2. Animals received the 10 mg/kg iv bolus dose of P6E2 at 1 hour before, or 2, 4, or 6 hours after the LPS challenge.

Figure 11:
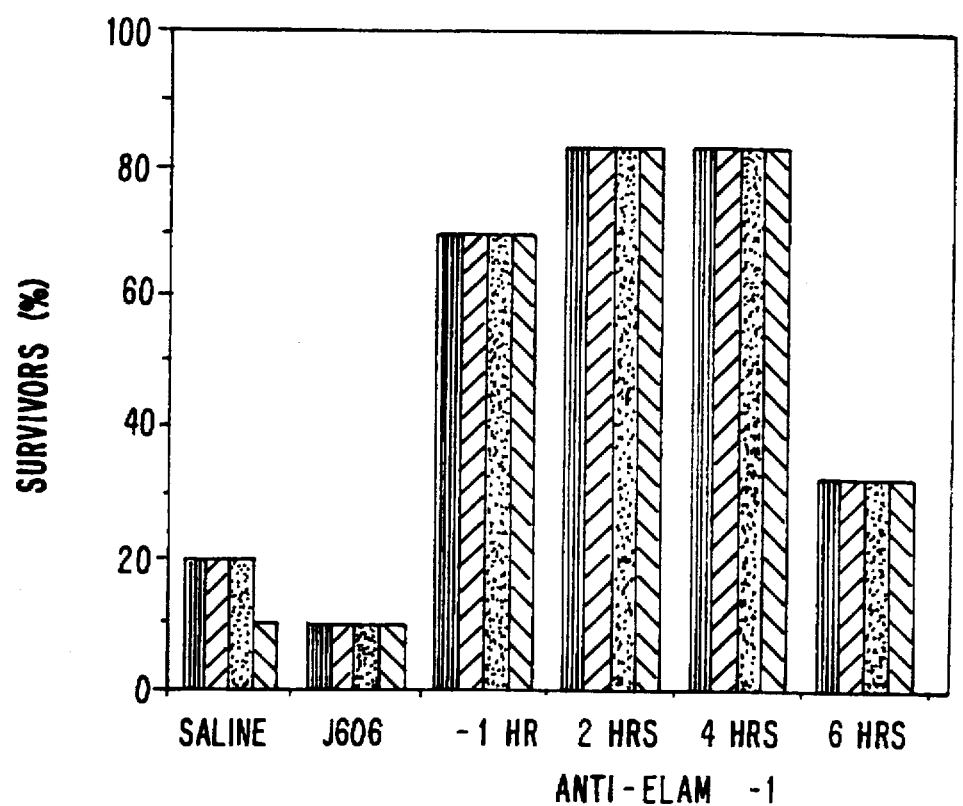
FIG. 11 shows therapeutically administered monoclonal antibodies against E-Selectin prevent lipopolysaccharide induced death in rats.

Once again, 1 of 10 animals survived in the saline-treated group, as well as in a group treated with 10 mg/kg J606 myeloma protein at T=−60 minutes (FIG. 11). P6E2 had a protective effect even when administered 2 or 4 hours after LPS.

Conclusion

The protection seen with Cytel mAb P6E2 demonstrates of the importance of E-Selectin in an animal model of a lethal disease.

EXAMPLE 14

Rolling of SLe$^x$ Liposomes on IL-1 Activated Rabbit Endothelial Cells

This example demonstrates that sialylated Lewis x (SLe$^x$) and sialoparagloboside (SPG) isolated from biological sources and incorporated into liposomes will "roll" along activated rabbit venules.

"Rolling" is an early intercellular interaction between leukocytes and the endothelial cell wall. A leukocyte will "roll" on endothelial cells. The leukocyte will then either (1) be released back into circulation, or (2) adhere to the endothelial cell, and begin the early events that culminate in inflammation. Selectins have been implicated in the cell-cell interactions of "rolling."

Materials

Liposomes containing the glycosphingolipids were formed as follows: 50 μg of glycolipid was added to 150 μg phosphatidylcholine (Sigma, egg yolk), 250 μg cholesterol (Sigma) and 1 mM carboxyfluorescein (Sigma) in chloroform:methanol (2:1) and the whole solution evaporated to dryness in glass screw cap tubes. Liposomes were prepared by adding 12.5 μl of absolute ethanol to each tube, warming briefly in a water bath and sonicating for 2 minutes. 238 μl of warm PBS was added slowly to each tube while sonicating and sonication was continued for a total of 10 minutes. The liposomes were brought to 1 ml with PBS and centrifuged at 14,000 rpm for 2 minutes to remove excess EtOH and carboxyflourescein. The supernatant was discarded and the liposomes resuspended in 1 ml PBS, counted on a hemacytometer and adjusted to 5×10$^6$ liposomes per ml. One ml was injected into the rabbit, which was activated 4 hours earlier with IL-1.

Rolling was observed using intravital microscopy as described by von Andrian et al., *Proc. Natl. Acad. Sci. USA* 88:7538–7542 (1991), which is incorporated herein by reference. IL-1-activated rabbit mesentery was exteriorized and spread on a 37° C. heated glass window over a microscopic stage. The mesentery was bathed with 36.5° C. saline solution equilibrated with 5% CO$_2$ in N$_2$. Liposome-endothelial interactions were observed with an intravital microscope with a 5× salt water immersion objective. Liposomes were visualized by exposure to fluorescent light. The liposomes in a segment of selected mesentery venule (20–40 μm in diameter) were counted for one minute.

Results

Liposome Rolling on IL-1 Activated Rabbit Cells

| material injected | rolling |
|---|---|
| human neutrophils | 4 (maximum amount of rolling) |
| SLe$^x$ liposomes | 2 |
| SPG liposomes | 0 (no rolling) |

Conclusion

E-Selectin and its ligand appear to be involved in the rocess of leukocyte margination or "rolling".

EXAMPLE 15

Preparation of pentasaccharide Z

This example describes the synthesis of a preferred pentasaccharide, Z. The structure of the intermediate compounds and the final product are shown in FIG. 12A. Each intermediate compound is identified by Roman numerals I through X.

Preparation of Ethyl β-D-galactopyranoside (I)

A solution of 2,3,4,6-tetra-O-acetyl-galactosyl bromide (2.5 kg) in dichloromethane (4 L) was added at a rate of 20–25 mL/min to a reactor charged with silver carbonate (3.13 kg, 11.4 mol), 4A molecular sieves (2.37 kg), dichloromethane (16 L), and anhydrous ethanol (4.0 L). Agitation was maintained to provide vigorous mixing of the reagents. Two hours after complete addition of the bromide solution, TLC on silica gel developed with hexane:ethyl acetate (1:1) showed no bromide present. At that time the reaction mixture was filtered through a celite pad (1 kg), and the filtrate was evaporated at 30°–35° C. under vacuum to give a brown oil (1.95 kg). This oil was dried under vacuum for 17 hours. $^1$H NMR (CDCL$_3$) δ: 5.36 (1H, d, J$_{3,4}$=3.7 Hz, H-4), 5.17 (1H, dd, J$_{2,3}$=11.0 Hz, H-2), 4.99 (1H, dd,H-3), 4.46 (1H, d, J$_{1,2}$=8.3 Hz, H-1), 2.15, 2.05, 2.04, 1.95 (12H, 4s, OAc), 1.21(3H, t, OCH$_2$CH$_3$).

The crude ethyl tetraacetyl galactopyranoside (1.95 kg) was dissolved in anhydrous methanol (11.7 L) and a 25% sodium methoxide in methanol solution (90 mL) was added dropwise. The solution was stirred for one hour at which time TLC on silica gel developed with ethyl acetate:methanol (2:1) showed no starting material to be present. The product had an R$_f$=0.6. The solution was neutralized by the addition of Amberlite IR-120(H$^+$) resin (0.6 kg) with stirring. When the solution pH was between pH 6 and pH 7, the resin was removed by filtration and the filtrate was evaporated under vacuum to afford a pale yellow solid. This solid was dissolved in boiling ethanol (11 L). The resulting solution was allowed to cool to 25° C. and then cooled to 0° C. to give a white recipitate. Filtration of this solid gave ethyl β-D-galactopyranoside (0.851 kg). $^1$H NMR (D$_2$O) δ: 4.38 (1H, d, J$_{1,2}$=8.0 Hz, H-1), 3.89 (1H, bd, J$_{3,4}$=3.7 Hz, H-4), 1.2 (3H, t, OCH$_2$CH$_3$).

Preparation of Ethyl 4,6-O-benzylidene-β-D-galactopyranoside (II)

Ethyl β-D-galactopyranoside (I) (0.851 kg, 4.09 mol) was charged into a 20 L rotovap flask with toluene sulfonic acid (1.5 g, 7.9 mmol). The evaporator flask was fixed to the evaporator, benzaldehyde dimethyl acetal (1.23 L, 8.18 mol) was added by aspiration and the mixture was tumbled for 4 hours. Between thirty and forty minutes after addition of the acetal, near complete solution was obtained followed rapidly by the appearance of a heavy precipitate. Rotation was continued for 4 hours at which time triethylamine (1.5 mL) was added to neutralize the reaction mixture. A vacuum was applied and the solvent was removed to give a solid mass. Hexane (6 L) was charged into the flask and the mixture tumbled for 0.5 hours. The resulting solid was filtered and washed on the filter with hexane:ethyl ether (1:1, 2 L). The white solid so obtained was dried under vacuum for 17 hours to give pure ethyl 4,6-O-benzylidene-β-D-galactopyranoside (1.0 kg, 3.38 mol) in 83% yield. 1H NMR (CDCl$_3$) δ: 7.53 (2H, m, aromatics), 7.37 (3H, m, aromatics), 5.57 (1H, s, CHPh), 4.29 (1H, d, J$_{1,2}$=7.0 Hz, H-1), 4.21 (1H, d, J$_{3,4}$=3.27 Hz, H-4), 1.29 (3H, t, OCH$_2$CH$_3$).

Preparation of Ethyl 2-O-benzoyl-4,6-O-benzylidene-β-D-galactopyranoside (III)

Ethyl 4,6-O-benzylidene-β-D-galactopyranoside (II) (0.924 kg, 3.12 mol) was put into a 20 liter reactor equipped with an air drive, a pressure equalizing addition funnel with gas inlet, cooling bath, and a gas outlet. Before sealing the flask, dichloromethane (9.3 L) and pyridine (2 L) were added which gave a homogeneous solution. The addition funnel was charged with chloroacetyl chloride (0.388 kg, 3.43 mol, 273 mL) as a 60% solution in dichloromethane. The flask was sealed and a low flow of dry nitrogen was begun. The bath was cooled to −65°±5° C. and the reaction mixture was stirred for 30 minutes. At that time dropwise addition of the acyl chloride solution was begun at a rate of 3–4 mL per minute. After complete addition of this solution the reaction mixture was maintained at −65°±5° C. for an additional 1 hour. At that time benzoyl chloride (0.614 kg, 4.37 mol, 0.507 L) was added to the reaction mixture at a rate of 8–12 mL per minute. The reaction mixture was allowed to warm to room temperature and left for 17 hours. The reaction mixture was filtered to remove precipitated salts and the filtrate was concentrated in vacuo to remove most of the dichloromethane. A small sample was set aside for NMR. $^1$H NMR (CDCl$_3$) δ: 5.75 (1H, dd, J$_{2,3}$=10.6 Hz, H-2), 5.56 (1H, s, CHPh), 5.25 (1H, dd, J$_{3,4}$=3.44 Hz, H-3), 4.69 (1H, d, J$_{1,2}$=8.48 Hz, H-1), 4.48 (1H, bd, H-4), 1.15 (3H, t, OCH$_2$CH$_3$). Water (180 mL) was added to the concentrate and the resulting mixture was agitated for two hours at 40° C. At that time the reaction mixture was further concentrated to give a yellow residue that was dissolved in dichloromethane (11 L) and transferred to a 50 liter extractor. The organic solution was successively extracted with ice cold aqueous 0.5N HCl (11 L), aqueous saturated sodium hydrogen carbonate (11 L), cold water (11 L), and the organic layer was dried over anhydrous sodium sulfate (1.0 kg), filtered, and the filtrate evaporated to give a yellow solid which was dried under high vacuum. This reaction was monitored by TLC on silica gel developed with hexane:ethyl acetate (1:1). This solid was dissolved in hot ethanol (9.5 L) which after cooling and filtration gave ethyl 2-O-benzoyl-4,6-O-benzylidene-β-D-galactopyranoside (0.737 kg, 1.85 mol) in 59% yield. $^1$H NMR (CDC$_3$) δ: 5.59 (1H, s, CHPh), 5.36 (1H, dd, J$_{2,3}$=10.07 Hz, H-2), 4.64 (1H, d, J$_{1,2}$=8.21 Hz, H-1), 1.15 (3H, t, OCH$_2$CH$_3$).

To confirm that the benzoate is at the C-2 and that C-3 carries a free hydroxyl group, a drop of trichloroacetyl isocyanate was added to the NMR sample and the spectrum was reacquired. This spectrum contained a low field doublet of doublets at δ=5.27 typical of H-3 of galactose which is esterified at C-3. The original filtrate obtained from the reaction mixture contains additional quantities of product.

Preparation of Ethyl 2-O-benzoyl-4,6-O-benzylidene-3-O-(3,4,6-tri-O-acetyl-2-deoxy-2-phthalimido-β-D-glucopyranosyl)-β-D-galactopyranoside (IV)

Ethyl 2-O-benzoyl-4,6-O-benzylidene-β-D-galactopyranoside (III) (1.001 kg, 2.5 mol) was placed in a 20 L reactor that was equipped with a cooling bath, pressure equalizing addition funnel with gas inlet, agitator, and gas outlet. 4A Molecular sieves (1.03 kg), dichloromethane (6.6 L), collidine (0.367 L, 2.77 mol), and, after 15 min stirring, finally silver trifluoromethanesulfonate (0.689 kg, 2.641 mol) were added to the flask under a nitrogen flow. The addition funnel was charged with a solution of 3,4,6-tri-O-acetyl-2-deoxy-2-phthalimido-β-D-glucopyranosyl bromide (1.310 kg, 2.641 mol) dissolved in dichloromethane (2.40 L). The system was sealed and a low purge of nitrogen was maintained and agitation begun, first at room temperature for 1 hr, then cooling (−25° C.) of the reaction vessel was begun and the mixture was stirred at low temperature for another hour. The bromide solution was then added over 1–2 hours. The resulting mixture was allowed to come to ambient temperature and, after 17 hours, the mixture was filtered through a celite pad and the filtrate was washed with aqueous sodium thiosulfate (2M, 3.0 L), water (3 L), hydrochloric acid (1M, 2×2 L), sodium hydrogen carbonate (1M, 3.0 L), and finally water (3 L). The organic layer was dried over anhydrous sodium sulfate, filtered, and evaporated to give a solid. The solid was dissolved in isopropanol:ethyl acetate (1:1, 32 L) at reflux. On cooling to room temperature overnight, a first crop of ethyl 2-O-benzoyl-4,6-O-benzylidene-3-O-(3,4,6-tri-O-acetyl-2-deoxy-2-phthalimido-β-D-glucopyranosyl)-β-D-galactopyranoside was obtained, after filtration and drying. Concentration of the mother liquor (18 L evaporated) and leaving the resulting solution at room temperature overnight gave a second crop of material with acceptable purity. After TLC analysis, the two crops were pooled (1.479 kg, 1.816 mol, 72%). $^1$H NMR (CDCl$_3$) δ: 7.75 (14H, m, aromatics), 5.57 (1H, s, CHPh), 5.38 (1H, dd, J=7.89 Hz, J=10.5 Hz), 5.16 (1H, t, J=9.99 Hz), 4.52 (1H, d, J$_{1,2}$=7.89, H-1), 2.08, 2.01, 1.88 (3H, 3s, OAc), 0.95 (3H, t, OCH$_2$CH$_3$).

preparation of Ethyl 3-O-(2-N-allyloxycarbonyl-2-amino-2-deoxy-β-D-crucopyranosyl) -β-D-calactopyranoside (V)

To ethyl 2-O-benzoyl-4,6-O-benzylidene-3-O-(3,4,6-tri-O-acetyl-2-deoxy-2-phthalimido-β-D-glucopyranosyl)-β-D-galactopyranoside (IV) (1.017 kg, 1.25 mol) was added 80% acetic acid (10 L). The resulting mixture was heated to 90° C. for 1.25 hours, after which TLC on silica gel developed with ethyl acetate showed the product with R$_f$=0.5–0.6 and complete consumption of the starting material. The solution was evaporated to dryness, and the residue was dissolved in 1:1 ethanol:acetone (6 L) at 70° C. Deionized water (9.0 L) was added to the resulting solution to precipitate the product. The product was filtered and washed with water:acetone 9:1 (6 L) and air dried for 16 hours then dried under vacuum over sodium hydroxide pellets. A second crop was isolated by adding deionized water (4.5 L) to the mother liquor. This material was dried as described above. The yield of the diol was 0.707 kg (81%). $^1$H NMR (CDCl$_3$) δ: 5.67 (1H, dd, J$_{3',4'}$=9.07 Hz, J$_{2',3'}$=11.23 Hz, H-3'), 5.57 (1H, d, J$_{1',2'}$=9.21 Hz, H-1'), 5.32 (1H, dd, J$_{2,3}$=10.08 Hz, H-2), 5.12 (1H, t, J$_{4',5'}$=9.07 Hz, H-4'), 4.46 (1H, d, J$_{1,2}$=8.64, H-1), 2.14, 2.03, 1.78 (9H, 3s, OAc), 0.98 (3H, t, OCH$_2$CH$_3$).

Ethyl 2-O-benzoyl-3-O-(3,4,6-tri-O-acetyl-2-deoxy-2-phthalimido-β-D-glucopyranosyl)-β-D-galactopyranoside (0.645 kg, 0.882 mol) was dissolved in ethanol (6.5 L) with heating to reflux and stirring. Upon obtaining a clear solution, hydrazine hydrate (0.4 L, 8.25 mol) was added and the mixture heated to reflux, with continued stirring. A precipitate began to appear and after 16 hrs reflux, the reaction was complete as judged by TLC on silica gel developed with ethyl acetate:acetic acid:methanol:water 12:3:3:2. The product had an R$_f$=0.15. The reaction mixture was cooled to ambient temperature, then acetone (5 L) was added, with stirring. Continued stirring gave a homogenous suspension which was filtered to give crude ethyl 3-O-(2-amino-2-deoxy-β-D-glucopyranosyl)-β-D-galactopyranoside, as a white, amorphous powder (0.4 kg) after drying under high vacuum in the presence of phosphorous pentoxide. This crude material was added to a mixture of methanol (5.5 L) and water (0.3 L). Sodium hydrogen carbonate (0.90 kg, 10.7 mol) was added, and the mixture was stirred for 30 min. At that time allyl chloroformate (0.140 L, 1.32 mol) was added, with continued stirring at room temperature. After 1 hour TLC on silica gel developed with ethyl acetate:acetic acid:methanol:water, 12:3:3:2 showed the product with $R_f$=0.6 and the reaction to be complete. The mixture was filtered, and the solid was washed with methanol (0.5 L). The filtrate was evaporated to give a residue. The residue was taken up in water (3.0 L) and extracted with dichloromethane (4.0 L). The aqueous layer was separated and washed with dichloromethane (1.0 L) and concentrated to give a solid. The solid mass was stirred vigorously for 2 hours with acetone:ethyl acetate (1:2, 3 L). The suspension was filtered and the solid was washed with ethyl acetate. Drying under high vacuum in the presence of phosphorous pentoxide for 17 hours gave an off-white powder (0.444 kg). $^1$H NMR (D$_2$O) δ: 5.93 (1H, m, OCH$_2$CH=CH$_2$), 5.35–5.17 (2H, m, OCH$_2$CH=CH$_2$), 4.67 (1H, d, $J_{1',2'}$=8.13 Hz, H-1'), 4.35 (1H, d, $J_{1,2}$=8.10 Hz, H-1), 4.09 (1H, d, $J_{3,4}$=3.0 Hz, H-4), 1.19 (3H, t, OCH$_2$CH$_3$).

Preparation of Ethyl (β-D-Galactopyranosyl)-(1-4)-
O-(2-N-allyloxycarbonyl-2-deoxvy-β-D-
glucopyranosyl)-(1-3)-O-β-D-galactopyranoside
(VI)

This step describes the synthesis of a trisaccharide with a N-phthalimido-lactosyl halide which is a suitable acceptor for enzymatic sialylation.

To a mixture of ethyl 2-O-benzoyl-4,6-O-benzylidene-β-D-galactopyranoside (III) (0.76 g, 1.9 mmol), 4A molecular sieves (2 g), dichloromethane (10 mL), collidine (0.278 mL, 2.1 mmol), and silver trifluoromethanesulfonate (0.522 g, 2 mmol) cooled to −25° C. was added dropwise a solution of 4-O-(2,3,4,6-tetra-O-acetyl-β-D-galactopyranosyl)-3,6-di-O-acetyl-2-deoxy-2-phthalimido-β-D-glucopyranosyl chloride (1.484 g, 2 mmol) dissolved in dichloromethane (5 mL). The resulting mixture was stirred and warmed to ambient temperature after complete addition of the chloride. After 2 hours the mixture was diluted with dichloromethane and filtered. The filtrate was washed successively with aqueous sodium bisulfite, aqueous hydrochloric acid, aqueous sodium hydrogen carbonate, and finally water. The organic layer was dried over anhydrous sodium sulfate, filtered and evaporated to give a solid mass that was recrystallized from dichloromethane:hexane. The fully blocked trisaccharide (0.66 g) was treated with 80% acetic acid (5 mL) at 80° C. for 2 hours at which time the solvent was removed by evaporation. The residue was coevaporated with toluene-ethyl acetate two times to give a residue which was dissolved in ethanol (10 mL). Hydrazine hydrate (0.3 mL) was added and the resulting mixture was refluxed for 17 hours to give a precipitate which was filtered to give a solid (0.45 g) after drying. This solid was dissolved in methanol:water 5:1 and treated with diallylpyrocarbonate (0.166 mL) for 1 hour. The resulting mixture was evaporated and partitioned between dichloromethane and water. The aqueous layer was separated and concentrated to give a residue which solidified upon trituration with ethyl acetate:acetone (4:2).

This provided the title trisaccharide (VI) which was enzymatically sialylated to give ethyl (sodium (5-acetamido-3,5-dideoxy-α-D-glycero-D-galacto-nonulopyranosylonate))-(2-3) -O-(β-D-galactopyranosyl)-(1-4)-O-(2-N-allyloxycarbonyl-2-deoxy-β-D-glucopyranosyl)-(1-3)-O-β-D-galactopyranoside (VII) which was identical to that produced in the following procedure.

Preparation of Ethyl (sodium (5-acetamido-3,5-
dideoxy-α-D-glycero-D-galacto-
nonulopyranosylonate))-(2-3)-O-(β-D-
galactopyranosyl)-(1-4)-O-(2-N-allyloxycarbonyl-2-
deox-β-D-glucopyranosyl)-(1-3)-O-β-D-
galactopyranoside (VII)

The following describes the enzymatic conversion of a disaccharide (V) to produce the title compound (VII) using galactosyl transferase and sialyl transferase.

To water (12 L), N-(2-hydroxyethyl)piperazine-N'-(2-ethanesulfonic acid) (0.410 kg) was added and the pH of the resulting solution was adjusted to 7.5. Bovine serum albumin (17 g) was added and the mixture stirred until a complete solution was obtained. Ethyl 3-O-(2-N-allyloxycarbonyl-2-amino-2-deoxy-β-D-glucopyranosyl)-β-D-galactopyranoside (V) (0.3 kg), glucose-1-phosphate (0.271 kg), phosphoenolpyruvate (0.177 kg), potassium chloride (0.087 kg), sodium azide (8.4 g), and uridine-5'-diphosphate (8.76 g) were added and the resulting mixture stirred until all of the solids are dissolved. Aqueous solutions of manganese chloride (1M, 506 mL) and magnesium chloride (1M, 168 mL) were then added. Pyruvate kinase (42,000U), uridine-5'-diphosphate-glucose pyrophosphorylase (2000U), inorganic pyrophosphatase (8400U), uridine-5'-diphosphate-galactose epimerase (91,000U), and uridine-5'-diphosphate-galactosyl transferase (8850U) were then added. The final volume of the reaction mixture was adjusted to 17 L with water. After 48 hours a solution of aqueous magnesium chloride (1M, 340 mL) was added. The reaction was monitored by TLC on silica gel developed with isopropanol:1M ammonium acetate 4:1. After 8–9 days TLC indicated that the reaction had proceeded to >95% at which time the following solution was prepared. A solution of N-(2-hydroxyethyl)piperazine-N'-(2-ethanesulfonic acid) (0.528 kg) was prepared in water (15 L) and the pH of the resulting solution was adjusted to 7.5. Bovine serum albumin (22 g), sodium azide (11.5 g), sialic acid (0.242 kg), phosphoenolpyruvate (0.395 kg), cytidine-5'-monophosphate (25 g), adenosine-5'-triphosphate (4.7 g), manganese chloride (1M, 780 mL) were added. To this was added pyruvate kinase (207,000U), myokinase (125,000U), cytidine-5'-monophosphate-N-acetylneuraminic acid synthetase (3245U), inorganic pyrophosphatase (9400U), and α2,3 sialyltransferase (1640U). The volume of this mixture was adjusted to 22 L and this solution was added to the galactosyl transferase reaction. The reaction was monitored by TLC on silica gel developed with isopropanol:1M ammonium acetate (4:1). After 10–12 days TLC indicates that the reaction had proceeded to give >95% of the title compound.

Preparation of Ethyl (methyl (5-acetamido-3,5-
dideoxy-4,7,8,9-tetra-O-acetyl-α-D-glycero-D-
galacto-nonulopyranosylonate))-(2-3)-O-(2,4,6-tri-
O-acetyl-β-D-galactolyranosyl)-(1-4)-O-(3,6-di-O-
acetyl-2-N-allyloxycarbonyl-2-deoxy-β-D-
glucopyranosyl)-(1-3)-O-2,4,6-tri-O-acetyl-β-D-
galactopyranoside (VIII)

An aqueous solution (40 L) of ethyl (sodium (5-acetamido-3,5-dideoxy-α-D-glycero-D-galactononulopyranosylonate))-(2-3)-O-(β-D-galactopyranosyl)-(1-4)-O-(2-N-allyloxycarbonyl-2-deoxy-β-D-glucopyranosyl)-(1-3)-O-β-D-galactopyranoside (VII) produced from the sequential action of galactosyl and sialyl transferases in the presence of the appropriate cofactors on the disaccharide (V) (0.320 kg) was filtered through paper. The filtrate was evaporated to a thick syrup in a 50 L rotavapor. The syrup was coevaporated twice with pyridine (2×2 L), then kept under vacuum for 20 hours. The evaporation flask was charged with a solution of N,N-dimethylaminopyridine (20 g) in pyridine (12 L). The rotavapor bath was charged with ice-water mixture, and rotation was continued while acetic anhydride (6 L) was added during a period of 1 hour. Two hours after complete addition more acetic anhydride (2 L) was added and the resulting mixture was left for 20 hours rotating slowly at room temperature. To ensure complete acetylation, more acetic anhydride (1 L) was added and the mixture was rotated for an additional 24 hours. The reaction was checked by TLC (ethyl acetate:hexane:ethanol, 10:10:3). Upon complete reaction vacuum was applied and 14 L of distillate collected.

To the resulting residue, methanol (15 L) was added over a period of 1 hour and the mixture was rotated at room temperature for 20 hours. At this time TLC on silica gel (ethyl acetate:hexane:ethanol, 10:10:3 and dichloromethane:acetone 3:2) showed complete conversion of the lactone to a slower-moving spot which is the methyl ester mono hydroxy compound. The mixture was then concentrated (18 L evaporated) and the mixture was cooled in ice water while acetic anhydride (3 L) was added over a period of 30 minutes. The mixture was left for 20 hours. TLC on silica gel (dichloromethane:acetone 3:2) showed complete acetylation with the product running slightly higher. Methanol (1 L) was added to destroy excess acetic anhydride during which a slight exotherm was noticed. After 1 hour, the mixture was concentrated to a syrup, which was transferred to a 50 L extractor with the aid of ethyl acetate-water mixture (13/13 L). The mixture was agitated vigorously. After phase separation, the lower aqueous layer was drawn off, and the remaining organic layer was filtered through paper. The filtrate was washed with 5% aqueous hydrochloric acid (15 L, the aqueous layer should still be strongly acidic to pH-paper after washing), and aqueous 1 M sodium bicarbonate (15 L, the aqueous layer should still be alkaline to pH paper after washing). The organic layer was then transferred to a 20 L concontainer and dried over anhydrous sodium sulfate and filtered. The filtrate was concentrated to a semi-solid residue. This residue was dissolved in dichloromethane (3 L), and applied to a silica gel column (10 kg), packed in dichloromethane. Elution first with dichloromethane (25 L), then with 3:1 dichloromethane:acetone (25 L), and finally with 1:1 dichloromethane:acetone (50 L) gave fractions containing product. Base-line separation was achieved from the disaccharide material, but very little separation was achieved from the traces of slightly faster moving material. The fractions containing product were evaporated, and redissolved in dichloromethane (1.5 L). This solution was slowly added to a vigorously stirred mixture of ethyl ether (7.5 L) and hexane (10 L). The resulting precipitate was filtered and washed with 2:1 ether:hexane, air-dried overnight, then dried in high vacuum for 48 hours. The precipitate (0.61 kg) was shown to be the title compound by NMR. $^1$H NMR contained a small amount of residual solvent (1–5%, weight/weight). $^1$H NMR (CDCl$_3$) δ: 4.67 (d, 1H, H-1''), 4.49 (d, 1H, H-1'), 4.33 (d, 1H, H-1).

Preparation of Ethyl(methyl(5-acetamido-3,5-dideoxy-4,7,8,9-tetra-O-acetyl-α-D-glycero-D-galacto-2-nonulopyanosylonate))-(2,3)-O-(3,4,6-tri-O-acetyl-β-D-galactopyranosyl)-(1,4)-O-(2-acetamido-2-deoxy-6-O-acetyl-β-D-glucopyranosyl)-(1,3)-O-(2,4,6-tri-O-acetyl-β-D-galactopyranoside
(IX)

To a solution of blocked tetrasaccharide (VIII) (0.532 kg, 0.37 mol) in dry tetrahydrofuran (8 L) was added polymethylhydrosiloxane (PMSH, 46 mL, 0.14 mol). Then Pd(PPH$_3$)$_4$ (14 g, 1.17 mmol) was added and the mixture was degassed under vacuum. The resulting reaction mixture was then stirred at room temperature for 17 hours when TLC (10:10:3, ethyl acetate:hexane:ethanol) showed completion of the reaction. To the reaction mixture was added acetic acid (36 mL, 0.55 mol) and piperidine (60 mL, 0.65 mol). The mixture was stirred at room temperature overnight until TLC (95:5, dichloromethane:methanol) showed completion of the reaction. Evaporation of solvent in vacuo gave a residue which was dissolved in dichloromethane (4 L). This solution was washed successively with water (4 L), 2% aqueous hydrochloric acid (4 L), aqueous sodium hydrogen carbonate (4 L), and finally water (4 L). The organic layer was dried over anhydrous sodium sulfate, filtered and the filtrate evaporated to give a syrup. This syrup was dissolved in methanol (2 L), activated charcoal (200 g) was added and the resulting mixture was heated with stirring to 55° C. for 2 hours. After cooling the mixture was filtered and the filtrate was concentrated to give a residue. This residue was dissolved in dichloromethane (1 L) and added dropwise to a mixture of hexane:ether (1:1, 12 L) to give 0.46 kg of the title compound as a white solid. $^1$H NMR (CD$_3$OD): δ 1.15 (t, 3H, J=7.0 Hz, —OCH$_2$CH$_3$); 1.50 (t, 1H, J=12.3 Hz, H-3a of NANA); 1.80, 1.91, 1.96, 2.01, 2.02, 2.04, 2.05, 2.07, 2.08, 2.09, 2.10, 2.16, 2.26 (13-Ac); 2.55 (dd, 1H, J=4.6, 12.3 Hz, H-3e of NANA); 3.84 (S, 3H, COOCH$_3$).

Preparation of Ethyl(methyl(5-acetamido-3,5-dideoxy-4,7,8,9-tetra-O-acetyl-α-D-glycero-D-galacto-2-nonulopyanosylonate))-(2,3)-O-(2,4,6-tri-O-acetyl-β-D-galactopyranosyl)-(1-4)-O-((2,3,4-tri-O-benzyl-α-L-fucopyranosyl)-(1-3)-O-(2-acetamido-6-O-acetyl-2-deoxy-β-D-glucopyranosyl)-(1-3)-O-2,4,6-tri-O-caetyl-β-D-galactopyranoside
(X)

To a solution of the alcohol (IX) (0.118 kg, 0.090 mol) in a mixture of dichloromethane (250 mL) and dimethylformamide (60 mL) was added tetraethylammonium bromide (18.8 g, 0.090 mol). The mixture was then stirred with molecular sieves (4A, 0.250 kg) under nitrogen at room temperature for 6 hours. To the above mixture was added freshly prepared tri-O-benzyl-α-L-fucopyranosyl bromide (0.180 kg, 0.360 mol) in dichloromethane (100 mL). The reaction mixture was then stirred under nitrogen at room temperature for 36 hours until TLC (10:10:3, ethyl acetate:hexane:ethanol) showed completion of the reaction. The reaction mixture was treated with a mixture of methanol (30 mL) and diisopropylethylamine (30 mL) and was stirred at room temperature for 30 minutes. The mixture was diluted with 1 L of dichloromethane and filtered through a bed of celite. The filtrate was washed with aqueous saturated sodium bicarbonate (1.5 L) and water (2 L), and the organic layer dried over magnesium sulfate, filtered, and concentrated to a syrup. This syrup was chromatographed on silica gel (3.5 kg silica gel, 230–400 mesh, ethyl acetate:hexane:ethanol, 5:5:1) to give the title compound (0.110 kg, 73%) as an amorphous solid. $^1$H NMR (CDCl$_3$): δ 1.17 (t, 3H, J=7.2 Hz, —OCH$_2$CH$_3$), 1.18 (d, 3H, J=7.0 Hz, CH$_3$ of Fuc), 1.60, 1.78, 1.84, 1.99, 2.01, 2.02, 2.04, 2.04, 2.06, 2.06, 2.07, 2.15, 2.19 (13-Ac), 2.55 (dd, 1H, J=4.4, 12.2 Hz, H-3e of NANA), 3.82 (s, 3H, COOCH$_3$), 7.4–7.6, (15H, aromatic).

Preparation of Ethyl(sodium(5-acetamido-3,5-dideoxy-α-D-glycero-D-galacto-2-nonulopyanosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside (Z)

To a solution of compound X (105 g, 61 mmol) in acetic acid (900 mL) was added palladium hydroxide on charcoal (20 g, 20% Pd). The reaction mixture was purged two times with hydrogen and then stirred under a hydrogen atmosphere for 8 hours until TLC (90:10, dichloromethane:methanol) showed completion of the reaction. The reaction vessel was purged several times with nitrogen and the reaction mixture was filtered through a bed of celite to remove the catalyst. The celite pad was washed with ethyl acetate several times. Concentration of the filtrate gave the debenzylated product as a white glass (about 97 g). The white glass was dried over high vacuum overnight and was dissolved in ethyl acetate (500 mL). The product triol (79 g, 89%) was precipitated out as white solid with addition of 1 L of a mixture of ether and hexane (8:2). A proton spectrum of the product showed the complete absence of aromatic protons.

To a solution of the triol (79 g, 50 mmol) in methanol (1 L) was added a solution of sodium methoxide (70 mL, 25% w/v). The reaction mixture was stirred at room temperature for 17 hours. Water (100 mL) was added and the mixture was stirred at room temperature for an additional 24 hours until TLC on silica gel (7:2:1, isopropanol:$NH_4OH$:$H_2O$) showed completion of the reaction. To the reaction mixture was added 150 mL of AG-50 H+ ion-exchange resin, which had been thoroughly washed with methanol, and the resulting mixture was stirred at room temperature for 30 minutes. The ion-exchange resin was removed by filtration and filtrate was concentrated to dryness to provide a white glass. The material was dissolved in methanol (300 mL) and filtered through a 0.22μ nylon membrane. The filtrate was diluted with ethyl ether (300 mL) to give the free pentasaccharide (48 g, 84%) as a white solid. $^1$H NMR ($D_2O$): δ 1.10 (d, 3H, J=6.5 Hz, $CH_3$ of Fuc); 1.16 (t, 3H, J=7.0 Hz, —$OCH_2CH_3$); 1.74 (t, 1H, J=12.2 Hz, H-3a of NANA); 1.95, 1.96 (2-Ac); 2.72 (dd, 1H, J=4.4, 12.2 Hz, H-3e of NANA); 4.32 (d, 1H, J=8.0 Hz, β-anomeric); 4.46 (d, 1H, J=7.4 Hz, β-anomeric); 4.65 (d, 1H, J=7.9 Hz, β-anomeric); 5.06 (d, 1H, J=4.1 Hz, α-anomeric of fucose).

Compounds XII–XXVI (FIG. 12B) can be synthesized using the general methodology described above, using techniques well known to one of skill in the art. FIG. 12B also provides comparisons of the blocking abilities of the compounds relative to Z. The assay described in Example 16 was used to measure blocking of E-selectin mediated binding. The concentration of oligosaccharide required to achieve 50% inhibition ($IC_{50}$) of control adhesion was used to compare analogs for potency.

In FIG. 12B, the synthesis of compounds XII–XX and XXII–XXVI utilized an enzymatic fucosidation step (Mollicone, R; Gibaud, A.; Francois, A.; Ratcliffe, M.; Oriol, R. *Eur. J. Biochem.* 191, 169–176 (1990)) to replace the steps reported previously for transforming VII to Z.

Compounds XII and XIII were synthesized beginning with the ethyl glycoside of the appropriately substituted pyranosides. Condensation of each of the ethyl pyranosides with 4-O-(2,3,4,6-tetra-O-acetyl-β-D-galactopyranosyl)-3-6-di-O-acetyl-2-deoxy-2-phthalimido-β-D-glucopyranosyl chloride provides the corresponding trisaccharides which were independently carried through the synthesis to the tetrasaccharide as described for compound VII, above. Enzymatic fucosidation of the tetrasaccharides then provided the pentasaccharides XII and XIII.

XII: Ethyl(ammonium(5-acetamido-3,5-dideoxy-α-D-glycero-D-galacto-2-nonulopyranosylonate))-(2-3)-O-(β-D-galactopyranosyl)-(1-4)-((α-L-fucopyranosyl)-(1-3))-O-(2-acetamido-2-deoxy-β-D-glucopyranosyl)-(1-3)-O-β-L-arabinopyranoside $^1$H NMR ($D_2O$, 300 MHz) δ 5.14 (d, J=3.8, Hz, 1H, H-1 Fuc), 4.55 (m, 2H, H-1 Glc, Gal), 4.34 (d, J=8.0 Hz, 1H, H-1 Arab), 4.17 (d, J=2.2 Hz, 1H, H-4 Gal), 4.06 (dd, J=3.0, 9.8 Hz, 1H, H-3 Gal), 4.03–3.52 (m, 25 H), 2.78 (dd, J=12.4, 4.5 Hz, 1H, H-3(eq) NeuAc), 2.06 (S, 3H, NHAC), 2.04 (s, 3H, NHAc), 1.80 (dd, J=12.4, 12.4 Hz, 1H, H-3(ax) NeuAc), 1.28 (t, 3H, $CH_2CH_3$), 1.19 (d, J=6.4 Hz, 3H, H-6 Fuc).

XIII: 3(S)-O-(1(R)-O-ethyl-pyranosyl)(ammonium (5-acetamido-3,5-dideozy-α-D-glycero-D-galacto-2-nonulopyranosylonate))-(2-3)-O-(β-D-galactopyranosyl)-(1-4)-O-((α-L-fucopyranosyl)-(1-3))-O-2-acetamido-2-deoxy-β-D-glucopyranoside $^1$H NMR ($D_2O$, 300 MHz) δ 5.13 (d, J=3.8, Hz, 1H, H-1 Fuc), 4.55 (m, 3H, H-1 Gal, Glc, Pyr), 4.11 (dd, J=2.9, 9.8 Hz, 1H, H-3 Gal), 4.05–3.42 (m, 26 H), 2.80 (dd, J=12.4, 4.5 Hz, 1H, H-3(eq) NeuAc), 2.25 (bm, 1H, Pyr), 2.06 (s, 6H, NHAC), 2.15–1.97 (bm, 2H, Pyr), 1.82 (dd, J=12.4, 12.4 Hz, 1H, H-3(ax) NeuAc), 1.55 (bm, 1H, Pyr), 1.21 (m, 6H, $CH_2CH_3$ and H-6 Fuc).

The preparation of compounds XIV–XVI began by condensing the monoprotected cyclohexanediols with 3,4,6-tri-O-acetyl-2-deoxy-2-phthalimido-α-D-glucopyranosyl bromide as described for compound VI. The corresponding trisaccharides were converted to the tetrasaccharides using procedures similar to that described for compound VI, above. Enzymatic fucosidation of the tetrasaccharides then provided the corresponding pentasaccharides.

XIV: 1(R)-O-(2(R)-Cyclohexanediol(ammonium(5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-2-acetamido-2-deoxy-β-D-glucopyranoside $^1$H NMR ($D_2O$, 300 MHz) δ 5.10 (d, J=3.95, Hz, 1H, H-1 Fuc), 4.70 (d, J=7.4 Hz, 1H, H-1 Glc), 4.50 (d, J=7.8 Hz, 1H, H-1 Gal), 4.07 (dd, J=2.8, 9.8 Hz, 1H, H-3 Gal), 4.00–3.48 (m, 23 H), 2.75 (dd, J=12.4, 4.4 Hz, 1H, H-3(eq) NeuAc), 2.02 (s, 6H, NHAc), 1.78 (dd, J=12.4, 12.4 Hz, 1H, H-3(ax) NeuAc), 1.78–1.50 (bm, 5H, cyclhex), 1.30 (bs, 3H, cychex), 1.15 (d, J=6.5 Hz, 3H, H-6 Fuc).

XV: 1(R)-O-(2(S)-Cyclohexanediol)(ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-2-acetamido-2-deoxy-β-D-glucopyranoside $^1$H NMR ($D_2O$, 300 MHz) δ 5.10 (d, J=3.95, Hz, 1H, H-1 Fuc), 4.59 (d, J=7.7 Hz, 1H, H-1 Glc), 4.50 (d, J=7.8 Hz, 1H, H-1 Gal), 4.08 (dd, J=2.9, 9.8 Hz, 1H, H-3 Gal), 3.98–3.42 (m, 23H), 2.76 (dd, J=12.4, 4.4 Hz, 1H, H-3(eq) NeuAc), 2.03 (s, 3H, NHAc), 2.02 (s, 3H, NHAc), 1.91 (bm, 2H, cychex), 1.79 (dd, J=12.4, 12.4 Hz, 1H, H-3(ax) NeuAc), 1.65 (bm, 2H, cychex), 1.26–1.11 (m, 4H, cychex), 1.16 (d, J=6.5 Hz, 3H, H-6 Fuc).

XVI: 1(S)-p-(2(R)-Cyclohexanediol (ammonium (5-acetamido-3,5-dideoxy-α-D-glycero-D-galacto-2-nonulopyranosylonate))-(2-3)-(β-D-galactopyranosyl)-(1-4)-((α-L-fucopyranosyl)-(1-3))-O-2-acetamido-2-deoxy-β-D-glucopyranoside $^1$H NMR ($D_2O$, 300 MHz) δ 5.10 (d, J=3.95, Hz, 1H, H-1 Fuc), 4.57 (d, J=8.0 Hz, 1H, H-1 Glc), 4.50 (d, J=7.7 Hz, 1H, H-1 Gal), 4.07 (dd, J 2.8, 9.8 Hz, 1H, H-3 Gal), 4.00–3.48 (m, 23H), 2.75 (dd, J=12.4, 4.4 Hz, 1H, H-3(eq) NeuAc), 2.01 (s, 6H, NHAc), 1.78 (dd, J=12.4, 12.4 Hz, 1H, H-3(ax) NeuAc), 1.82–1.74 (bm, 1H, cyclhex), 1.57 (bs, 3H, cychex), 1.44–1.25 (bm, 4H, cyclhex), 1.15 (d, J=6.5 Hz, 3H, H-6 Fuc).

The synthesis of compound XVII began by condensing an appropriately substituted galactoside with 4-O-(2,3,4,6-tetra-O-acetyl-β-D-galactopyranosyl)-3,6-di-O-acetyl-2-deoxy-2-azido-α-D-glucopyranosyl imidate (Bommer, R.; Kinzy, W.; Schmidt, R. R. *Liebigs Ann. Chem.* 425–433 (1991)) to produce a trisaccharide using techniques well known to one of skill in the art. The trisaccharide was converted to the tetrasaccharide using enzymatic sialylation as described for compound VI. Enzymatic fucosidation of the tetrasaccharide then provided the pentasaccharide XVII.

XVII: 5-Methoxycarbonylpentyl (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside $^1$H NMR (D$_2$O, 300 MHz) δ 5.11 (d, J=3.8, Hz, 1H, H-1 Fuc), 4.72 (d, 1H, H-1 Glc), 4.51 (d, J=8.1 Hz, 1H, H-1 Gal), 4.37 (d, J=7.8 Hz, 1H, H-1 Gal), 4.12 (d, J=2.6 Hz, 1H, H-4 Gal), 4.08 (dd, J=3.3, 9.8 Hz, 1H, H-3 Gal), 4.00–3.47 (m, 28H), 3.69 (s, 3H, OMe), 2.77 (dd, J=12.4, 4.5 Hz, 1H, H-3(eq) NeuAc), 2.03 (s, 3H, NHAC), 2.02 (s, 3H, NHAc), 1.80 (dd, J=12.4, 12.4 Hz, 1H, H-3(ax) NeuAc), 1.62 (m, 4H, alkyl), 1.41 (m, 2H, alkyl), 1.17 (d, J=6.4 Hz, 3H, H-6 Fuc).

The synthesis of compound XX began by reacting the benzyl galactoside, prepared in a similar fashion to compound III in which the ethyl group is replaced by benzyl, with 3,4,6-tri-O-acetyl-2-deoxy-2-phthalimido-α-D-glucopyranosyl bromide, as described for compound IV, above. Conversion of this disaccharide to the tetrasaccharide was similar to that reported for compound VII and the pentasaccharide XX was prepared by enzymatic fucosidation.

XX: Benzyl (ammonium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-β-D-gluconyranosyl)-(1-3)-O-β-D-galactopyranoside $^1$H NMR (D$_2$O, 300 MHz) δ 7.43 (m, 5H, phenyl), 5.10 (d, J=3.8, Hz, 1H, H-1 Fuc), 4.67 (d, J=8.2 Hz, 1H, H-1 Glc), 4.50 (d, J=7.8 Hz, 1H, H-1 Gal), 4.42 (d, J=7.6 Hz, 1H, H-1 Gal), 4.12 (d, J=2.6 Hz, 1H, H-4 Gal), 4.06 (dd, J=3.5, 9.8 Hz, 1H, H-3 Gal), 4.00–3.47 (m, 26H), 2.74 (dd, J=12.4, 4.5 Hz, 1H, H-3(eq) NeuAc), 2.01 (S, 3H, NHAc), 1.98 (s, 3H, NHAc), 1.78 (dd, J=12.4, 12.4 Hz, 1H, H-3(ax) NeuAc), 1.14 (d, J=6.4 Hz, 3H, H-6 Fuc).

The preparation of compound XVIII utilized the disaccharide intermediate reported above for compound XX. The benzyl group of the disaccharide was removed by hydrogenation, a technique well-known to one of skill in the art, and the intermediate product was converted to the pentasaccharide as described for compound XX, above.

XVIII: (sodium (5-Acetamido-3,5-dideoxy-α-D-glycero-D-galacto-2-nonulonyranosylonate))-(2-3)-(β-D-Salactopyranosyl)-(1-4)-((oe-L-fucopyranosyl)-(1-3))-O-(2-acetamido-2-deoxy-β-D-glucopyranosyl)-(1-3)-O-D-galactopyranoside.

$^1$H NMR (D$_2$O, 300 MHz) δ 5.20 (d, J=3.3 Hz, H-1 Gal), 5.10 (d, J=3.7, Hz, H-1 Fuc), 4.54 (d, J=7.7 Hz, H-1), 4.51 (d, J=7.7 Hz, H-1), 4.19 (bd, H-4 Gal), 4.14 (d, J=2.9 Hz, H-4 Gal), 4.06 (dd, J=2.4, 9.8 Hz, H-3 Gal), 4.00–3.47 (m), 2.76 (dd, J=12.4, 4.5 Hz, H-3(eq) NeuAc), 2.01 (s, 6H, NHAc), 1.78 (dd, J=12.4, 12.4 Hz, H-3(ax) NeuAc), 1.15 (d, J=6.4 Hz, H-6 Fuc).

The synthesis of compound XIX condensed the 1,5-anhydro-galactoside prepared by a tin hydride reduction of 2,3,4,6-tetra-O-acetyl-α-D-galactopyranosyl bromide (Witczak, Z. J.; Whistler, R. L. *Carb. Res.* 150, 121–131 (1986)) with 1,3,4,6-tetra-O-acetyl-2-deoxy-2-acetamido-β-D-glucopyranoside (Aldrich) (Kiso, M.; Anderson, L. *Carb. Res.* 136, 309–323 (1985)) to provide the disaccharide. The disaccharide was converted to the tetrasaccharide in a similar manner to that described for compound VII. Enzymatic fucosidation afforded XIX.

XIX: (Ammonium (5-acetamido-3,5-dideoxy-α-D-glycero-D-galacto-2-nonuloryranosylonate))-(2-3)-O-(β-D-galactonyranosyl)-(1-4)-O-((α-L-fucopyranosyl)-(1-3))-O-(2-acetamido-2-deoxy-β-D-glucopyranosyl)-(1-3)-O-β-D-1,5-anhydrocalactopyranoside $^1$H NMR (D$_2$O, 300 MHz) δ 5.10 (d, J=3.95, Hz, 1H, H-1 Fuc), 4.73 (d, J=8.0 Hz, 1H, H-1 Glc), 4.52 (d, J=7.8 Hz, 1H, H-1 Gal), 4.15 (d, J=3.1 Hz, 1H, H-4 Gal), 4.08 (dd, J=3.0, 9.8 Hz, 1H, H-3 Gal), 4.00–3.49 (m, 27H), 3.19 (dd, J=11.2, 11.2 Hz, 1H, H-1 Gal), 2.76 (dd, J=12.4, 4.4 Hz, 1H, H-3(eq) NeuAc), 2.02 (s, 3H, NHAc), 2.01 (s, 3H, NHAc), 1.78 (dd, J=12.4, 12.4 Hz, 1H, H-3(ax) NeuAc), 1.15 (d, J=6.5 Hz, 3H, H-6 Fuc).

The synthesis of compound XXI began by removing the allyloxy carbonyl group of compound VIII as described for compound IX. Heating the amine in acetic acid in methanol at 50° C. then prepared the deacylated compound ethyl (methyl (5-acetamido-3,5-dideoxy-4,7,8,9-tetra-O-acetyl-α-D-glycero-D-galacto-2-nonulopyranosylonate))-(2-3)-O-(3, 4,6-tri-O-acetyl-β-D-galactopyranosyl)-(1-4)-O-(2-amino-6-O-acetyl-β-D-glucopyranosyl)-(1,3)-O-(2,4,6-tri-O-acetyl)-β-D-galactopyranoside. Acylation with allyloxy carbonyl chloride as described for compound V followed by chemical fucosidation, hydrogenation and deacetylation as described for compounds X and XI then provided compound XXI.

XXI: Ethyl(ammonium (5-acetamido-3,5-dideoxy-α-D-glycero-D-galacto-2-nonulopyranosylonate))-(2-3)-O-(β-D-galactopyranosyl)-( 1-4)-O-((α-L-fucopyranosyl)-(1-3))-O-(2-pronylcarbamoyl-2-deoxy-β-D-glucopyranosyl)-(1-3)-O-β-D-galactopyranoside $^1$H NMR (D$_2$O, 300 MHz) δ5.15 (d, J=3.9 Hz, 1H, H-1 Fuc), 4.70 (d, J=8.5 Hz, 1H, H-1 Glc), 4.48 (d, J=7.8 Hz, 1H, H-1 Gal), 4.35 (d, J=7.8 Hz, 1H, H-1 Gal), 4.11 (d, J=3.0 Hz, 1H, H-4 Gal), 4.09–3.46 (m, 30H), 2.73 (dd, J=12.4, 4.5 Hz, 1H, H-3(eq) NeuAc), 2.00 (s, 3H, NHAC), 1.78 (dd, J=12.4, 12.4 Hz, 1H, H-3(ax) NeuAc), 1.19 (m, 2H, propyl), 1.21–1.12 (m, 6H, CH$_2$CH$_3$ and H-6 Fuc), 0.87 (t, 3H, CH$_3$ alkyl).

The synthesis of compound XXII utilized enzymatic sialylation as described for compound VII, and fucosidation of the 2-deoxy-1,5-anhydro-lactone.

XXII: (Ammonium (5-acetamido-3,5-dideoxy-α-D-glycero-D-galacto-2-nonulopyranosylonate))-(2-3)-O-(β-D-galactopyranosyl)-(1-4)-O-((α-L-fucoryranosyl)-(1-3))-O-2-deoxy-1,5-anhydro-D-glucopyranoside $^1$H NMR (D$_2$O, 300 MHz) δ 5.04 (d, J=3.8, Hz, 1H, H-1 Fuc), 4.53 (d, J=7.6 Hz, 1H, H-1 Gal), 4.11 (dd, J=3.1, 9.8

Hz, 1H, H-3 Gal), 4.06–3.44 (m, 22H), 2.78 (dd, J=12.4, 4.5 Hz, 1H, H-3(eq) NeuAc), 2.20 (bm, 1H, H-2 Glc), 2.02 (s, 3H, NHAc), 1.83 (dd, J=12.2, 12.2 Hz, 1H, H-3(ax) NeuAc), 1.62 (bm, 1H, H-2 Glc), 1.21 (d, J=6.4 Hz, 3H, H-6 Fuc).

Compounds XXIII and XXIV were prepared by condensing either alkyl 2,4,6-tri-O-benzyl-β-D-galactoside, where alkyl is octyl or decyl, with 4-O-(2,3,4,6-tetra-O-acetyl-β-D-galactopyranosyl)-3,6-di-O-acetyl-2-deoxy-2-phthalimido-β-D-glucopyranosyl chloride to produce the trisaccharides in a similar manner as that described for compound VI, above. Enzymatic sialylation, as described for compound VII, and fucosidation then afforded the pentasaccharides XXIII and XXIV, respectively.

XXIII: Octyl (sodium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-8-D-glucopyranosyl)-(1-3)-O-β-D-galactopyranoside $^1$H NMR (D$_2$O/DOOCCD$_3$, 300 MHz) δ 5.14 (bd, 1H, H-1 Fuc), 4.52 (d, J=7.8 Hz, 1H, H-1 Gal), 4.36 (d, J=7.7 Hz, 1H, H-1 Gal), 4.14 (bd, 1H, H-4 Gal), 4.08 (bdd, 1H, H-3 Gal), 4.11–3.49 (m, 29H), 2.77 (bdd, 1H, H-3(eq) NeuAc), 2.02 (6H, NHAc, under acetic acid peak), 1.81 (dd, J=12.4, 12.4 Hz, 1H, H-3(ax) NeuAc)10 .60 (bm, 2H, alkyl), 1.27 (bm, 10H, alkyl), 1.16 (bd, J=4.4 Hz, 3H, H-6 Fuc), 0.84 (bt, 3H, CH$_3$ alkyl).

XXIV: Decyl (sodium (5-acetamido-3,5-dideoxy-α-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside $^1$H NMR (D$_2$O, 300 MHz) δ5.11 (bd, 1H, H-1 Fuc), 4.71 (bm, 2H, under water peak), 4.52 (d, J=7.7 Hz, 1H, H-1 Gal), 4.36 (d, J=7.9 Hz, 1H, H-1 Gal), 4.16 (bd, 1H, H-4 Gal), 4.11–3.49 (m, 29H), 2.75 (dd, J=12.4, 4.5 Hz, 1H, H-3(eq) NeuAc), 2.02 (bs, 6H, NHAc), 1.78 (dd, J=12.4, 12.4 Hz, 1H, H-3(ax) NeuAc), 1.60 (bm, 14H, alkyl), 1.17 (bd, 3H, H-6 Fuc), 0.84 (bt, 3H, CH$_3$ alkyl).

The synthesis of compounds XXV and XXVI reacted alkyl 2,4-di-O-acetyl-β-D-galactopyranoside, where alkyl is either dodecyl or octadecyl, with 4-O-(2,3,4,6-tetra-O-acetyl-β-D-galactopyranosyl)-3,6-di-O-acetyl-2-deoxy-2-phthalimido-β-D-glucopyranosyl chloride to produce the trisaccharide using conditions similar to those used for compound VI. Enzymatic sialylation, as described for compound VII, and fucosidation then provided the pentasaccharides XXV and XXVI, respectively.

XXV: Dodecyl (sodium (5-acetamido-3,5-dideoxy-α-D-glycero-D-galacto-2-nonulopyranosylonate))-(2-3)-O-(β-D-galactoryranosyl)-(1-4)-O-((α-L-fucoryranosyl)-(1-3))-O-(2-acetamido-2-deoxy-β-D-glucopyranosyl)-(1-3)-O-β-D-galactopyranoside $^1$H-NMR (300 MHz, δ in ppm relative to CD$_2$HOD) 5.02 (d, J=4 Hz, 1H), 4.65 (d, J=8 Hz, 1H), 4.50 (d, J=8 Hz, 1H), 4.20 (d, J=8 Hz, 1H), 4.05–3.30 (m), 2.85 (dd, J=4 Hz, J=12.4 Hz, 1H), 2.02 (s, 3H), 1.97 (s, 3H), 1.70 (dd, J=12.4 Hz, J=12.4 Hz, 1H), 1.60 (m,. 2H), 1.35 (m, 20H), 1.20 (d, J=7 Hz, 3H), 0.92 (t, J=6 Hz, 3H).

XXVI: Octadecyl (sodium (5-acetamido-3,5-dideoxy-β-D-glycero-D-galacto-2-nonulopyranosylonate))-(2-3)-O-(β-D-galactopyranosyl)-(1-4)-O-((α-L-fucopyranosyl)-(1-3))-O-(2-acetamido-2-deoxy-β-D-glucopyranosyl)-(1-3)-O-β-D-galactopyranoside $^1$H-NMR (300 MHz, δ in ppm relative to CD$_2$HOD) 5.02 (d, J=4 Hz, 1H), 4.65 (d, J=8 Hz, 1H), 4.50 (d, J=8 Hz, 1H), 4.20 (d, J=8 Hz, 1H), 4.05–3.30 (m), 2.85 (dd, J=4 Hz, J=12.4 Hz, 1H), 2.02 (s, 3H), 1.97 (s, 3H), 1.70 (dd, J=12.4 Hz, J=12.4 Hz, 1H), 1.60 (m,. 2H), 1.35 (m, 36H), 1.20 (d, J=7 Hz, 3H), 0.92 (t, J=6 Hz, 3H).

EXAMPLE 16

Inhibition of binding by Z

This example shows the ability of Z prepared as described above, to inhibit HL-60 cell binding to recombinant E-Selectin. In this assay recombinant soluble E-selectin is bound to the plastic surface of a 96 well ELISA plate. Dilutions of test compounds are added to the wells followed by HL-60 cells which bear the ligand for E-selectin. The cells are allowed to adhere to the E-selectin coated assay plate and the nonadherent cells are removed by washing the plate with an automated plate washer. Bound cells are quantitated by measuring the cellular enzyme myeloperoxidase. The concentration of oligosaccharide required to achieve 50% inhibition of control adhesion is used to compare analogs for potency.

Methods

Microflex III 96 well ELISA plates were coated with 50 μL of recombinant E-selectin (4 μg/mL) in Dulbecco's phosphate buffered saline (DPBS) and incubated at room temperature for 3 hours. The plates were then washed three times with 200 μL DPBS containing bovine serum albumin (10 mg/mL: DPBS-BSA) and incubated at room temperature for 60 minutes with DPBS-BSA.

Oligosaccharides to be tested were prepared in 1.5 mL eppendorf tubes by adding enough DPBS to make each sample a 10 mM solution according to its molecular weight. The pH was adjusted to be within 7.0 and 7.4.

After 30 minutes 2×10$^5$ HL-60 cells (10$^7$/mL) were added and incubated for 15 minutes at room temperature. The unbound cells were removed by washing the plate 3 times with HBSS containing HEPES buffer (20 mM), glucose (0.2%), CaCl$_2$ (1 mM) and BSA (10 mg/mL). After removal of the wash buffer the bound cells remaining were lysed by addition of Nonidet P 40 (0.1%) in 25 mM citrate/phosphate buffer. After 5 minutes 50 μL of o-phenylenediamine dihydrochloride (1 mg/mL) in citrate/phosphate buffer containing 0.001% hydrogen peroxide was added to each well. After 5 to 10 minutes the development of color was halted by the addition of 40 μL of H$_2$SO$_4$. Color developed was measured in a plate reading spectrophotometer at 492 nm.

Results

Figure 13:
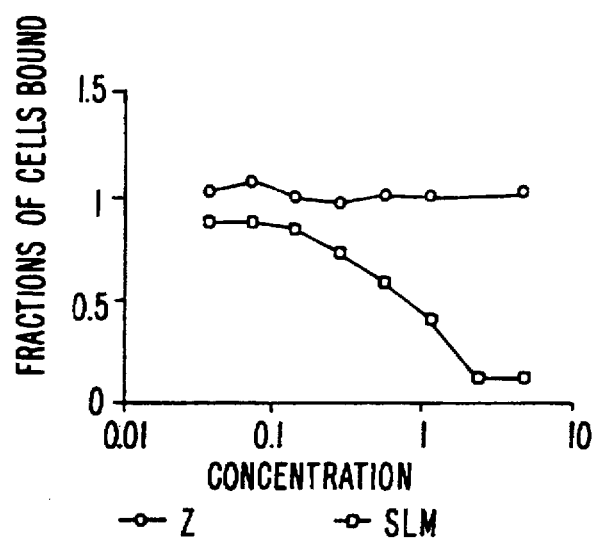
FIG. 13 shows inihibtion of binding of HL-60 cells to recombinant E-selectin in a concentration dependent manner by Z but not by the non-fucosylated derivative SLN.

The binding of HL-60 cells to recombinant E-selectin was inhibited in a concentration dependent manner by Z but not by the non-fucosylated derivative SLN (FIG. 13). For Z, the IC$_{50}$ for inhibition in this assay was calculated as approximately 500 μM.

EXAMPLE 17

Inhibition of Leukocyte Rolling by Z

This example demonstrates the ability of the pentasaccharide Z to inhibit histamine induced leukocyte rolling in the rat.

Methods

Surgical procedure. Sixty-four male Sprague-Dawley rats (200–250 g) were maintained on a purified laboratory diet and fasted for 24 hours prior to the experiment. The animals were initially anesthetized with pentobarbital (65 mg/kg body weight), then a tracheotomy was performed to facilitate breathing during the experiment. The right carotid artery was cannulated and systemic arterial pressure was measured with a Statham (Oxnard, Calif.) P23A pressure transducer connected to the carotid artery cannula. Systemic blood pressure and heart rate were continuously recorded with a Grass physiologic recorder (Grass Instruments, Massachusetts). The left jugular vein was also cannulated for drug administration and blood sample collection. After a midline abdominal incision a segment of the mid-jejunum was exteriorized. All exposed tissue was moistened with saline-soaked gauze to minimize evaporation and dehydration.

Intravital microscopy. Rats were placed in a supine position on an adjustable plexiglass microscope stage and the mesentery was draped over an optically clear coverslip that allowed for observation of a 2 cm$^2$ segment of tissue. The temperature of the pedestal was maintained at 37° C. with a constant temperature circulator (Fisher Scientific, model 80). A small rubber gasket (area=3.14 cm$^2$) was placed on the mesentery and the outside area of contact between the gasket and mesentery was sealed (to prevent leakage of superfusate from the ring) with a mixture of high vacuum grease (Dow Corning Corp., Midland, Mich.) and white petrolatum (E. Fougera & Co., Melville, N.Y.). Rectal and mesenteric temperatures were continuously monitored using an electrothermometer. The exposed bowel wall was covered with Saran Wrap (Dow Chemical Co., Indiana), and the mesenteric tissue within the gasket was suffused with warmed bicarbonate-buffered saline (BBS; pH 7.4) that was bubbled with a mixture of 5% $O_2$; 5% $CO_2$; 90% $N_2$.

An inverted microscope (Nikon Optiphoto, Japan) with a ×40 objective lens (Nikon Optiphoto, Japan) and a ×10 eyepiece was used to observe the mesenteric microcirculation. The mesentery was transilluminated with a 12 V-100 W direct current-stabilized light source. A video camera (Hitachi, VK-C150, Japan) mounted on the microscope projected the image onto a color monitor (Sony, PVM-2030, Japan), and the images were recorded using a video cassette recorder (Panasonic, NV8950, Japan). A video time-date generator (Panasonic, WJ810, Japan) projected the time, date, and stopwatch function onto the monitor.

Single unbranched venules with diameters ranging between 25 μm and 35 μm and a length>150 μm were selected for study. Venular diameter (Dv) was measured either on- or off-line using a video image-shearing monitor (IPM, La Mesa, Calif.). The number of adherent leukocytes was determined off-line during playback of videotaped images. A leukocyte was considered to be adherent to venular endothelium if it remained stationary for a period equal to or greater than 30 seconds. Adherent cells were expressed as the number per 100 μm length of venule. The number of emigrated leukocytes was also determined off-line during playback of videotaped images. Any interstitial leukocytes present in the mesentery at the onset of the experiment were subtracted from the total number of leukocytes that accumulated during the course of the experiment. Leukocyte emigration was expressed as the number per microscopic field (1.7×10$^{-2}$ mm$^2$) or 150 μm length of venule. Rolling leukocytes were defined as those white blood cells that moved at a velocity less than that of erythrocytes in the same stream. The flux of rolling leukocytes was determined as the number of rolling leukocytes which crossed a fixed point on the venule over a given period of time. Leukocyte rolling velocity was determined from the time required for a leukocyte to roll along a given distance of the venule. The number of rolling leukocytes was determined from the flux of rolling leukocytes and leukocyte rolling velocity. Centerline red blood cell-velocity ($V_{RBC}$) was measured using an optical Doppler velocimeter (Microcirculation Research Institute, Texas A&M University) that was calibrated against a rotating glass disk coated with red blood cells. Venular blood flow was calculated from the product of mean red blood cell velocity [$V_{mean}$=centerline velocity ÷1.6] and microvascular cross-sectional area, assuming cylindrical geometry. Venular wall shear rate (γ) was calculated based on Newtonian definition: γ=8(V mean/Dv).

Experimental protocols. After all parameters measured on-line (arterial pressure, erythrocyte velocity, venular diameter) were in a steady state, the mesentery was superfused (2 mL/min) with either histamine (10$^{-7}$M, 10$^{-6}$M, 10$^{-5}$M) or BBS alone, with video recordings for quantitation of leukocyte-endothelial cell adhesion and repeat measurements of hemodynamic parameters made 20–30 minutes into the superfusion period. The responses to BBS alone or each concentration of histamine were determined in 5–6 rats. In some experiments, the responses to 10$^{-5}$M histamine were examined in animals which were treated intravenously with Z or SLN (missing the fucose residue required for recognition by P-selectin). Both were administered at 1 mg/100 g body weight 10 min prior to superfusion with histamine. In experiments using monoclonal antibodies (MAb), rats received an intravenous injection of the antibody (2 mg/kg) 30 minutes prior to superfusion with 10$^{-5}$M histamine. MAbs used included 'blocking' (PB1.3; P-selectin/blocking/IgG1/clone 352) and non-blocking (PNB 1.6; P-selectin/non-blocking/IgG1/clone P6H6) to P-selectin, and a blocking E-selectin antibody (P6E2). Both PB1.3 and P6E2 cross react with rat P and E-selectins, respectively, while PNB1.6 appears not to cross react with rat P-selectin. Therefore, PNB1.6 serves primarily as an isotype matched antibody control in these experiments.

Results

Figure 14A:
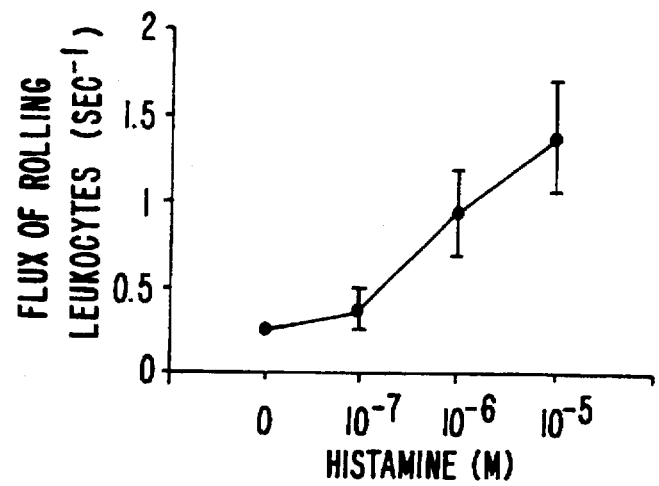
FIG. 14 summarizes the changes in the flux of rolling leukocytes (FIG. 14A), leukocyte rolling velocity (FIG. 14B), and number of rolling leukocytes (FIG. 14C) induced by different concentrations of histamine.
Figure 14B:
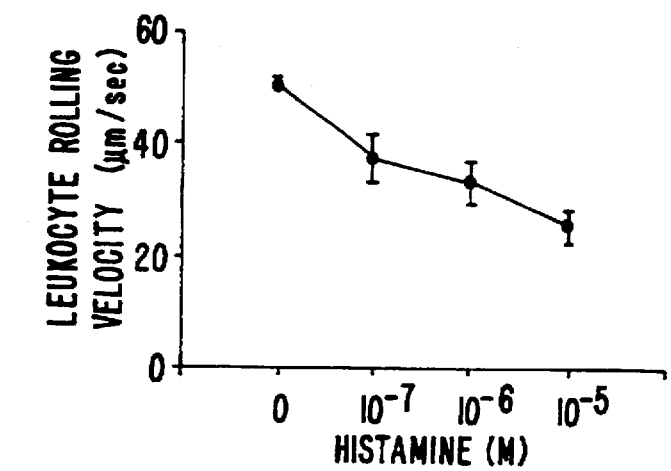
Figure 14C:
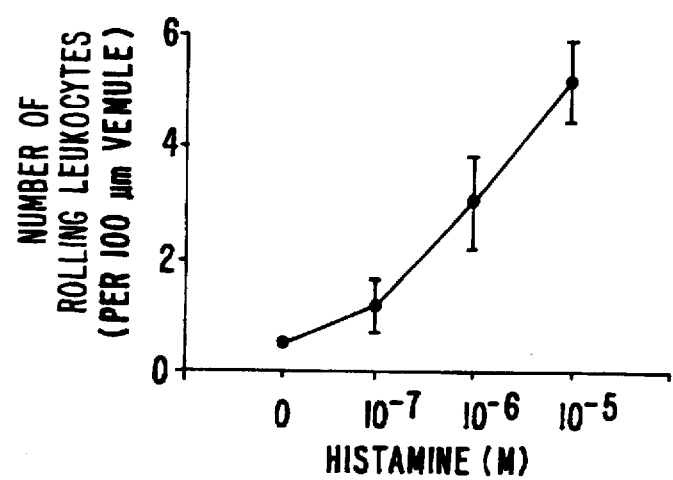

Histamine induced leukocyte rolling in mesenteric venules. The most profound effects of histamine on leukocyte-endothelial cell interactions were related to leukocyte rolling. FIG. 14 summarizes the changes in the flux of rolling leukocytes (Panel A), leukocyte rolling velocity (Panel B), and number of rolling leukocytes (Panel C) induced by different concentrations of histamine. Over the concentration range of 10$^{-7}$–10$^{-5}$M, histamine elicited a dose-related recruitment of rolling leukocytes (5-fold increase at 10$^{-5}$M) and reduced leukocyte rolling velocity (50% at 10$^{-5}$M). The net result of these changes was a dramatic increase in the number of rolling leukocytes in postcapillary venules at any given moment in the presence of histamine (10-fold increase at 10$^{-5}$M).

Figure 15A:
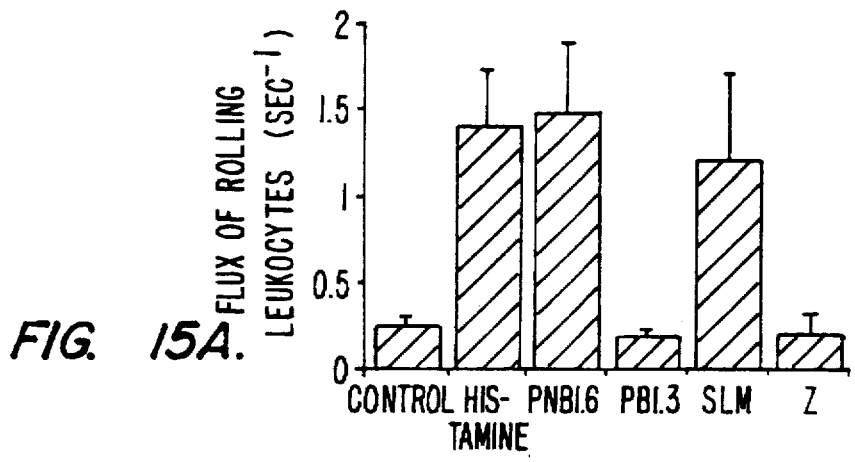
FIGS. 15A–15C shows that a blocking monoclonal antibody to P-selectin (PB1.3) prevented recruitment of rolling leukocytes while a second isotype matched nonblocking P-selectin antibody, which does not cross react with rat P-selectin (PNB1.6), had no effect. Similarly, Z inhibited leukocyte rolling, while SLN had no effect.
Figure 15B:
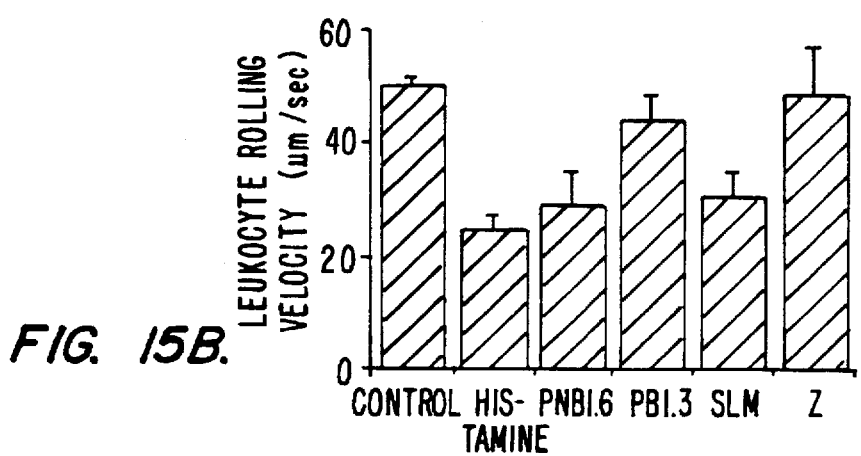
Figure 15C:
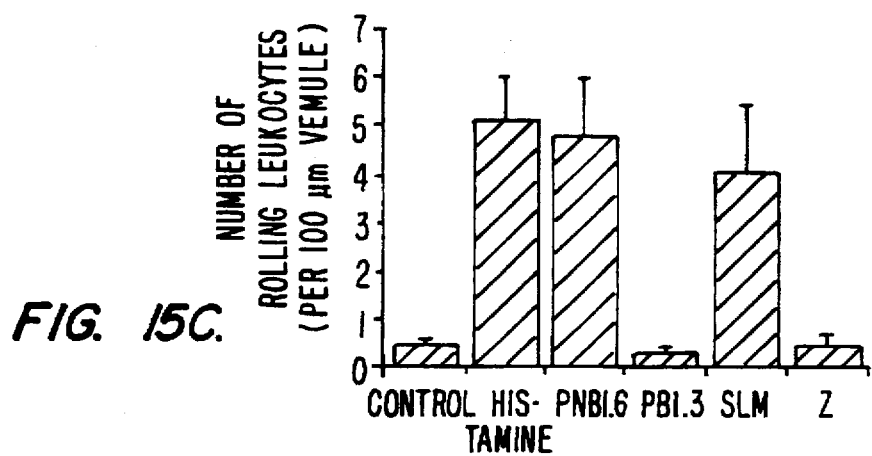

P-selectin has been shown to mediate leukocyte rolling on artificial membranes under shear force, accordingly, several blockers of P-selectin were tested for their ability to inhibit histamine induced leukocyte rolling. As shown in FIG. 15, a 'blocking' monoclonal antibody to P-selectin (PB1.3) prevented recruitment of rolling leukocytes while a second isotype matched 'nonblocking' P-selectin antibody, which does not cross react with rat P-selectin, had no effect. Similarly, Z also inhibited leukocyte rolling, while a closely related inactive analog (SLN) had no effect. A blocking antibody (P6E2) to E-selectin did not block rolling (not shown) providing further evidence for the specific role of P-selectin in histamine induced rolling. Taken together the results suggest that P-selectin plays a major role in histamine induced leukocyte rolling in rat mesenteric venules and that this effect is blocked by Z, a synthetic analog of the P-selectin ligand.

Effects of histamine on leukocyte adherence, trans-endothelial migration and hemodynamic properties. Table 7 summarizes the effects of histamine on the hemodynamic responses of mesenteric venules (erythrocyte velocity, vessel diameter, and wall shear rate) and other changes in leukocyte-endothelial cell interactions including adherence and trans-endothelial migration. In that table, the effects of histamine on venular hemodynamics and leukocyte endothelial cell adhesion in the absence and presence of Z (10 mg/Kg, i.v.), control oligosaccharide (SLN; 10 mg/Kg, i.v.),P-selectin antibody (PB1.3; 2 mg/Kg, i.v.) and isotype matched antibody (PNB1.6; 2 mg/Kg, i.v.) are shown.

With the exception of leukocyte adherence, histamine did not significantly alter any of the aforementioned parameters. Although there appeared to be a dose related reduction in venular shear rate in response to histamine, this did not reach statistical significance. Previous studies on the influence of shear rate on leukocyte rolling indicate that a 40% reduction in shear rate does result in significant recruitment of rolling and adherent leukocytes. Significant increases in the number of adherent leukocytes were noted when the mesentery was superfused with histamine at concentrations of $10^{-6}$M and $10^{-5}$M. The increased leukocyte adherence induced by $10^{-5}$M histamine was significantly attenuated by Z.

Administration of Z, a mimetic of the selectin ligand SLe$^x$ inhibited the rolling of neutrophils along the vascular endothelium.

EXAMPLE 18

Treatment of CVF-induced acute lung injury

This example shows the effect of Z on cobra venom factor (cvf)-induced acute lung injury in the rat.

The intravenous injection of CVF produces intravascular complement activation which results in lung injury, defined as an increase in neutrophil accumulation within the lung, an increase in pulmonary vascular permeability and in lung hemorrhage. It is likely that intravascular complement activation results in the generation of a wide range of inflammatory mediators. Of particular relevance to the studies described here is generation of the split fifth complement component, C5a, which can stimulate the release of histamine from circulating basophils and tissue mast cells. Histamine is one of a number of stimuli which have been demonstrated in vitro to cause the expression of P-selectin on vascular endothelial cells. The expression of selectins, including P-selectin, is a necessary first step in the process of leukocyte adherence to vascular endothelium.

Methods

Animals were dosed with different oligosaccharide preparations or phosphate buffered saline (PBS) five minutes before administration of cobra venom factor (20 units/Kg, i.v.). Included in this material was an aliquot of $^{125}$I-bovine serum albumin (0.5 µCi) and $^{51}$Cr labelled autologous red blood cells (0.5 µCi) for measuring plasma extravasation and hemorrhage respectively. Thirty minutes after adminis-

TABLE 7

| Conditions | Leukocyte adherence (per 100 µm) | Leukocyte emigration (per field) | Erythrocyte velocity (mm/sec) | Venular diameter (µm) | Wall shear rate (sec$^{-1}$) |
| --- | --- | --- | --- | --- | --- |
| Control | 1.0 ± 0.6 | 3.0 ± 1.7 | 2.8 ± 0.6 | 28 ± 2 | 497 ± 81 |
| Histamine | | | | | |
| $10^{-7}$M | 2.8 ± 0.7 | 1.5 ± 0.7 | 2.8 ± 0.2 | 30 ± 1 | 476 ± 38 |
| $10^{-6}$M | 4.8 ± 0.7 | 2.0 ± 0.7 | 2.4 ± 0.2 | 30 ± 1 | 401 ± 91 |
| $10^{-5}$M | 7.2 ± 1.1 | 2.5 ± 0.9 | 1.8 ± 0.4 | 30 ± 1 | 303 ± 64 |
| Histamine ($10^{-5}$M) | | | | | |
| +Z | 2.3 ± 1.9 | 2.0 ± 1.2 | 2.1 ± 0.2 | 29 ± 0.2 | 355 ± 14 |
| +SLN | 5.5 ± 1.4 | 4.8 ± 2.8 | 3.0 ± 0.5 | 31 ± 2 | 495 ± 28 |
| +PB1.3 | 4.5 ± 2.1 | 4.0 ± 1.6 | 2.5 ± 1.0 | 31 ± 1 | 392 ± 146 |
| +PNB1.6 | 9.0 ± 3.0 | 5.0 ± 2.0 | 2.2 ± 0.2 | 29 ± 3 | 488 ± 41 |

CONCLUSIONS

Figure 16A:
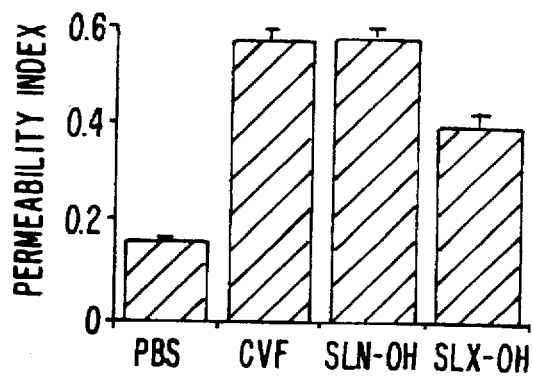
FIG. 16 shows changes in pulmonary vascular permeability (FIG. 16A), hemorrhage (FIG. 16B) and neutrophil accumulation (FIG. 16C) 30 minutes following injection of CVF. Groups of rats were pretreated with either vehicle, SLN-OH (0.6 mg/Kg), or with SLX-OH (0.6 mg/Kg) 5 minutes prior to administration of either CVF or PBS. Each bar represents the mean of 6 animals and vertical lines represent the standard error of the mean.
Figure 16B:
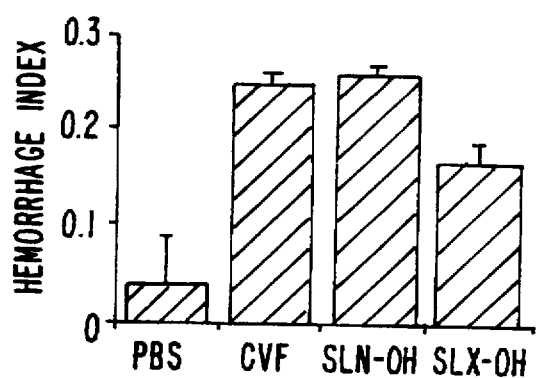
Figure 16C:
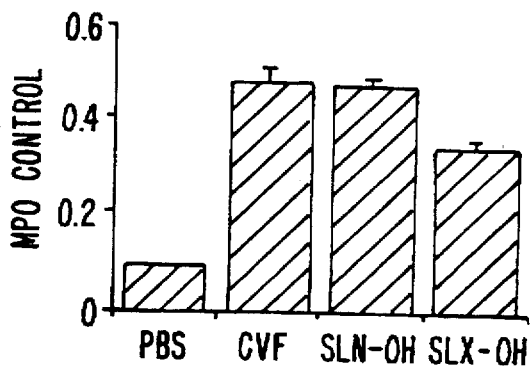

The application of histamine to the superfused microvascular bed of the rat mesentery stimulates a leukocyte endothelial interaction which is primarily characterized by an increase in leukocyte rolling along the endothelium. This interaction is presumed to be mediated via the endothelial expression of P-selectin based on the knowledge that histamine induces P-selectin expression on cultured endothelial cells in vitro and the observation that the interaction was blocked in the presence of an anti-P-selectin antibody.

tration of the cobra venom factor the animals were anesthetized with ketamine hydrochloride (10 mg/Kg) and exsanguinated via the posterior vena cava. The lung vasculature was then perfused through the right cardiac ventricle with 10 mL of PBS. The lungs were removed and the amount of radioactivity remaining within the tissue assessed with a gamma scintillation counter. Increased pulmonary vascular permeability was measured as the ratio of $^{125}$I in lung tissue compared with the amount present in 1 mL of venous blood obtained at the time of death. Lung hemorrhage was measured as the ratio of $^{51}$Cr in lung tissue compared with the amount present in 1 mL of venous blood obtained at the time of death. Neutrophil accumulation in lungs was determined by measuring the myeloperoxidase activity of lungs homogenized in PBS. Myeloperoxidase activity in lung supernatants was assayed by measuring the change in absorbance at 460 nm resulting from decomposition of $H_2O_2$ in the presence of o-dianisidine Results Preliminary experiments compared the activity of the SLe$^x$ analog, NeuAcα2,3Gal,β1 4(Fucα1,3)GlcNAc-OH (SLX-OH) with its nonfucosylated form, sialyl-N-acetyllactosamine (SLN-OH), as inhibitors of lung injury following injection of CVF. The positive controls (injected intravenously with CVF in phosphate buffered saline, PBS) showed (FIG. 16) a six-fold increase in lung permeability (frame A), a five-fold increase in hemorrhage (frame B) and a five-fold increase in lung myeloperoxidase (MPO) content (frame C) compared with negative controls not administered CVF. When 200 μg of SLN-OH (a control carbohydrate which does not support P-selectin mediated adhesion) was injected prior to CVF. the permeability. hemorrhage and MPO values were unaltered at 30 minutes, whereas treatment with SLX-OH reduced the permeability value by 43% ($P<0.001$), hemorrhage by 41% ($P<0.004$) and MPO content by 35% ($P<0.006$).

Figure 17A:
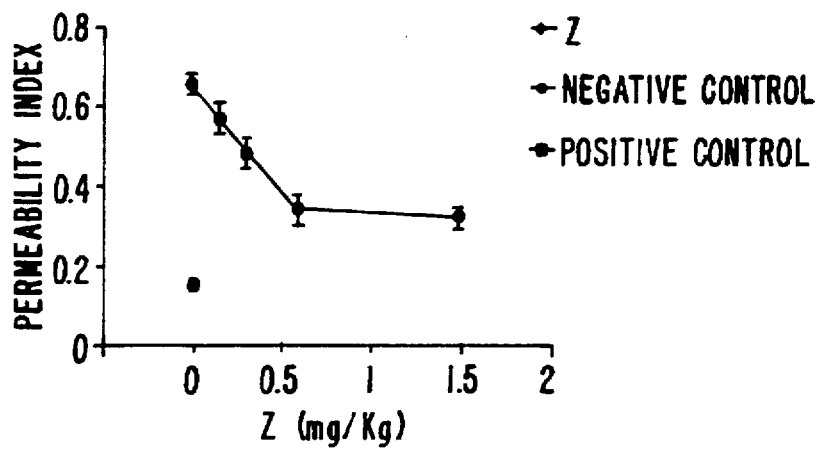
FIG. 17 shows changes in pulmonary vascular permeability (FIG. 17A), hemorrhage (FIG. 17B) and neutrophil accumulation (FIG. 17C) were determined 30 minutes following injection of CVF. Groups of rats were pretreated with either vehicle or Z at the indicated doses 5 minutes prior to administration of CVF or PBS. Each point represents the mean of 6 animals and vertical lines represent the standard error of the mean.
Figure 17B:
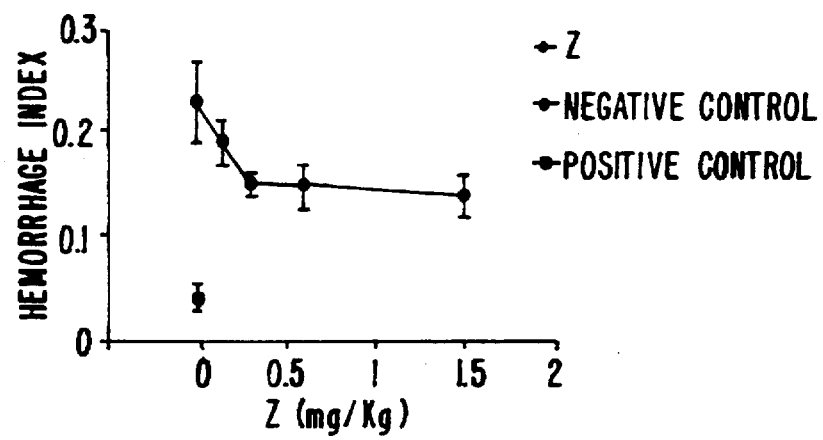
Figure 17C:
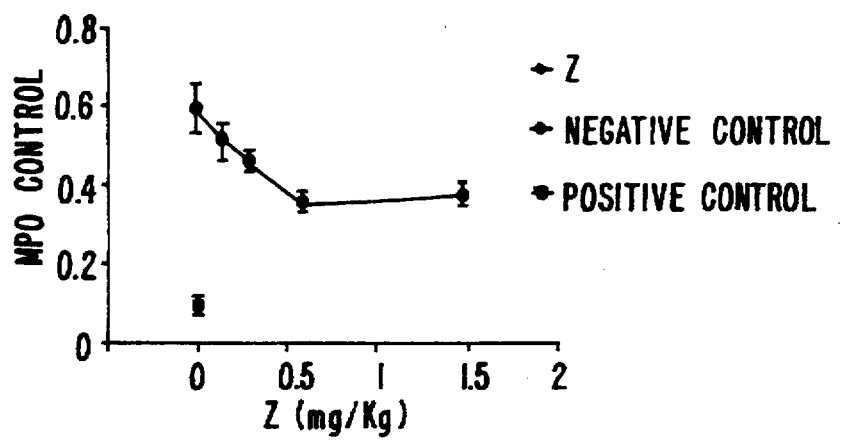

Dose response relationships were subsequently evaluated using Z. Results (FIG. 17) indicate that over a dose range from 0.15 to 1.5 mg/Kg, treatment with Z reduced the permeability values by 67% (frame A), reduced hemorrhage by 47% (frame B), and reduced neutrophil MPO content by 49% (frame C). These data indicate, that Z produces significant protective effects against CVF-induced lung injury, that these protective effects are dose dependent and plateau at 0.6 mg/Kg, and that the protective effects correlate with reduced neutrophil content in the lung, as defined by lung content of MPO.

CONCLUSIONS

The administration of Z not only blocks CVF-induced neutrophil accumulation but also blocks the pathological sequelae (plasma extravasation and hemorrhage) associated with the activation of adherent neutrophils in close juxtaposition with the vascular endothelium. These data not only support a role for neutrophils in mediating tissue damage but also support the concept that a therapeutic benefit may be derived using Z to prevent neutrophil accumulation thus protecting tissue from the potentially harmful consequences of inappropriate neutrophil activation. The specificity of the effect of Z was demonstrated by determining that SLN, a non-fucosylated analog of Z, did not inhibit CVF-induced neutrophil accumulation or CVF-induced lung injury.

EXAMPLE 19

Treatment of IgG-induced acute lung injury

This example demonstrates the effect of Z on IgG- and IgA-induced acute lung injury in the rat.

The formation of immune complexes in tissues occurs under a number of pathological conditions and results in an acute inflammatory response. The inflammatory response consists primarily of plasma extravasation and neutrophil accumulation but may also result in vascular damage leading to extravasation of red blood cells. Models of immune complex-induced pulmonary vascular injury have been developed by Professor Ward and colleagues at the University of Michigan. In these models, when the immune complex comprises IgG isotype immunoglobulin, the inflammatory response and vascular damage is dependent on the participation of neutrophils and can be inhibited by antibodies to the vascular adhesion molecule E-selectin. In contrast, when the immune complex comprises IgA isotype immunoglobulin, neither neutrophils nor E-selectin are involved in the pathogenesis of injury. The apparent selectin dependent (IgG type immune complex) and selectin independent (IgA type immune complex) models were further investigated in the studies described below by examining the extent to which Z, a soluble analog of the selectin ligand, could block lung injury in each of these models.

Methods

Adult male (300 g) specific pathogen-free Long-Evans rats purchased from Charles River Labs (Portage, Mich.) were employed in the studies. For the induction of IgG immune complex pulmonary inflammation rabbit polyclonal IgG rich in antibody to bovine serum albumin (antiBSA) was purchased from Organon Teknika (Westchester, PA). Intraperitoneal ketamine (10 mg/Kg) was administered for anesthesia. 2.5 mg of anti-BSA in a volume of 300 μl was instilled intratracheally via a small intratracheal catheter during inspiration after surgical exposure of the trachea. Intravenous injection of 10 mg BSA was injected intravenously to generate immune complex formation. Trace amounts of $^{125}$I-BSA and $^{51}$Cr-RBC were administered with the BSA as markers for plasma and RBC extravasation respectively. Rats were sacrificed 4 h later and lung injury was assessed by the ratio of radiolabelled albumin in the lungs relative to the circulation (permeability), the ratio of RBC in the lungs relative to the circulation (hemorrhage) and the amount of myeloperoxidase activity in a lung homogenate (neutrophil accumulation). For induction of IgA immune complex induced lung injury 1.2 mg of a murine myeloma IgA protein specific for dinitrophenol (DNP) was instilled intratracheally and 3.3 mg DNP-bovine serum albumin injected intravenously. Lung injury was assessed in the same manner described for IgG-induced lung injury.

SLX-OH, Z, the non-fucosylated control oligosaccharide SLN, or an equivalent volume of PBS were injected intravenously in three equally divided doses at 2, 2.5, and 3 h following deposition of immune complexes. This schedule for injections was selected since it coincides with the time during which rapid expression of E-selectin occurs in the pulmonary vasculature.

Results

Figure 18A:
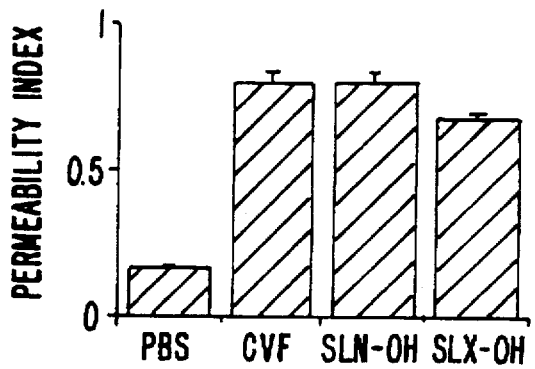
FIG. 18 shows changes in pulmonary vascular permeability (FIG. 18A), hemorrhage (FIG. 18B) and neutrophil accumulation (FIG. 18C) were determined 4 hours following initiation of inflammation by intrapulmonary deposition of IgG immune complexes. Groups of rats were dosed with either vehicle, SLN-OH (100 µg), or with SLX-OH (100 µg) 2.5, 3 and 3.5 hours post induction of inflammation. Each bar represents the mean of 6 animals and vertical lines represent the standard error of the mean.
Figure 18B:
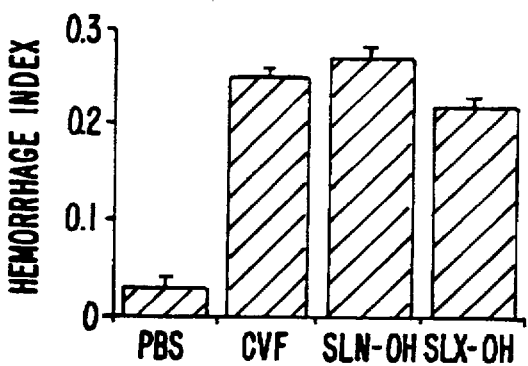
Figure 18C:
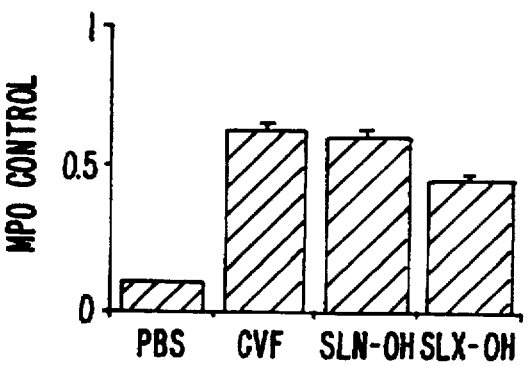

SLX-OH or the non-fucosylated form (SLN) were administered intravenously at 2.5, 3.0 and 3.5 hours following induction of inflammation and the measurements of lung vascular injury made 4 hours following intrapulmonary deposition of immune complexes. All comparisons were made to animals that had been treated intravenously with PBS instead of an oligosaccharide. These reference positive control values (PBS), expressed as mean ±S.E.M., are shown in the bars in FIG. 18 (panels A–C). When compared to results obtained in PBS treated animals SLN administration showed no alteration in vascular permeability value (frame A), no decrease in hemorrhage (frame B), and no decrease in lung content of MPO (frame C). In contrast, treatment with Z caused modest reductions in permeability (20%, P<0.05), hemorrhage (21%, P=N.S.), and in MPO content (27%, P<0.05).

Figure 19A:
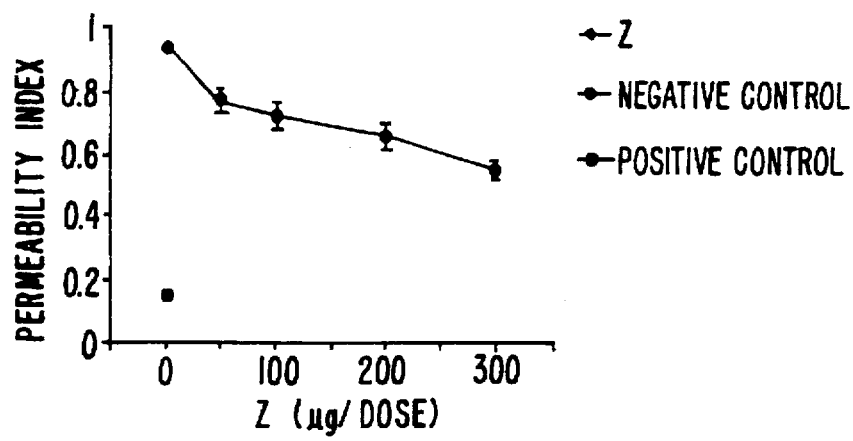
FIG. 19 shows changes in pulmonary vascular permeability (FIG. 19A), hemorrhage (FIG. 19B) and neutrophil accumulation (FIG. 19C) were determined 4 hours following initiation of inflammation by intrapulmonary deposition of IgG immune complexes. Groups of rats were dosed with either vehicle, SLN-OH, or with Z at the indicated doses 2.5, 3 and 3.5 hours post induction of inflammation. Each point represents the mean of 6 animals and vertical lines represent the standard error of the mean.
Figure 19B:
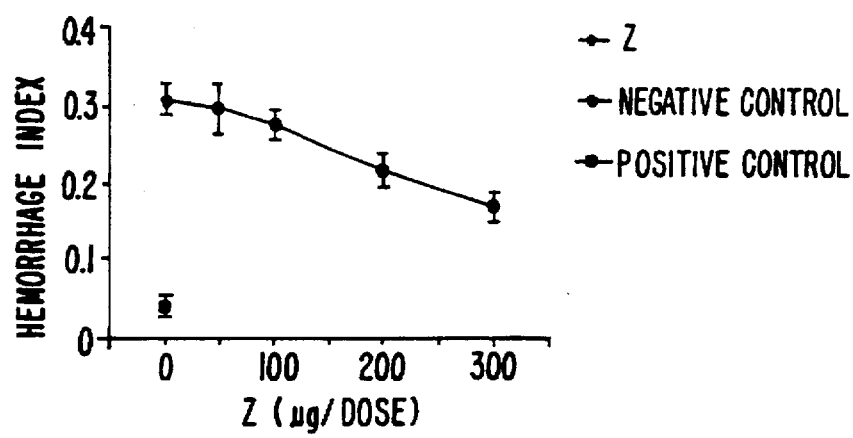
Figure 19C:
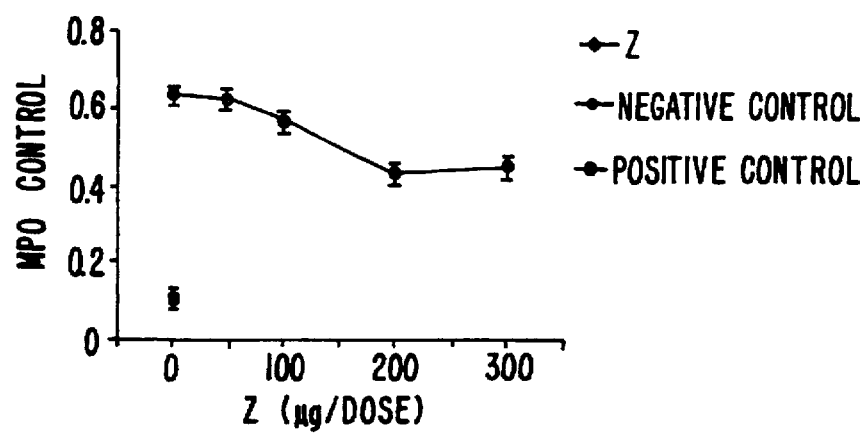

A further series of experiments, shown in FIG. 19 (panels A–C), investigated a range of doses (50–500 μg) of Z with intravenous injections of the indicated amounts at 2.5, 3.0 and 3.5 hours post deposition of immune complexes. At all doses of Z employed there were significant reductions in vascular permeability (FIG. A), the two highest doses of Z produced statistically significant reductions in hemorrhage (panel B) and with respect to the lung MPO content (panel C) treatment with 50 μg did not significantly reduce MPO content, but the 100, 200 and 300 μg doses of Z did produce significant reductions.

Figure 20A:
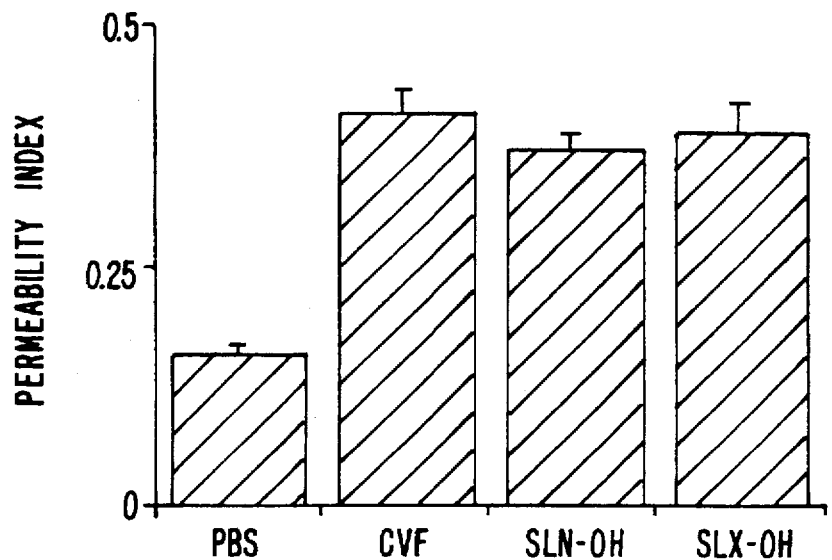
FIG. 20 shows changes in pulmonary vascular permeability (FIG. 20A) and hemorrhage (FIG. 20B) were determined 4 hours following initiation of inflammation by intrapulmonary deposition of IgA immune complexes. Groups of rats were dosed with either vehicle, SLN-OH (100 μpg), or with SLX-OH (100 μg) 2.5, 3 and 3.5 hours post induction of inflammation. Each bar represents the mean of 6 animals and vertical lines represent the standard error of the mean.
Figure 20B:
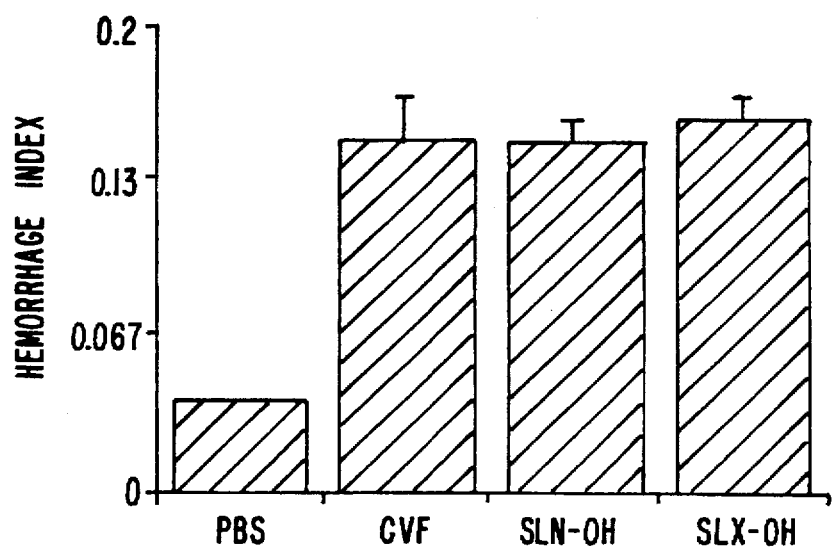

SLX-OH which was protective in IgG immune complex-induced injury was also used in the IgA immune complex model of lung injury (FIG. 20). In this model neutrophil recruitment is not involved in the injury inducing events in lung and E-selectin is not required for development of lung damage. Accordingly it was observed that SLX-OH did not afford any protection from IgA immune complex induced lung injury assessed by changes in vascular permeability and hemorrhage.

CONCLUSIONS

The administration of SLX-OH or Z, analogs of the selectin ligand SLe$^x$, blocked IgG but not IgA immune complex-induced neutrophil accumulation and the pathological sequelae (plasma extravasation and hemorrhage) associated with immune complex deposition. These data are consistent with previous studies demonstrating the neutrophil and E-selectin dependency of IgG but not IgA immune complex-induced pulmonary injury on the activation of adherent neutrophils in close juxtaposition with the vascular endothelium. The results not only support a role for neutrophils in mediating tissue damage but also support the concept that a therapeutic benefit may be derived using Z to prevent neutrophil accumulation thus protecting tissue from the potentially harmful consequences of inappropriate neutrophil activation. The specificity of the effect of Z was demonstrated by determining that SLN, a non-fucosylated analog of Z, did not inhibit IgG immune complex induced lung injury.

EXAMPLE 20

Treatment of myocardial ischemia-reperfusion injury

This example demonstrates the effect of Z on myocardial ischemia-reperfusion injury in the cat heart.

A model of myocardial ischemia and reperfusion injury in cats was performed according to the methods of Tsao et al (*Circulation* 82:1402–1412 (1990), which is incorporated herein by reference. Briefly, male cats (2.5–3.5 Kg) were anesthetized with sodium pentobarbital (30 mg/Kg, i.v.). An intratracheal tube was inserted through a mid-line incision and all cats were given intermittent positive pressure ventilation by a Harvard small animal respirator. A polyethylene catheter was inserted into the external jugular vein and the right femoral vein was cannulated and connected to a Statham P23AC pressure transducer for the measurement of arterial blood pressure. A midline thoracotomy was performed, the pericardium was opened and the heart was exposed. A 2–0 silk suture was carefully placed around the left anterior descending artery (LAD) 10–12 mm from its origin. After a 30 minute period of stabilization myocardial ischemia was initiated by complete ligation of the LAD for 1.5 hours of ischemia followed by 4.5 hours of reperfusion. Z (10 mg/Kg in PBS) or PBS alone were administered intravenously 10 minutes prior to the initiation of reperfusion.

The ischemic myocardium was determined as that portion of tissue which did not stain with nitroblue tetrazolium and was expressed as a percentage of the area at risk. Area at risk was determined by reocclusion of the LAD at the end of the reperfusion period followed by the injection of Evans blue dye into the left atrium. The area of risk was, therefore, determined by negative staining.

Endothelial dependent relaxation of coronary artery rings was determined by measuring the acetylcholine-induced relaxation of rings previously contracted with the thromboxane A2 mimetic U46619. Data are expressed as percentage relaxation. Creatinine kinase enzyme levels were measured immunochemically in plasma samples collected at the end of the reperfusion period. The adherence of PMNs to sections of coronary artery was measured in vitro using fluorescene labelled autologous cat neutrophils.

Results

Figure 21:
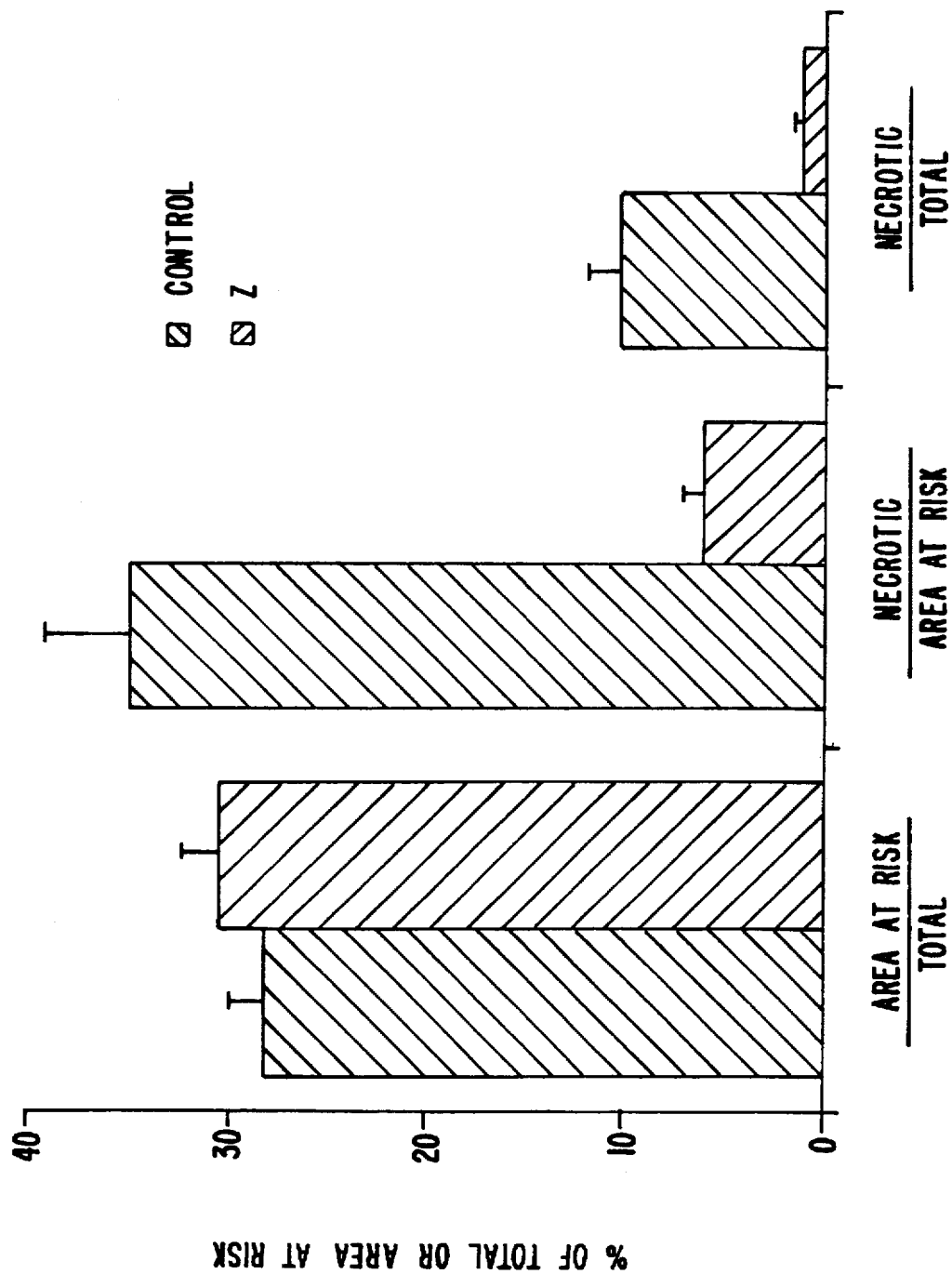
FIG. 21 shows the effect of Z on ischemia reperfurion induced myocardial necrosis in cat.

In cats treated with Z the extent of myocardial ischemia was 6±1% of the area at risk (FIG. 21). In contrast, the extent of ischemia in control animals was significantly (P<0.01) greater at 35±4% of the area at risk. Endothelial dependent relaxation to acetylcholine was significantly preserved in ischemic-reperfused coronary arteries taken from cats treated with Z compared to controls (73±7 vs 22±6%, P<0.01). The plasma concentration of creatinine kinase in Z treated animal (7±1 IU/mg protein) was significantly (P<0.01) less than in control animals (25±3 IU/mg protein). Z at a concentration of 250μM blocked the adhesion of cat PMNs to thrombin (2 unit/mL) stimulated coronary vascular endothelium. In addition the adherence of PMNs to coronary endothelium from Z treated animals was less than that determined in control animals.

CONCLUSION

Both in vitro and in vivo studies have demonstrated the ability of Z to block leukocyte-endothelial cell interactions and consequently the ability of Z to reduce the pathological sequelae of inflammation. Thus, the utility of compounds made according to the present invention is demonstrated by these examples. Other data generated in dermal and pulmonary models of inflammation, however, do not provide evidence of the ability of Z to inhibit leukocyte accumulation.

Although the foregoing invention has been described in some detail by way of illustration and example for purposes of clarity of understanding, it will be apparent that certain changes and modifications may be practiced within the scope of the appended claims.

What is claimed is:

1. A method for inhibiting selectin-mediated intercellular adhesion in a mammal, the method comprising administering to the mammal a therapeutically effective dose of a pharmaceutical composition comprising a pharmaceutically acceptable carrier and a compound which selectively binds P-selectin or E-selectin, wherein the compound is selected from the group consisting of compounds of formula I and compounds of formula II,

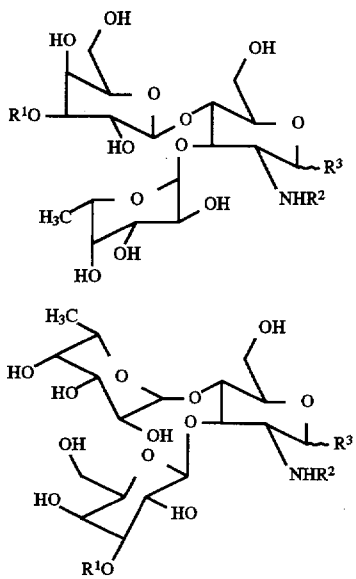

in which:

$R^1$ is selected from the group consisting of a sialic acid and a group having the formula III

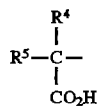

in which:

$R^4$ and $R^5$ taken individually are the same or different and are selected from the group consisting of H, $C_1$–$C_8$ alkyl, hydroxy-($C_1$–$C_8$ alkyl), aryl-($C_1$–$C_8$alkyl), and ($C_1$–$C_8$ alkoxy)-($C_1$–$C_8$ allkyl), substituted or unsubstituted, or $R^4$ and $R^5$ form a single radical which is selected from the group consisting of —$R^6$— and —$(R^7)_q$—O—$(R^8)_r$—, in which $R^6$ is $C_3$–$C_7$ divalent alkyl, substituted or unsubstituted, $R^7$ and $R^8$ are the same or different and are $C_1$–$C_6$ divalent alkyl, substituted or unsubstituted, and q and r are the same or different and are zero or 1 such that the sum of q and r is at least 1;

the substitutions in the substituted groups being selected from the group consisting of hydroxy, hydroxy($C_1$–$C_4$ alkyl), polyhydroxy($C_1$–$C_4$, alkyl), and alkanoamido;

$R^2$ is selected from the group consisting of ($C_1$–$C_8$ alkyl)carbonyl, ($C_1$–$C_8$ alkoxy)carbonyl, ($C_2$–$C_9$ alkenyloxy)carbonyl; and $R^3$ is selected from the group consisting of Man; GalNAc; Gal; β1,3Galβ1,4Glc; α1,2Man; α1,6GalNAc; α1,2Man-$R^9$; α1,6GalNAc-$R^9$; and β1,3Gal-$R^9$, wherein $R^9$ is attached to the anomeric carbon and is selected from the group consisting of —OH, $C_1$–$C_{20}$ alkyl, $C_1$–$C_{20}$ alkoxy, aryl-($C_1$–$C_8$ alkyl), ($C_1$–$C_8$ alkyl)-aryl, and alkylthio.

2. The method of claim 1, wherein $R^3$ is β1,3Gal-$R^9$.

3. The method of claim 2, wherein $R^9$ is $C_1$–$C_{20}$ alkoxy.

4. A method for inhibiting selectin-mediated intercellular adhesion in a mammal, the method comprising administering to the mammal a therapeutically effective dose of a pharmaceutical composition comprising a pharmaceutically acceptable carrier and compound having the formula:

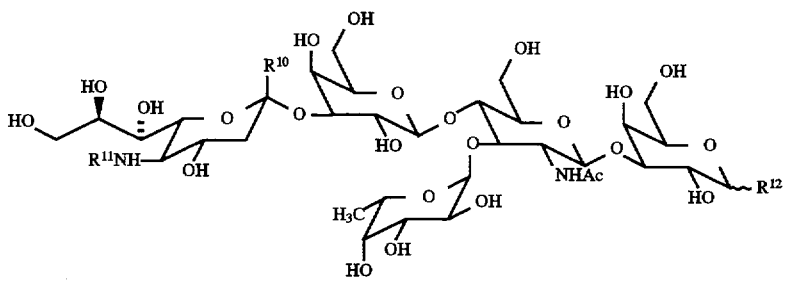

wherein $R^{10}$ is selected from the group consisting of a carboxylic acid moiety and a carboxylic acid salt, $R^{11}$ is selected from the group consisting of an acetyl and a glycolyl radical and $R^{12}$ is $C_1$–$C_{20}$ alkoxy.

5. The method of claim 4, wherein $R^{12}$ is ethoxy.

6. The method of claim 4, wherein $R^{10}$ is a salt of carboxylic acid.

7. The method of claim 6, wherein the salt is a sodium salt.

8. The method of claim 4, wherein $R^{11}$ is acetyl.

9. The method of claim 4, wherein the compound has the formula:

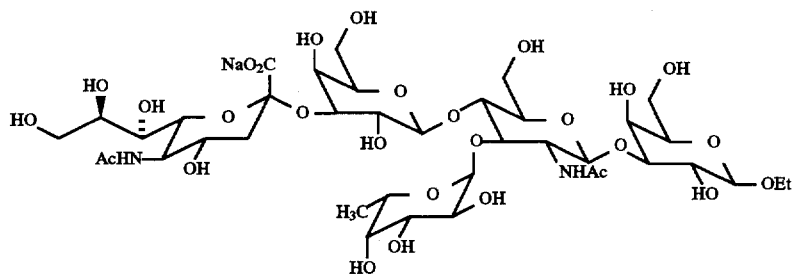
* * * * *